United States Patent
Agulnick et al.

(10) Patent No.: US 9,109,245 B2
(45) Date of Patent: Aug. 18, 2015

(54) CELL COMPOSITIONS DERIVED FROM DEDIFFERENTIATED REPROGRAMMED CELLS

(71) Applicant: ViaCyte, Inc., San Diego, CA (US)

(72) Inventors: Alan D. Agulnick, San Diego, CA (US); Olivia Kelly, San Diego, CA (US); Yuki Ohi, La Jolla, CA (US); Allan Robins, Athens, GA (US); Thomas Schultz, Athens, GA (US)

(73) Assignee: ViaCyte, Inc., San Diego, CA (US)

( * ) Notice: Subject to any disclaimer, the term of this patent is extended or adjusted under 35 U.S.C. 154(b) by 0 days.

(21) Appl. No.: 13/761,078

(22) Filed: Feb. 6, 2013

(65) Prior Publication Data

US 2013/0164787 A1 Jun. 27, 2013

Related U.S. Application Data

(63) Continuation-in-part of application No. 12/765,714, filed on Apr. 22, 2010, now abandoned.

(60) Provisional application No. 61/171,759, filed on Apr. 22, 2009.

(51) Int. Cl.

| C12N 5/00 | (2006.01) |
| C12N 5/071 | (2010.01) |
| C12N 5/07 | (2010.01) |
| C07K 14/475 | (2006.01) |
| C12P 21/00 | (2006.01) |
| C12N 5/10 | (2006.01) |
| A61K 35/39 | (2015.01) |

(52) U.S. Cl.
CPC .............. *C12P 21/00* (2013.01); *A61K 35/39* (2013.01); *C12N 2500/25* (2013.01); *C12N 2501/11* (2013.01); *C12N 2501/117* (2013.01); *C12N 2501/16* (2013.01); *C12N 2501/195* (2013.01); *C12N 2501/385* (2013.01); *C12N 2501/41* (2013.01); *C12N 2501/415* (2013.01); *C12N 2501/727* (2013.01); *C12N 2506/45* (2013.01)

(58) Field of Classification Search
None
See application file for complete search history.

(56) References Cited

U.S. PATENT DOCUMENTS

| 5,453,357 | A | 9/1995 | Hogan |
| 5,478,838 | A | 12/1995 | Arita et al. |
| 5,529,914 | A | 6/1996 | Hubbell et al. |
| 5,670,372 | A | 9/1997 | Hogan |
| 5,690,926 | A | 11/1997 | Hogan |
| 5,801,033 | A | 9/1998 | Hubbell et al. |
| 5,843,780 | A | 12/1998 | Thomson |
| 6,075,007 | A | 6/2000 | Economides et al. |
| 6,200,806 | B1 | 3/2001 | Thomson |
| 6,251,671 | B1 | 6/2001 | Hogan et al. |
| 6,258,870 | B1 | 7/2001 | Hubbell et al. |
| 6,759,039 | B2 * | 7/2004 | Tsang et al. ............. 424/93.7 |
| 6,800,480 | B1 | 10/2004 | Bodnar et al. |
| 6,911,227 | B2 | 6/2005 | Hubbell et al. |
| 7,005,252 | B1 | 2/2006 | Thomson |
| 7,427,415 | B2 | 9/2008 | Scharp et al. |
| 7,432,104 | B2 | 10/2008 | Mitalipova et al. |
| 7,510,876 | B2 | 3/2009 | D'Amour et al. |
| 7,534,608 | B2 | 5/2009 | Martinson et al. |
| 7,541,185 | B2 | 6/2009 | D'Amour et al. |
| 7,695,963 | B2 | 4/2010 | Agulnick et al. |
| 7,695,965 | B2 | 4/2010 | Martinson et al. |
| 2002/0072117 | A1 | 6/2002 | Xu et al. |
| 2002/0081725 | A1 | 6/2002 | Tsang et al. |
| 2003/0087919 | A1 | 5/2003 | Nagarathnam et al. |
| 2003/0125344 | A1 | 7/2003 | Nagarathnam et al. |
| 2003/0175956 | A1 | 9/2003 | Bodnar et al. |
| 2004/0002507 | A1 | 1/2004 | Nagarathnam et al. |
| 2004/0002508 | A1 | 1/2004 | Nagarathnam et al. |
| 2004/0014755 | A1 | 1/2004 | Nagarathnam et al. |
| 2005/0192304 | A1 | 9/2005 | Nagarathnam et al. |
| 2005/0209261 | A1 | 9/2005 | Nagarathnam et al. |
| 2005/0266554 | A1 | 12/2005 | D'Amour et al. |
| 2007/0122905 | A1 | 5/2007 | D'Amour et al. |
| 2007/0259421 | A1 * | 11/2007 | D'Amour et al. ............. 435/366 |
| 2008/0233610 | A1 | 9/2008 | Thomson et al. |
| 2009/0047263 | A1 | 2/2009 | Yamanaka et al. |
| 2009/0092586 | A1 * | 4/2009 | Verfaillie et al. ............ 424/93.7 |
| 2009/0104696 | A1 | 4/2009 | Robins et al. |
| 2009/0263896 | A1 | 10/2009 | Kelly et al. |
| 2009/0298178 | A1 | 12/2009 | D'Amour et al. |
| 2010/0003757 | A1 | 1/2010 | Mack et al. |
| 2010/0112691 | A1 | 5/2010 | Green et al. |
| 2010/0124564 | A1 | 5/2010 | Martinson et al. |
| 2010/0272695 | A1 | 10/2010 | Agulnick et al. |

FOREIGN PATENT DOCUMENTS

| WO | WO 00/59525 A2 | 10/2000 |
| WO | WO 02/076976 A2 | 10/2002 |
| WO | WO 03/059913 A1 | 7/2003 |
| WO | WO 03/062225 A1 | 7/2003 |
| WO | WO 03/062227 A1 | 7/2003 |
| WO | WO 2005/051753 A1 | 6/2005 |
| WO | WO 2005/080598 A1 | 9/2005 |
| WO | WO 2007/101130 | 9/2007 |
| WO | WO 2008/011882 A1 | 1/2008 |
| WO | WO 2008/013664 | 1/2008 |
| WO | WO 2009/052505 A1 | 4/2009 |
| WO | WO 2009/117439 | 9/2009 |
| WO | WO 2009/154606 A1 | 12/2009 |
| WO | WO 2010/053472 A1 | 5/2010 |

OTHER PUBLICATIONS

"Heregulin beta, EGF Domain (HRGb)." Dec. 4, 2013. Labome. Available online at <http://www.labome.com/product/US-Biological/H2030-50.html>. Accessed Jan. 7, 2014.*

(Continued)

*Primary Examiner* — Lora E Barnhart Driscoll
(74) *Attorney, Agent, or Firm* — Mintz Levin Cohn Ferris Glovsky and Popeo PC

(57) ABSTRACT

Disclosed herein are cell culture compositions, for example, pancreatic cell culture compositions, derived from dedifferentiated human reprogrammed pluripotent stem cells, such as induced pluripotent stem (iPS) cells, and methods for producing and using such cell culture compositions.

8 Claims, 16 Drawing Sheets

(56) References Cited

OTHER PUBLICATIONS

"Pro-neuregulin-4, membrane-bound isoform [*Homo sapiens*]." Nov. 24, 2013. National Center for Biotechnology Information. Available online at <http://www.ncbi.nlm.nih.gov/protein/20070380>. Accessed Jan. 7, 2014.*
Wang L. 2007. Self-renewal of human embryonic stem cells requires insulin-like growth factor-1 receptor and ERBB2 receptor signaling. Blood 110: 4111-4119.*
Cleaver O et al. 2005. "Development of the endocrine pancreas." In Joslin's Diabetes Mellitus (14th ed.) (Boston: Joslin Diabetes Center; Kahn C et al., eds.) pp. 29-30.*
Memon AA et al. 2004. Expression of HER3, HER4 and their ligand heregulin-4 is associated with better survival in bladder cancer patients. Br J Cancer 91: 2034-2041.*
Dor Y et al. 2004. Adult pancreatic beta-cells are formed by self-duplication rather than stem-cell differentiation. Nature 429: 41-46.*
Agarwal et al., "Efficient differentiation of functional hepatocytes from human embryonic stem cells", *Stem Cells*, (2008) 26:1117-1127.
Attisano et al., "Activation of signalling by the activin receptor complex", *Mol. Cell Biol.*, (1996) 16(3):1066-1073.
Borowiak et al., "Small molecules efficiently direct endodermal differentiation of mouse and human embryonic stem cells", *Cell Stem Cell*, (2009) 4:348-358.
Brunner et al., "Distinct DNA methylation patterns characterize differentiated human embryonic stem cells and developing human fetal liver", *Genome Res.*, (2009) 19:1044-1056.
Chang et al., Genetic analysis of the mammalian transforming growth factor-beta superfamily, *Endocrine Review*, (2002) 23(6):787-823.
Chang et al., "Rho Kinases Regulate the Renewal and Neural Differentiation of Embryonic Stem Cells in Cell Plating Density-Dependent Manner" *PLoS ONE* (2010) 5(2) (e9187):1-9.
Chen et al., "Improved production and purification of minicircle DNA vector free of plasmid bacterial sequences and capable of persistent transgene expression in vivo", *Hum. Gene Ther.*, (2005) 16:126-131.
Chen et al., "Minicircle DNA vectors devoid of bacterial DNA result in persistent and high-level transgene expression in vivo", *Mol. Ther.*, (2003) 8:495-500.
D'Amour et al. "Production of Pancreatic Hormone-Expressing Endocrine Cells From Human Embryonic Stem Cells" (Nov. 1, 2006) Nature Biotechnology 24, 1392-1401.
D'Amour et al., "Efficient differentiation of human embryonic stem cells to definitive endoderm." Nature Biotechnology, Dec. 2005, vol. 23, No. 12, pp. 1534-1541.
Derynck et al., *Cell*, "Smads: transcriptional activators of TGF-beta responses", (1998) 95(6):737-740.
Dimos et al., "Induced pluripotent stem cells generated from patients with ALS can be differentiated into motor neurons", *Science*, (2008) 321:1218-21.
Ebert et al., "Induced pluripotent stem cells from a spinal muscular atrophy patient", *Nature*, (2009) 457:277-80.
Foster et al., "Induction of KLF4 in basal keratinocytes blocks the proliferation-differentiation switch and initiates squamous epithelial dysplasia", *Oncogene*, (2005) 24:1491-1500.
Guilluy et al., "Rho protein crosstalk: another social network?" *Trends in Cell Biology*, (2011) 21(12): 718-726.
Hammar et al., Role of the Rho-Rock (Rho-Associated Kinase) signaling pathway in the regulation of pancreatic cell function., *Endocrinology*, 2009, vol. 150, No. 5, 2072-2079.
Hochedlinger et al., "Ectopic expression of Oct-4 blocks progenitor-cell differentiation and causes dysplasia in epithelial tissues", *Cell*, (2005) 121:465-477.
Huangfu et al., "Induction of Pluripotent Stem Cells from Primary Human Fibroblasts with only Oct4 and Sox2," *Nature Biotechnology*, 2008 vol. 26, No. 11, 1269-1275.

Jia et al., "A nonviral minicircle vector for deriving human iPS cells", *Nature Methods*, (2010) 7(3):197-199.
Kaji et al., "Virus-free induction of pluripotency and subsequent excision of reprogramming factors", *Nature*, (2009) 458(7239):771-5.
Kim et al., "Generation of human induced pluripotent stem cells by direct delivery of reprogramming proteins", *Cell Stem Cell*, (2009) 4(6):472-6.
Maehr et al., "Generation of pluripotent stem cells from patients with type 1 diabetes", *Proc. Natl. Acad. Sci. USA*, (2009) 106(37):15768-73.
Massaqué, "How cells read TGF-beta signals", *Mol. Cell. Biol.*, (2000) 1(3):169-78.
Mathews, "Activin receptors and cellular signaling by the receptor serine kinase family", *Endocr. Rev.*, (1994) 15(3):310-325.
McLean et al., "Activin a efficiently specifies definitive endoderm from human embryonic stem cells only when phosphatidylinositol 3-kinase signaling is suppressed", *Stem Cells*, (2007) 25(1):29-38.
Okita et al., "Generation of mouse induced pluripotent stem cells without viral vectors", *Science*, (2008) 322(5903):949-53.
Park et al., "Disease-specific induced pluripotent stem cells", *Cell*, (2008) 134(5):877-86.
Park et al., "Reprogramming of human somatic cells to pluripotency with defined factors", *Nature*, (2008) 45(7175):141-6.
Segev et al., "Differentiation of human embryonic stem cells into insulin-producing clusters," *Stem Cells* (2004) 22:265-274.
Soldner et al., "Parkinson's disease patient-derived induced pluripotent stem cells free of viral reprogramming factors", *Cell*, (2009) 136:964-977.
Sosa-Pineda, B. "The Gene Pax4 is an Essential Regulator of Pancreatic β-Cell Development," *Molecules and Cells*, 2004, vol. 18, No. 3, 289-294.
Stadtfeld et al., "Induced pluripotent stem cells generated without viral integration", *Science*, (2008) 322:945-949.
Takahashi et al., "Induction of Pluripotent Stem Cells from Mouse Embryonic and Adult Fibroblast Cultures by Defined Factors" *Cell*, (2006), 126:663-676.
Takahashi et al., "Induction of pluripotent stem cells from adult human fibroblasts by defined factors", *Cell* (2007), 131(5):861-872.
Takahashi et al., "Induction of pluripotent stem cells from adult human fibroblasts by defined factors", *Cell* (2007), 131:1-12.
Watanabe et al., "A ROCK inhibitor permits survival of dissociated human embryonic stem cells." *Nat Biotech*, (2007) 25:681-686.
Wernig et al., "In vitro reprogramming of fibroblasts into a pluripotent ES-cell-like state", *Nature*, (2007) 448:318-324.
Woltjen et al., "piggyBac transposition reprograms fibroblasts to induced pluripotent stem cells", *Nature*, (2009) 458(7239):766-770.
Yu et al. "Induced pluripotent stem cell lines derived from human somatic cells", *Science*, (2007), 318(5858):1917-20.
Yu et al., "Human induced pluripotent stem cells free of vector and transgene sequences", *Science*, 324(5928):797-801.
Zhang et al., "Highly efficient differentiation of human ES cells and IPS cells into mature pancreatic insulin-producing cells," *Cell Research* (2009): 429-438.
Zhou et al., "Generation of induced pluripotent stem cells using recombinant proteins", *Cell Stem Cell*, (2009), 4(5):381-384.
International Search Report and Written Opinion dated Jun. 30, 2014 for International Application No. PCT/US2014/015156, 11 pages.
Jeon et al., "Differentiation and Transplantation of Functional Pancreatic Beta Cells Generated from Induced Pluripotent Stem Cells Derived from a Type 1 Diabetes Mouse Model", *Stem Cells and Development*, 21(14): 2642-2655; 2012.
Zhu et al., "Generation of pancreatic insulin-producing cells from rhesus monkey induced pluripotent stem cells", *Diabetologia*, 54(9):2325-2336; 2011.

* cited by examiner

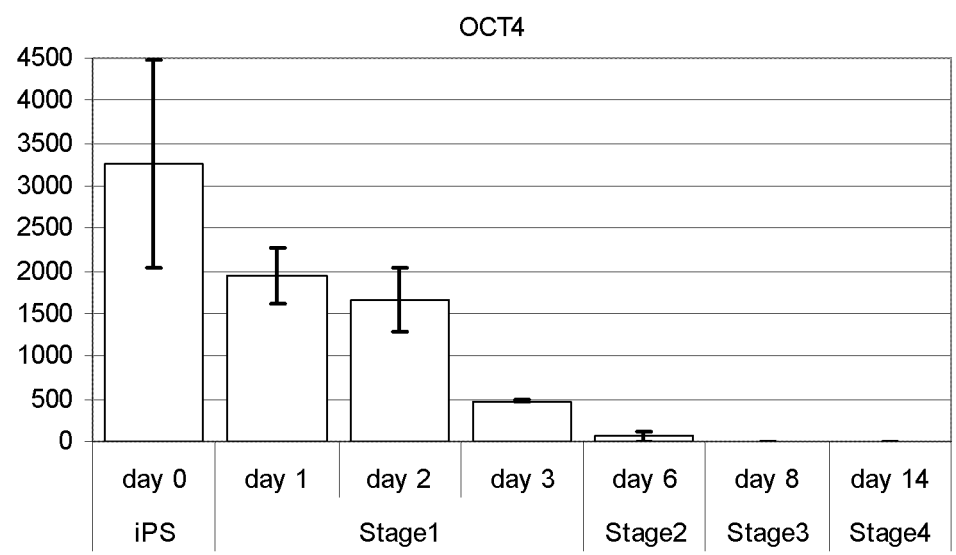
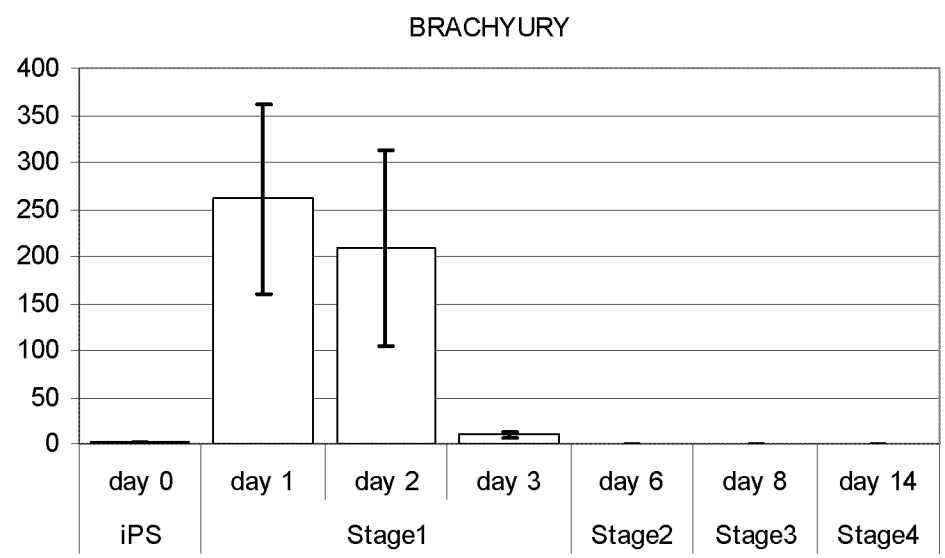
FIG. 2A-B

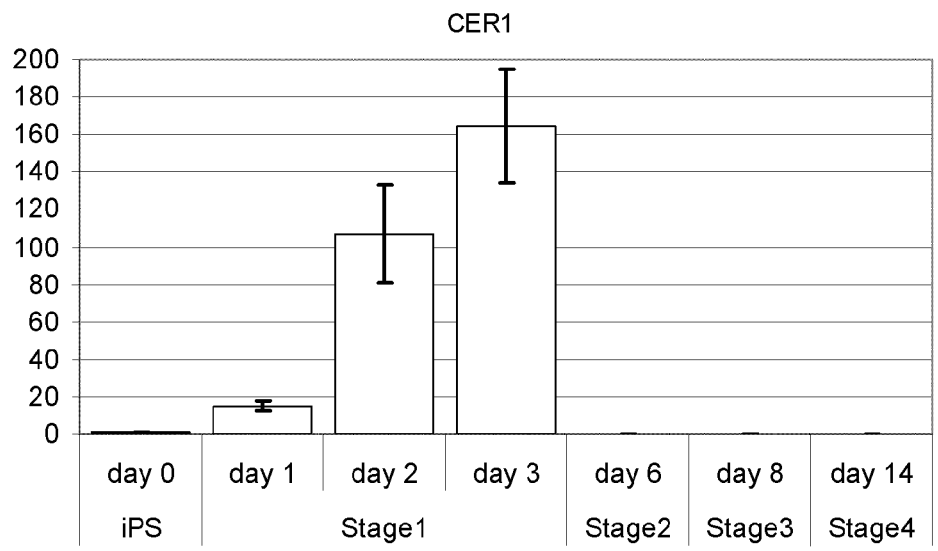
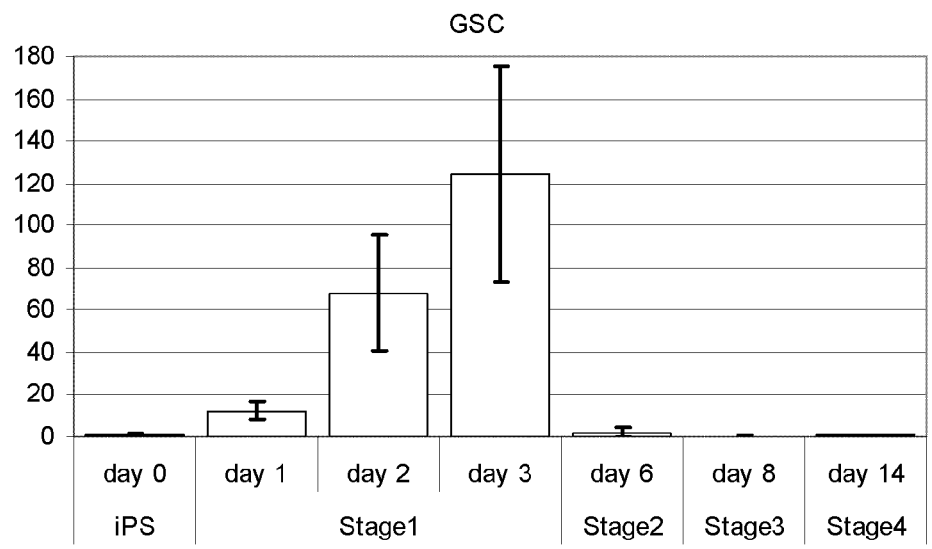
FIG. 2C-D

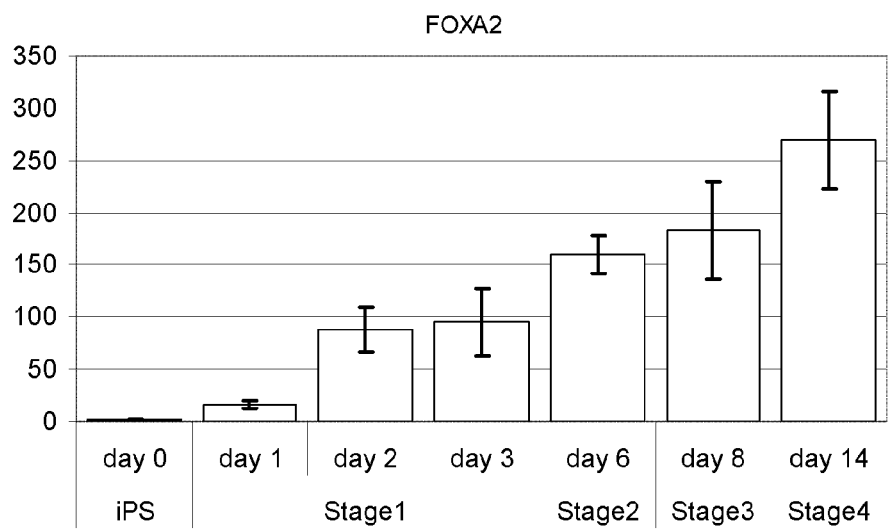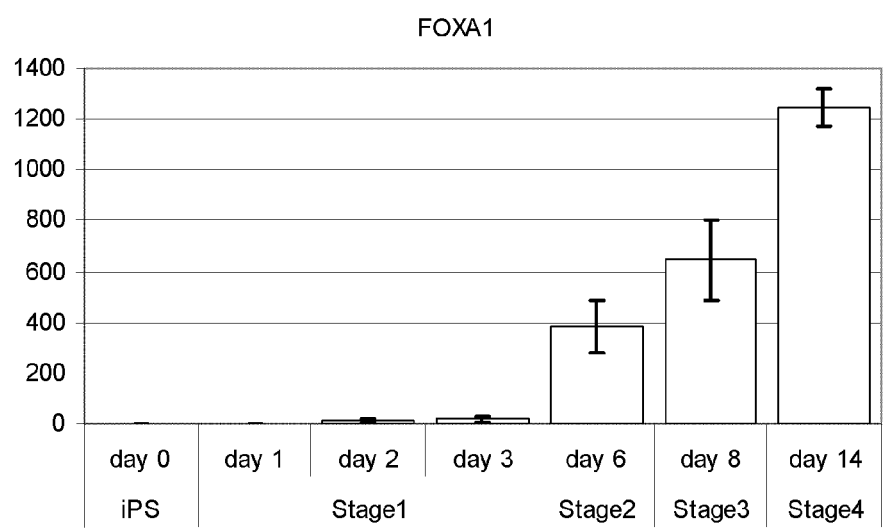
FIG. 2E-F

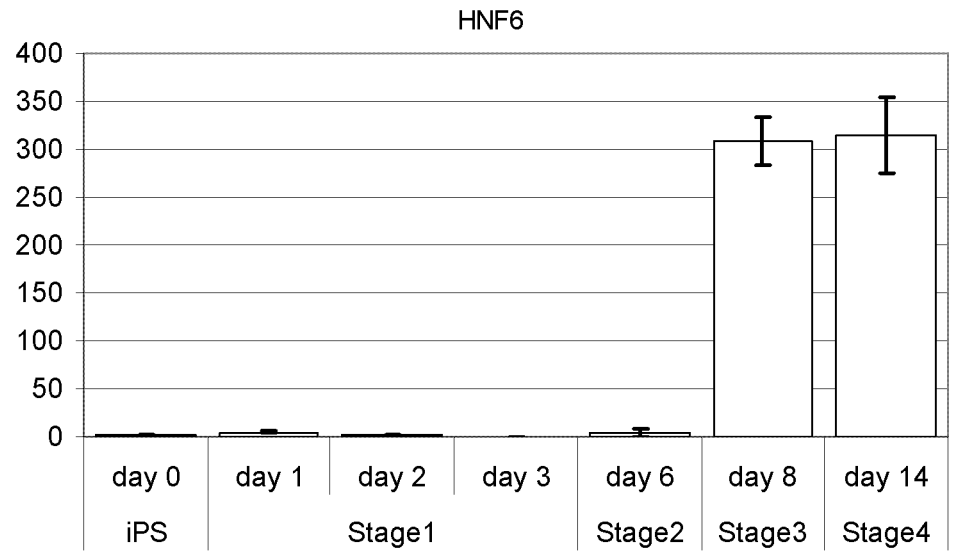
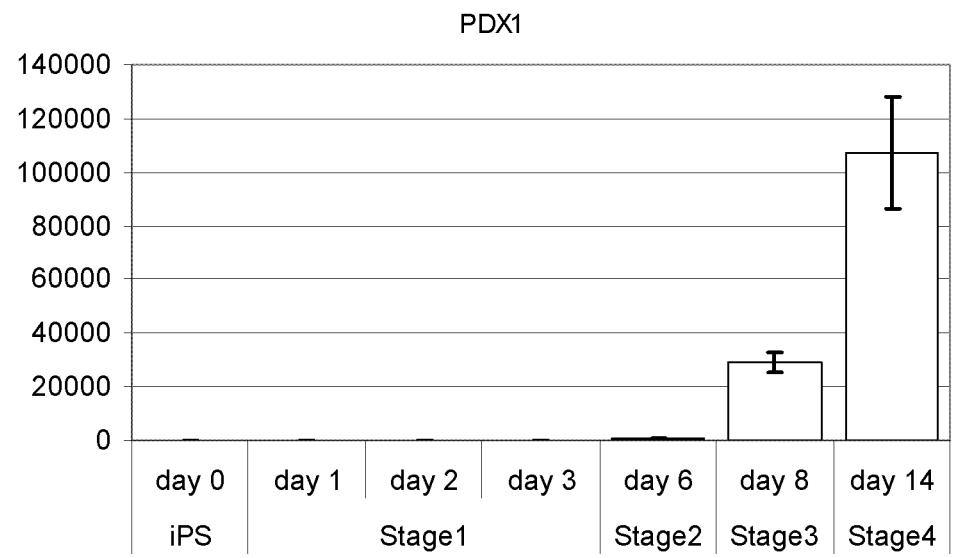
FIG. 2G-H

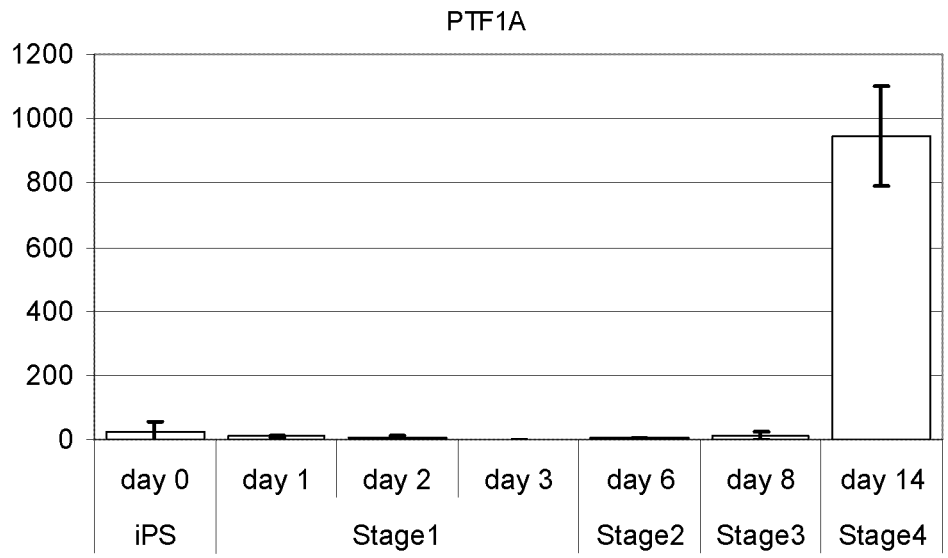
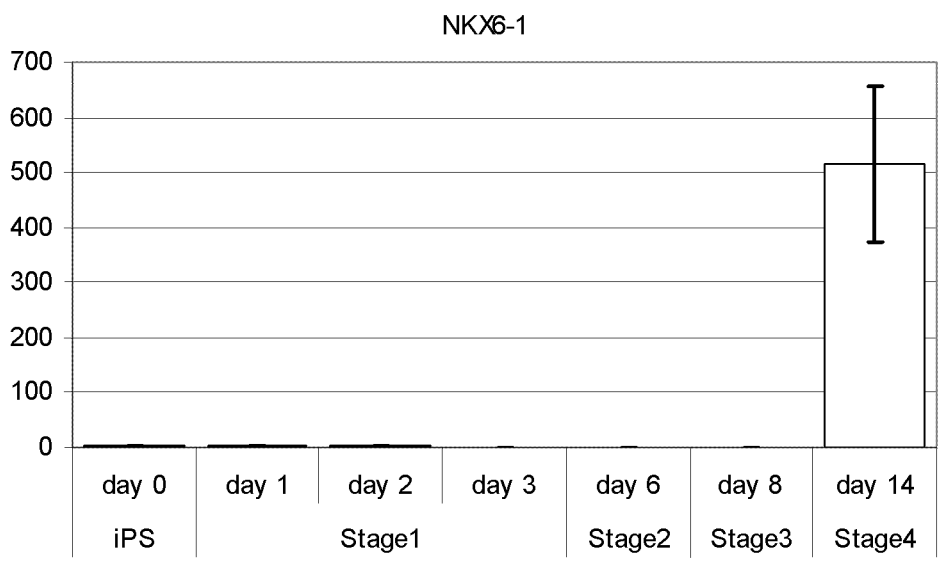
FIG. 2I-J

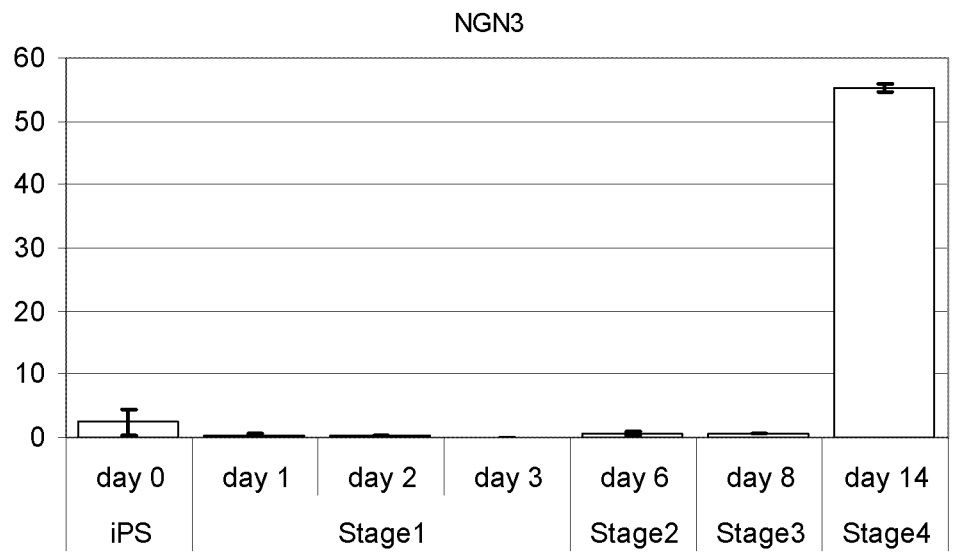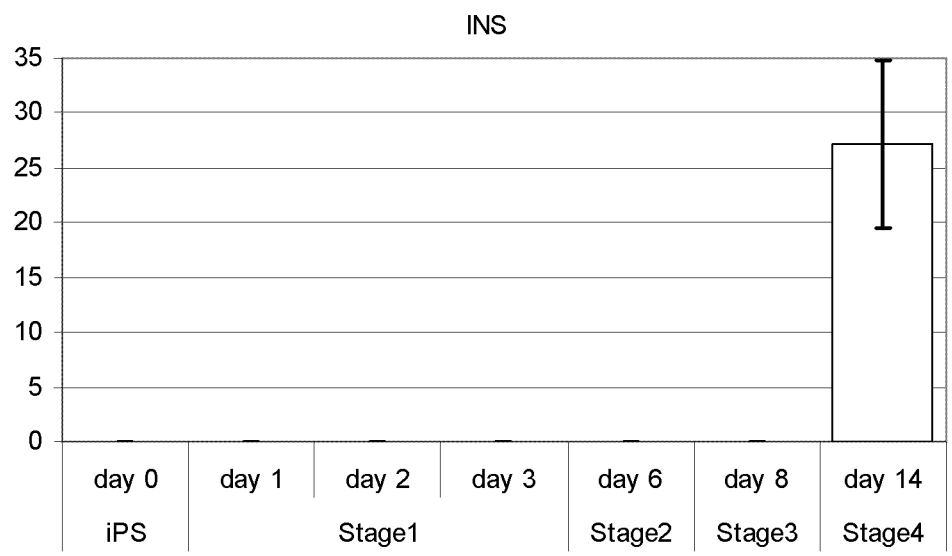
FIG. 2K-L

E2021 using G4 hIPS cell line at Stage 4 differentiation (PDX1-positive pancreatic endoderm cells)
    A) Pdx1
    B) Nkx6.1
    C) Ptf1a
    D) Dapi

*E2021 G4 hIPS cell line at Stage 5*
  *A) Glucagon*
  *B) Insulin*
  *C) Somatostatin*
  *D) Dapi*

CELL COMPOSITIONS DERIVED FROM DEDIFFERENTIATED REPROGRAMMED CELLS

CROSS-REFERENCE TO RELATED APPLICATIONS

This application is continuation-in-part of U.S. patent application Ser. No. 12/765,714, entitled CELL COMPOSITIONS DERIVED FROM DEDIFFERENTIATED REPROGRAMMED CELLS, filed Apr. 22, 2010, which is a nonprovisional application claiming priority under 35 U.S.C. §119 (e) to U.S. Provisional Patent Application No. 61/171,759, entitled CELL COMPOSITIONS DERIVED FROM DEDIFFERENTIATED REPROGRAMMED CELLS, filed Apr. 22, 2009, the disclosures of which are incorporated herein by reference in their entireties.

SEQUENCE LISTING

The present application is being filed along with a Sequence Listing in electronic format. The Sequence Listing is provided as a file entitled CYTHERA068P1.TXT, created Jan. 28, 2013, which is 9.04 Kb in size. The information in the electronic format of the Sequence Listing is incorporated herein by reference in its entirety.

FIELD OF THE INVENTION

This invention relates generally to the isolation, maintenance, and use of cell cultures. More specifically, it relates to cell compositions derived from induced pluripotent stem cells.

BACKGROUND

An important application of pluripotent cells is their use in cell therapy. Pluripotent stem cells include, but are not limited to, human embryonic stem (hES) cells, human embryonic germ (hEG) cells. Still other types of pluripotent cells exist, for example, dedifferentiated mouse and human stem cells, i.e. differentiated somatic adult cells are dedifferentiated to become pluripotent-like stem cells. These dedifferentiated cells induced to establish cells having pluripotency and growth ability similar to those of ES cells are also called "induced pluripotent stem (iPS) cells", "embryonic stem cell-like cells", "ES-like cells", or equivalents thereof. Such cells are potentially viable alternative pluripotent cells. The therapeutic application of iPS cells will require demonstrating that these cells are stable and show an appropriate safety profile in preclinical studies to treat diabetes and other diseases. Reprogramming of differentiated human somatic cells into a pluripotent state allows for patient- and disease-specific stem cells. See Takahashi, K. et al. Cell, 1-12, 2007 and Ju, J. et al. Science 2007. Takahashi et al. and Ju et al. each introduced four genes into adult and fetal/newborn fibroblasts to generate the iPS cells: Oct4, Sox2, Klf4 and c-myc by Takahashi et al.; Oct4, Sox2, Nanog and Lin28 by Ju et al. In either case, iPS cells had some characteristics of hES cells including, hES cell morphology, marker expression, prolonged proliferation, normal karyotype, and pluripotency.

Although, iPS cells may provide a cell therapy-based regenerative medicine without the associated ethical controversy, the differentiation properties of iPS cells, for example, differentiation potential and efficiency of the differentiation in vitro, are still unclear, and a directed differentiation method for iPS cells has not been demonstrated. Hence, there is a need to determine and demonstrate detailed differentiation properties and the directional differentiation efficiencies of iPS cells.

SUMMARY OF THE INVENTION

Embodiments described herein provide for cell compositions derived from pluripotent cells, for example, dedifferentiated reprogrammed cells, such as induced pluripotent stem (iPS) cells.

One embodiment provides for compositions and methods of making an in vitro cell culture comprising human cells wherein at least about 15% of the human cells are definitive endoderm cells, wherein the definitive cells are derived from dedifferentiated genetically reprogrammed cells. In one aspect, the definitive endoderm cells are multipotent cells that can differentiate into cells of the gut tube or organs derived therefrom.

Another embodiment provides for compositions and methods of making an in vitro cell culture comprising human cells wherein at least about 15% of the human cells are pancreatic-duodenal homeobox factor-1 (PDX1) positive foregut endoderm cells, wherein the PDX1 positive foregut endoderm cells are derived from dedifferentiated genetically reprogrammed cells. In one aspect, the PDX1 positive foregut endoderm cells are PDX1, SOX9, PROX1 and HNF6 co-positive A further embodiment provides for compositions and methods of making an in vitro cell culture comprising human cells wherein at least about 15% of the human cells are pancreatic-duodenal homeobox factor-1 (PDX1) positive pancreatic progenitor cells, wherein the PDX1 positive pancreatic progenitor cells are derived from dedifferentiated genetically reprogrammed cells. In one aspect, the PDX1 positive pancreatic progenitor cells are PDX1 and NKX6.1 co-positive.

Still another embodiment provides for compositions and methods of making an vitro cell culture comprising human cells wherein at least about 15% of the human cells are Neurogenin 3 (NGN3) positive endocrine precursor cells, wherein the NGN3 endocrine precursor cells are derived from dedifferentiated genetically reprogrammed cells. In one aspect, the NGN3 positive endocrine precursor cells are NGN3, PAX4 and NKX2.2 co-positive.

Further embodiments of the cell culture compositions described herein include in vitro human pancreatic endoderm cell cultures comprising differentiated cells derived from dedifferentiated genetically reprogrammed cells and an ERBB receptor tyrosine kinase activating agent.

Additional embodiments described herein relate to a method for producing insulin. In some such embodiments, the method comprises the steps of (a) contacting at least a foregut endoderm cell culture and/or at least a PDX1 negative foregut endoderm cell culture derived from dedifferentiated genetically reprogrammed cells in vitro with an ERBB receptor tyrosine kinase activating agent, thereby producing a pancreatic endoderm cell population comprising endocrine cell and non-endocrine cell sub-populations; and (b) transplanting and maturing the pancreatic endoderm cell population of step (a) or a cell subpopulation of step (a) in vivo, thereby obtaining insulin secreting cells, wherein the insulin secreting cells secrete insulin in response to glucose stimulation.

Still other embodiments described herein relate to a method for producing insulin, the method comprising the steps of: (a) contacting dedifferentiated genetically reprogrammed cells in vitro with a first medium comprising an agent that activates a TGFβ receptor family member; (b)

culturing, in vitro, the cells of step (a) in a second medium lacking the agent that activates a TGFβ receptor family member, thereby generating at least foregut endoderm cells and/or at least PDX1 negative foregut endoderm cells; (c) contacting the cells of step (b) with an ERBB receptor tyrosine kinase activating agent, thereby generating a cell population comprising endocrine cell and non-endocrine cell sub-populations; and (d) transplanting and maturing the cell population of step (c) or a cell subpopulation of step (c) in vivo, thereby obtaining insulin secreting cells, wherein the insulin secreting cells secrete insulin in response to glucose stimulation. Still other embodiments described herein relate to contacting a population comprising at least foregut endoderm cells, at least PDX1 negative foregut endoderm cells, and/or at least PDX1 positive pancreatic endoderm cells with an ERBB receptor tyrosine kinase activating agent, thereby generating a cell population capable of maturing to glucose-responsive insulin-secreting cells in vivo.

Still other embodiments described herein relate to contacting a population comprising at least foregut endoderm cells, at least PDX1 negative foregut endoderm cells, and/or at least PDX1 positive pancreatic endoderm cells with an ERBB receptor tyrosine kinase activating agent and a rho-kinase inhibitor, thereby generating a cell population capable of maturing to glucose-responsive insulin-secreting cells in vivo.

As used herein, the phrases "at least foregut endoderm cells," at least PDX1 negative foregut endoderm cells," and "at least PDX1 positive pancreatic endoderm cells" means that some of or a portion of the cells in the cell population have differentiated from iPSC to foregut endoderm cells or beyond, from iPSC to PDX1 negative foregut endoderm cells or beyond and/or from iPSC to PDX1 positive pancreatic endoderm cells or beyond in their differentiation toward pancreatic islet cells.

As used herein, the phrases "some of" and/or "a portion of," when drawn to cells in a cell population, means that the cell population comprises at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95% or at least more than 95% cells of the specified cell type.

BRIEF DESCRIPTION OF THE DRAWINGS

FIGS. 2A-L are bar graphs showing the relative gene expression levels of OCT4 (FIG. 2A), BRACHYURY (FIG. 2B), CER1 (FIG. 2C), GSC (FIG. 2D), FOXA2 (FIG. 2E), FOXA1 (FIG. 2F), HNF6 (FIG. 2G), PDX1 (FIG. 2H), PTF1A (FIG. 2I), NKX6.1 (FIG. 2J), NGN3 (FIG. 2K) and INS (FIG. 2L). Expression levels are normalized to the average expression levels of housekeeping genes, cyclophilin G and TATA Binding Protein (TBP) expression. The graphs depict fold upregulation over the lowest data point in the data set.

In FIG. 7C, PEC was encapsulated with cell encapsulation devices (Encaptra® EN20, or EN20, ViaCyte, San Diego, Calif.) and in some instances the devices had micro-perforations (pEN20, ViaCyte, San Diego, Calif.). Such devices have been described in U.S. Pat. No. 8,278,106, the disclosure of which is incorporated herein by reference in its entirety.

FIG. 8A shows the blood glucose for each of the 13 mice (baseline with and without heregulin) and FIG. 8B shows the combined average measurements for each treatment (baseline with and without heregulin). Measurements of random non-fasting blood glucose levels are shown for the 13 mice implanted with iPEC grafts up to 14 days before they were treated with STZ (day 0), and for the same mice after STZ treatment and after the grafts were explanted. STZ-treated animals were given STZ about 26 weeks post graft transplant (day 0). At 28 weeks post graft transplant, approximately 2 weeks after initiation of STZ-treatment, the iPEC grafts were explanted (removed). Nonfasting blood glucose measurements were collected over time for each of the animals.

DETAILED DESCRIPTION OF THE INVENTION

Figure 1:
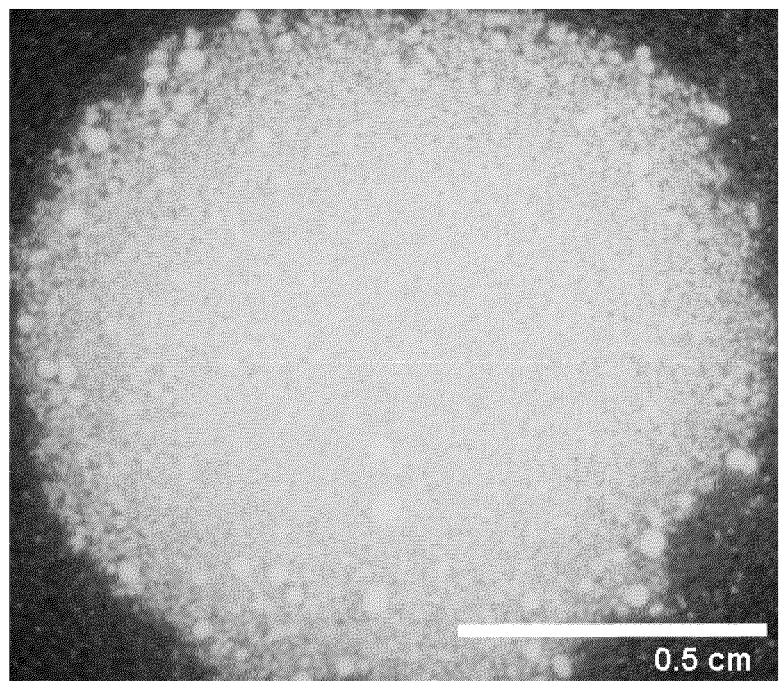
FIG. 1 is a photographic image of an aggregate suspension culture of dedifferentiated reprogrammed cells or, also referred to herein, as iPS cells.

The present invention may be understood more readily by reference to the following detailed description of the preferred embodiments of the invention and the Examples included herein. However, before the present compounds, compositions, and methods are disclosed and described, it is to be understood that this invention is not limited to specific cell types, specific feeder cell layers, specific conditions, or specific methods, etc., and, as such, may vary. Numerous modifications and variations therein will be apparent to those skilled in the art. It is also to be understood that the terminology used herein is for the purpose of describing specific embodiments only and is not intended to be limiting.

DEFINITIONS

It will be appreciated that the numerical ranges expressed herein include the endpoints set forth and describe all integers between the endpoints of the stated numerical range.

Unless otherwise noted, the terms used herein are to be understood according to conventional usage by those of ordinary skill in the relevant art. Also, for the purposes of this specification and appended claims, unless otherwise indicated, all numbers expressing quantities of ingredients, percentages or proportions of materials, reaction conditions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

The practice of embodiments described herein employs, unless otherwise indicated, conventional techniques of cell biology, molecular biology, genetics, chemistry, microbiology, recombinant DNA, and immunology.

It is to be understood that as used herein and in the appended claims, the singular forms "a," "an," and "the," include plural referents unless the context clearly indicates otherwise. Thus, for example, reference to "a cell" includes one or more of such different cells, and reference to "the method" includes reference to equivalent steps and methods known to those of ordinary skill in the art that could be modified or substituted for the methods described herein.

The term "cell" as used herein also refers to individual cells, cell lines, or cultures derived from such cells. A "culture" refers to a composition comprising isolated cells of the same or a different type.

As used herein, the phrase "totipotent stem cells" refer to cells having the ability to differentiate into all cells constituting an organism, such as cells that are produced from the fusion of an egg and sperm cell. Cells produced by the first few divisions of the fertilized egg can also be totipotent. These cells can differentiate into embryonic and extraembryonic cell types. Pluripotent stem cells, such as ES cells for example, can give rise to any fetal or adult cell type. However, alone they cannot develop into a fetal or adult animal because they lack the potential to develop extraembryonic tissue. Extraembryonic tissue is, in part, derived from extraembryonic endoderm and can be further classified into parietal endoderm (Reichert's membrane) and visceral endoderm (forms part of the yolk sac). Both parietal and visceral endoderm support developments of the embryo but do not themselves form embryonic structures. There also exist other extraembryonic tissue including extraembryonic mesoderm and extraembryonic ectoderm.

In some embodiments, a "pluripotent cell" is used as the starting material for differentiation to endoderm-lineage, or more particularly, to pancreatic endoderm type cells. As used herein, "pluripotency" or "pluripotent cells" or equivalents thereof refers to cells that are capable of both proliferation in cell culture and differentiation towards a variety of lineage-restricted cell populations that exhibit multipotent properties, for example, both pluripotent ES cells and induced pluripotent stem (iPS) cells can give rise to each of the three embryonic cell lineages. Pluripotent cells, however, may not be capable of producing an entire organism. That is, pluripotent cells are not totipotent.

In certain embodiments, the pluripotent cells used as starting material are stem cells, including hES cells, hEG cells, iPS cells, even parthenogenic cells and the like. As used herein, "embryonic" refers to a range of developmental stages of an organism beginning with a single zygote and ending with a multicellular structure that no longer comprises pluripotent or totipotent cells other than developed gametic cells. In addition to embryos derived by gamete fusion, the term "embryonic" refers to embryos derived by somatic cell nuclear transfer. Still in another embodiment, pluripotent cells are not derived or are not immediately derived from embryos, for example, iPS cells are derived from a non-pluripotent cell, e.g., a multipotent cell or terminally differentiated cell.

Human pluripotent stem cells can also be defined or characterized by the presence of several transcription factors and cell surface proteins including transcription factors Oct-4, Nanog, and Sox-2, which form the core regulatory complex ensuring the suppression of genes that lead to differentiation and the maintenance of pluripotency; and cell surface antigens, such as the glycolipids SSEA3, SSEA4 and the keratan sulfate antigens, Tra-1-60 and Tra-1-81.

As used herein, the phrase "induced pluripotent stem cells," or "iPS cells" or "iPSCs", refer to a type of pluripotent stem cell artificially prepared from a non-pluripotent cell, typically an adult somatic cell, or terminally differentiated cell, such as a fibroblast, a hematopoietic cell, a myocyte, a neuron, an epidermal cell, or the like, by inserting certain genes or gene products, referred to as reprogramming factors. See Takahashi et al., Cell 131:861-872 (2007); Wernig et al., Nature 448:318-324 (2007); Park et al., Nature 451:141-146 (2008), which are herein incorporated by reference in their entireties. Induced pluripotent stem cells are substantially similar to natural human pluripotent stem cells, such as hES cells, in many respects including, the expression of certain stem cell genes and proteins, chromatin methylation patterns, doubling time, embryoid body formation, teratoma formation, viable chimera formation, and potency and differentiability. Human iPS cells provide a source of pluripotent stem cells without the associated use of embryos.

Various methods can be employed to produce iPS cells, which are described herein in further detail below. However, all the methodologies employ certain reprogramming factors comprising expression cassettes encoding Sox-2, Oct-4, Nanog and optionally Lin-28, or expression cassettes encoding Sox-2, Oct-4, Klf4 and optionally c-myc, or expression cassettes encoding Sox-2, Oct-4, and optionally Esrrb. Nucleic acids encoding these reprogramming factors can be in the same expression cassette, different expression cassettes, the same reprogramming vector, or different reprogramming vectors. Oct-3/4 and certain members of the Sox gene family (Sox-1, Sox-2, Sox-3, and Sox-15) are crucial transcriptional regulators involved in the induction process whose absence makes induction impossible. Oct-3/4 (Pou5f1) is one of the family of octamer ("Oct") transcription factors, and plays an important role in maintaining pluripotency. For example, the absence of Oct-3/4 in normally Oct-3/4+ cells, such as blastomeres and embryonic stem cells, leads to spontaneous trophoblast differentiation; whereas the presence of Oct-3/4 gives rise to the pluripotency and differentiation potential of embryonic stem cells. Also, other genes in the "Oct" family, for example, Oct1 and Oct6, do not induce pluripotency, therefore this pluripotency induction process can be attributed to Oct-3/4. Another family of genes associated with maintaining pluripotency similar to Oct-3/4, is the Sox family. However, the Sox family is not exclusive to pluripotent cell types but is also associated with multipotent and unipotent stem cells. The Sox family has been found to work as well in the induction process. Initial studies by Takahashi et al., 2006 supra used Sox2. Since then, Sox1, Sox3, Sox15, and Sox18 genes have also generated iPS cells. Klf4 of the Klf family of genes (Klf-1, Klf2, Klf4, and Klf5) was initially identified by Yamanaka et al. 2006 supra as a factor for the generation of mouse iPS cells. Human iPS cells from S. Yamanaka were used herein to explore cell therapeutic applications of hIPS cells. However, Yu et al. 2007 supra reported that Klf4 was not required and in fact failed to produce human iPS cells. Other members of the Klf family are capable generating iPS cells, including Klf1, Klf2 and Klf5. Lastly, the Myc family (C-myc, L-myc, and N-myc), proto-oncogenes implicated in cancer; c-myc was a factor implicated in the generation of mouse and human iPS cells, but Yu et al. (2007 supra reported that c-myc was not required for generation of human iPS cells.

As used herein, "multipotency" or "multipotent cell" or equivalents thereof refers to a cell type that can give rise to a limited number of other particular cell types. That is, multipotent cells are committed to one or more embryonic cell fates, and thus, in contrast to pluripotent cells, cannot give rise to each of the three embryonic cell lineages as well as to extraembryonic cells. Multipotent somatic cells are more differentiated relative to pluripotent cells, but are not terminally differentiated. Pluripotent cells therefore have a higher potency than multipotent cells. Potency-determining factors that can reprogram somatic cells or used to generate iPS cells include, but are not limited to, factors such as Oct-4, Sox2, FoxD3, UTF1, Stella, Rex1, ZNF206, Sox15, Myb12, Lin28, Nanog, DPPA2, ESG1, Otx2 or combinations thereof.

As used herein, "ERBB receptor tyrosine kinase activating agent" includes, but is not limited to, at least 16 different EGF family ligands that bind ERBB receptors: EGF (epidermal growth factor), AG or AREG (Amphiregulin), and TGF-Alpha (Transforming Growth Factor-Alpha), Btc (Betacellulin), HBEGF (Heparin-Binding EGF), and Ereg (Epiregulin), Neuregulins (or Heregulins) such as Neuregulin-1, -2, -3 and -4 (or Heregulin-1, -2, -3 and -4). However, the instant invention contemplates any ligand that is capable of binding to any one of the four ERBB receptors or a combination thereof to induce formation of homo- and heterodimer receptor complexes leading to activation of the intrinsic kinase domain and subsequent phosphorylation. See also Table 11.

Some embodiments of the methods of producing insulin described herein can include treating an animal having diabetes, or controlling glucose concentration in the blood of an animal, by providing the animal with pancreatic endoderm cells that can mature in vivo into insulin producing cells that secrete insulin in response to glucose stimulation.

One aspect described herein includes populations of pluripotent or precursor cells that are capable of selectively, and in some aspects selectively reversibly, developing into different cellular lineages when cultured under appropriate conditions. As used herein, the term "population" refers to cell culture of more than one cell having the same identifying characteristics. The term "cell lineage" refers to all of the stages of the development of a cell type, from the earliest precursor cell to a completely mature cell (i.e. a specialized cell). A "precursor cell" or "progenitor cell" can be any cell in a cell differentiation pathway that is capable of differentiating into a more mature cell. As such, a precursor cell can be a pluripotent cell, or it can be a partially differentiated multipotent cell, or reversibly differentiated cell. The term "precursor cell population" refers to a group of cells capable of developing into a more mature or differentiated cell type. A precursor cell population can comprise cells that are pluripotent, cells that are stem cell lineage restricted (i.e. cells capable of developing into less than all ectodermal lineages, or into, for example, only cells of neuronal lineage), and cells that are reversibly stem cell lineage restricted. Therefore, the term "progenitor cell" or "precursor cell" may be a "pluripotent cell" or "multipotent cell."

As used herein, the term "reprogramming", "reprogrammed" or equivalents thereof, refers to a process that confers on a cell a measurably increased capacity to form progeny of at least one new cell type, either in culture or in vivo, than it would have under the same conditions without reprogramming. In certain embodiments described herein, somatic cells are "reprogrammed" to pluripotent cells. In certain aspects, somatic cells are reprogrammed when after sufficient proliferation, a measurable proportion of cells, either in vivo or in an in vitro cell culture, display phenotypic characteristics of the new pluripotent cell type. Without reprogramming, such somatic cells would not give rise to progeny displaying phenotypic characteristics of the new pluripotent cell type. If, even without reprogramming, somatic cells could give rise to progeny displaying phenotypic characteristics of the new pluripotent cell type, the proportion of progeny from these somatic cells displaying phenotypic characteristics of the new pluripotent cell type is measurably more than before reprogramming.

As used herein, the phrase "differentiation programming" refers to a process that changes a cell to form progeny of at least one new cell type with a new differentiation status, either in culture or in vivo, than it would have under the same conditions without differentiation reprogramming. This process includes differentiation, dedifferentiation and transdifferentiation. Hence, as used herein, the phrase "differentiation" refers to the process by which a less specialized cell becomes a more specialized cell type. In contrast, the phrase "dedifferentiation" refers to a cellular process in which a partially or terminally differentiated cell reverts to an earlier developmental stage, such as cell having pluripotency or multipotency. In further contrast, the phrase "transdifferentiation" refers to a process of transforming one differentiated cell type into another differentiated cell type.

As used herein, the terms "develop from pluripotent cells", "differentiate from pluripotent cells", "mature from pluripotent cells" or "produced from pluripotent cells", "derived from pluripotent cells", "differentiated from pluripotent cells" and equivalent expressions refer to the production of a differentiated cell type from pluripotent cells in vitro or in vivo, e.g., in the case of endocrine cells matured from transplanted PDX1 pancreatic endoderm cells in vivo as described in International Patent Application No. PCT/US2007/015536, entitled METHODS OF PRODUCING PANCREATIC HORMONES, the disclosure of which is incorporated herein by reference in its entirety. All such terms refer to the progression of a cell from the stage of having the potential to differentiate into at least two different cellular lineages to becoming a specialized and terminally differentiated cell. Such terms can be used interchangeably for the purposes of the present application. Embodiments described herein contemplate culture conditions that permit such differentiation to be reversible, such that pluripotency or at least the ability to differentiate into more than one cellular lineage can be selectively regained.

The term "feeder cell" refers to a culture of cells that grows in vitro and secretes at least one factor into the culture medium, and that can be used to support the growth of another cell of interest in culture. As used herein, a "feeder cell layer" can be used interchangeably with the term "feeder cell." A feeder cell can comprise a monolayer, where the feeder cells cover the surface of the culture dish with a complete layer before growing on top of each other, or can comprise clusters of cells. In a preferred embodiment, the feeder cell comprises an adherent monolayer.

As used herein, the terms "cluster" and "clump" or "aggregate" can be used interchangeably, and generally refer to a group of cells that have not been dissociated into single cells. The clusters may be dissociated into smaller clusters. This dissociation is typically manual in nature (such as using a Pasteur pipette), but other means of dissociation are contemplated. Aggregate suspension pluripotent or multipotent cell cultures are substantially as described in International Publications PCT/US2007/062755, titled COMPOSITIONS AND METHODS FOR CULTURING DIFFERENTIAL CELLS and PCT/US2008/082356, titled STEM CELL AGGREGATE SUSPENSION COMPOSITIONS AND METHODS OF DIFFERENTIATION THEREOF, which are herein incorporated by reference in their entireties.

Similarly, embodiments in which pluripotent cell cultures or aggregate pluripotent suspension cultures are grown in defined conditions without the use of feeder cells, are "feeder-free". Feeder-free culture methods increase scalability and reproducibility of pluripotent cell culture and reduces the risk of contamination, for example, by infectious agents from the feeder cells or other animal-sourced culture components. Feeder-free methods are also described in U.S. Pat. No. 6,800,480 to Bodnar et al. (assigned to Geron Corporation, Menlo Park, Calif.). However, and in contrast to U.S. Pat. No. 6,800,480 patent, embodiments described herein, whether they be pluripotent, multipotent or differentiated cell cultures, are feeder-free and do not further contain an endogenous or exogenous extracellular-matrix; i.e. the cultures described herein are extracellular-matrix-free as well as being feeder free. For example, in the U.S. Pat. No. 6,800,480, extracellular matrix is prepared by culturing fibroblasts, lysing the fibroblasts in situ, and then washing what remains after lysis. Alternatively, in U.S. Pat. No. 6,800,480 extracellular matrix can also be prepared from an isolated matrix component or a combination of components selected from collagen, placental matrix, fibronectin, laminin, merosin, tenascin, heparin sulfate, chondroitin sulfate, dermatan sulfate, aggrecan, biglycan, thrombospondin, vitronectin, and decorin. Embodiments described herein neither produce an extracellular-matrix by growth of a feeder or fibroblast layer and lysing the cells to produce the extracellular-matrix; nor does it require first coating the tissue culture vessel with extracellular matrix component or a combination of extracellular-matrix components selected from collagen, placental matrix, fibronectin, laminin, merosin, tenascin, heparin sulfate, chondroitin sulfate, dermatan sulfate, aggrecan, biglycan, thrombospondin, vitronectin, and decorin. Hence, the aggregate suspension cultures described herein for pluripotent, multipotent and differentiated cells do not require a feeder layer, a lysed feeder or fibroblast cell to produce an extracellular matrix coating, an exogenously added extracellular matrix or matrix component; rather use of soluble human serum component as described in International Application PCT/US2008/080516, titled METHODS AND COMPOSITIONS FOR FEEDER-FREE PLURIPOTENT STEM CELL MEDIA CONTAINING HUMAN SERUM, which is herein incorporated by reference in its entirety, overcomes the need for either a feeder-cell or feeder monolayer, as well as overcoming the need for an endogenous extracellular-matrix from a feeder or fibroblast cell or from exogenously added extracellular-matrix components.

In preferred embodiments, culturing methods are free of animal-sourced products. In another preferred embodiment, the culturing methods are xeno-free. In even more preferred embodiments, one or more conditions or requirements for the commercial manufacture of human cell therapeutics met or exceeded by the culturing methods described herein.

The population of pluripotent cells can be further cultured in the presence of certain supplemental growth factors to obtain a population of cells that are or will develop into different cellular lineages, or can be selectively reversed in order to be able to develop into different cellular lineages. The term "supplemental growth factor" is used in its broadest context and refers to a substance that is effective to promote the growth of a pluripotent cell, maintain the survival of a cell, stimulate the differentiation of a cell, and/or stimulate reversal of the differentiation of a cell. Further, a supplemental growth factor may be a substance that is secreted by a feeder cell into its media. Such substances include, but are not limited to, cytokines, chemokines, small molecules, neutralizing antibodies, and proteins. Growth factors may also include intercellular signaling polypeptides, which control the development and maintenance of cells as well as the form and function of tissues. In preferred embodiments, the supplemental growth factor is selected from the group consisting of steel cell factor (SCF), oncostatin M (OSM), ciliary neurotrophic factor (CNTF), Interleukin-6 (IL-6) in combination with soluble Interleukin-6 Receptor (IL-6R), a fibroblast growth factor (FGF), a bone morphogenetic protein (BMP), tumor necrosis factor (TNF), and granulocyte macrophage colony stimulating factor (GM-CSF).

In certain processes for producing the cells as described herein, the growth factors are removed from the cell culture or cell population subsequent to their addition. For example, the growth factor, such as Activin A, Activin B, GDF-8, or GDF-11 can be added and removed within about one day, about two days, about three days, about four days, about five days, about six days, about seven days, about eight days, about nine days or about ten days after their addition. In some embodiments, the differentiation factors are not removed from the cell culture.

Because the efficiency of the differentiation process can be adjusted by modifying certain parameters, which include but are not limited to, cell growth conditions, growth factor concentrations and the timing of culture steps, the differentiation procedures described herein can result in about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or greater than about 95% conversion of pluripotent cells, which includes induced pluripotent cells, to multipotent or differentiated cells e.g., definitive endoderm, foregut endoderm, PDX1-positive foregut endoderm, PDX1-positive pancreatic endoderm or PDX1/NKX6.1 co-positive pancreatic endoderm, endocrine precursor or NGN3/NKX2.2 co-positive endocrine precursor, and hormone secreting endocrine cells or INS, GCG, GHRL, SST, PP singly-positive endocrine cells. In processes in which isolation of preprimitive streak or mesendoderm cells is employed, a substantially pure preprimitive streak or mesendoderm cell population can be recovered.

Various cell compositions derived from pluripotent stem cells are described herein. One embodiment includes iPS cells and cells derived therefrom. Still other processes and compositions related to but distinct from the embodiments described herein can be found in U.S. Provisional Patent Application No. 60/532,004, entitled DEFINITIVE ENDODERM, filed Dec. 23, 2003; U.S. Provisional Patent Application No. 60/566,293, entitled PDX1 EXPRESSING ENDODERM, filed Apr. 27, 2004; U.S. Provisional Patent Application No. 60/586,566, entitled CHEMOKINE CELL SURFACE RECEPTOR FOR THE ISOLATION OF DEFINITIVE ENDODERM, filed Jul. 9, 2004; U.S. Provisional Patent Application No. 60/587,942, entitled CHEMOKINE CELL SURFACE RECEPTOR FOR THE ISOLATION OF DEFINITIVE ENDODERM, filed Jul. 14, 2004; U.S. patent application Ser. No. 11/021,618, entitled DEFINITIVE ENDODERM, filed Dec. 23, 2004 and U.S. patent application Ser. No. 11/115,868, entitled PDX1 EXPRESSING ENDODERM, filed Apr. 26, 2005; U.S. patent application Ser. No. 11/165,305, entitled METHODS FOR IDENTIFYING FACTORS FOR DIFFERENTIATING DEFINITIVE ENDODERM, filed Jun. 23, 2005; U.S. Provisional Patent Application No. 60/730,917, entitled PDX1-EXPRESSING DORSAL AND VENTRAL FOREGUT ENDODERM, filed Oct. 27, 2005; U.S. Provisional Patent Application No. 60/736,598, entitled MARKERS OF DEFINITIVE ENDODERM, filed Nov. 14, 2005; U.S. Provisional Patent Application No. 60/778,649, entitled INSULIN-PRODUCING CELLS AND METHOD OF PRODUCTION, filed Mar. 2, 2006; U.S. Provisional Patent Application No. 60/833,633, entitled INSULIN-PRODUCING CELLS AND METHOD OF PRODUCTION, filed Jul. 26, 2006; U.S. Provisional Patent Application No. 60/852,878, entitled ENRICHMENT OF ENDOCRINE PRECURSOR CELLS, IMMATURE PANCREATIC ISLET CELLS AND MATURE PANCREATIC ISLET CELLS USING NCAM, filed Oct. 18, 2006; U.S. patent application Ser. No. 11/588,693, entitled PDX1-EXPRESSING DORSAL AND VENTRAL FOREGUT ENDODERM, filed Oct. 27, 2006; U.S. patent application Ser. No. 11/681,687, entitled ENDOCRINE PRECURSOR CELLS, PANCREATIC HORMONE-EXPRESSING CELLS AND METHODS OF PRODUCTION, filed Mar. 2, 2007; U.S. patent application Ser. No. 11/773,944, entitled METHODS OF PRODUCING PANCREATIC HORMONES, filed Jul. 5, 2007; U.S. Patent Application No. 60/972,174, entitled METHODS OF TREATMENT FOR DIABETES, filed Sep. 13, 2007; U.S. patent application Ser. No. 11/860,494, entitled METHODS FOR INCREASING DEFINITIVE ENDODERM PRODUCTION, filed Sep. 24, 2007; U.S. Patent Application No. 60/977,349, entitled CELL SURFACE MARKERS OF HUMAN EMBRYONIC STEM CELLS AND CANCER STEM CELLS, filed Oct. 3, 2007; and U.S. patent application Ser. No. 12/099,759, entitled METHODS OF PRODUCING PANCREATIC HORMONES, filed Apr. 8, 2008; and U.S. patent application Ser. No. 12/107,020, entitled METHODS FOR PURIFYING ENDODERM AND PANCREATIC ENDODERM CELLS DERIVED FORM HUMAN EMBRYONIC STEM CELLS, filed Apr. 21, 2008 the disclosures of which are incorporated herein by reference in their entireties.

General methods for production of endoderm lineage cells derived from hES cells are described in related U.S. applications as indicated above, and D'Amour et al. 2005 Nat Biotechnol. 23:1534-41 and D'Amour et al. 2006 Nat Biotechnol. 24(11):1392-401 the disclosures of which are incorporated herein by reference in their entireties. D'Amour et al. describe a 5 step differentiation protocol: stage 1 (results in mostly definitive endoderm production), stage 2 (results in mostly PDX1-negative foregut endoderm production), stage 3 (results in mostly PDX1-positive foregut endoderm production), stage 4 (results in mostly pancreatic endoderm or pancreatic endocrine progenitor production) and stage 5 (results in mostly hormone expressing endocrine cell production.

The term "trophectoderm" refers to a multipotent cell having the relative high expression of markers selected from the group consisting of HAND1, Eomes, MASH2, ESXL1, HCG, KRT18, PSG3, SFXN5, DLX3, PSX1, ETS2, and ERRB genes as compared to the expression levels of HAND1, Eomes, MASH2, ESXL1, HCG, KRT18, PSG3, SFXN5, DLX3, PSX1, ETS2, and ERRB in non-trophectoderm cells or cell populations.

"Extraembryonic endoderm" refers to a multipotent cell having relative high expression levels of markers selected from the group consisting of SOX7, SOX17, THBD, SPARC, DAB1, or AFP genes as compared to the expression levels of SOX7, SOX17, THBD, SPARC, DAB1, or AFP in non-extraembryonic endoderm cells or cell populations.

The term "Preprimitive streak cells" refers to a multipotent cell having relative high expression levels of the FGF8 and/or NODAL marker genes, as compared to BRACHURY low, FGF4 low, SNAI1 low, SOX17 low, FOXA2 low, SOX7 low and SOX1 low.

The term "Mesendoderm cell" refers to a multipotent cell having relative high expression levels of brachyury, FGF4, SNAI1 MIXL1 and/or WNT3 marker genes, as compared to SOX17 low, CXCR4 low, FOXA2 low, SOX7 low and SOX1 low.

The term "Definitive endoderm (DE)" refers to a multipotent endoderm lineage cell that can differentiate into cells of the gut tube or organs derived from the gut tube. In accordance with certain embodiments, the definitive endoderm cells are mammalian cells, and in a preferred embodiment, the definitive endoderm cells are human cells. In some embodiments of the present invention, definitive endoderm cells express or fail to significantly express certain markers. In some embodiments, one or more markers selected from SOX17, CXCR4, MIXL1, GATA4, HNF3β, GSC, FGF17, VWF, CALCR, FOXQ1, CMKOR1 and CRIP1 are expressed in definitive endoderm cells. In other embodiments, one or more markers selected from OCT4, alpha-fetoprotein (AFP), Thrombomodulin (TM), SPARC, SOX7 and HNF4alpha are not expressed or significantly expressed in definitive endoderm cells. Definitive endoderm cell populations and methods of production thereof are also described in U.S. application Ser. No. 11/021,618, entitled DEFINITIVE ENDODERM, filed Dec. 23, 2004, which is hereby incorporated in its entirety.

Still other embodiments relate to cell cultures termed "PDX1-negative foregut endoderm cells" or "foregut endoderm cells" or equivalents thereof. In some embodiments, the foregut endoderm cells express SOX17, HNF1β (HNF1B), HNF4alpha (HNF4A) and FOXA1 markers but do not substantially express PDX1, AFP, SOX7, or SOX1. PDX1-negative foregut endoderm cell populations and methods of production thereof are also described in U.S. application Ser. No. 11/588,693, entitled PDX1-expressing dorsal and ventral foregut endoderm, filed Oct. 27, 2006 which is incorporated herein by reference in its entirety.

Other embodiments described herein relate to cell cultures of "PDX1-positive, dorsally-biased, foregut endoderm cells" (dorsal PDX1-positive foregut endoderm cells) or just "PDX1-positive endoderm." In some embodiments, the PDX1-positive endoderm cells express one or more markers selected from Table 1 and/or one or more markers selected from Table 2, also described in related U.S. application Ser. No. 11/588,693 entitled PDX1 EXPRESSING DOSAL AND VENTRAL FOREGUT ENDODERM, filed Oct. 27, 2006, and also U.S. application Ser. No. 11/115,868, entitled PDX1-expressing endoderm, filed Apr. 26, 2005, which are incorporated herein by reference in their entireties.

TABLE 1

Markers expressed in both dorsal and ventral PDX1-positive foregut endoderm

| Gene_Symbol | Unigene | LocusLink | OMIM | SeqDerivedFrom | Gene Descriptor |
|---|---|---|---|---|---|
| ANXA4 | Hs.422986 | 307 | 106491 | NM_001153 | annexin A4 |
| ASCL1 | Hs.524672 | 429 | 100790 | BC001638 | achaete-scute complex-like 1 (*Drosophila*) |
| BNC1 | Hs.459153 | 646 | 601930 | NM_001717 | basonuclin 1 |
| C10orf30 | Hs.498740 | 222389 | | AW195407 | Chromosome 10 open reading frame 30 |
| C2orf23 | Hs.368884 | 65055 | 609139 | BE535746 | chromosome 2 open reading frame 23 |
| C9orf150 | Hs.445356 | 286343 | | AI972386 | chromosome 9 open reading frame 150 |
| CDH6 | Hs.171054 | 1004 | 603007 | BC000019 | cadherin 6, type 2, K-cadherin (fetal kidney) |
| DACH1 | Hs.129452 | 1602 | 603803 | AI650353 | dachshund homolog 1 (*Drosophila*) |
| DUSP9 | Hs.144879 | 1852 | 300134 | NM_001395 | dual specificity phosphatase 9 |
| ELMOD1 | Hs.495779 | 55531 | | AL359601 | ELMO domain containing 1 |
| FLJ21462 fis | Hs.24321 | | | AW236803 | CDNA clone IMAGE: 5273964, partial cds |
| FLJ22761 | Hs.522988 | 80201 | | W81116 | hypothetical protein FLJ22761 |
| GABRA2 | Hs.116250 | 2555 | 137140 | NM_000807 | gamma-aminobutyric acid (GABA) A receptor, alpha 2 |
| GRIA3 | Hs.377070 | 2892 | 305915 | BC032004 | glutamate receptor, ionotropic, AMPA 3 |
| HNF4G | Hs.241529 | 3174 | 605966 | AI916600 | hepatocyte nuclear factor 4, gamma |
| IDH2 | Hs.513141 | 3418 | 147650 | U52144 | isocitrate dehydrogenase 2 (NADP+), mitochondrial |
| IL6R | Hs.135087 | 3570 | 147880 | AV700030 | interleukin 6 receptor |
| KCNJ2 | Hs.1547 | 3759 | 170390 | AF153820 | potassium inwardly-rectifying channel, subfamily J, member 2 |
| KLF3 | Hs.298658 | 51274 | | AA130132 | Kruppel-like factor 3 (basic) |
| LGALS3 | Hs.531081 | 3958 | 153619 | AW085690 | Lectin, galactoside-binding, soluble, 3 (galectin 3) |
| LGALS3 /// GALIG | Hs.531081 | 3958/// | 153619 | BC001120 | lectin, galactoside-binding, soluble, 3 (galectin 3) /// galectin-3 internal gene |
| LIPC | Hs.188630 | 3990 | 151670 | NM_000236 | lipase, hepatic |
| MEIS1 | Hs.526754 | 4211 | 601739 | NM_002398 | Meis1, myeloid ecotropic viral integration site 1 homolog (mouse) |
| NR2F1 | Hs.519445 | 7025 | 132890 | AI951185 | Nuclear receptor subfamily 2, group F, member 1 |
| ONECUT2 | Hs.194725 | 9480 | 604894 | NM_004852 | one cut domain, family member 2 |
| PAPPA | Hs.494928 | 5069 | 176385 | AA148534 | pregnancy-associated plasma protein A, pappalysin 1 |
| PDE3B | Hs.445711 | 5140 | 602047 | NM_000753 | phosphodiesterase 3B, cGMP-inhibited |
| PGPEP1 | Hs.131776 | 54858 | | NM_017712 | pyroglutamyl-peptidase I |
| PMS2L1 | Hs.520575 | 5379 | 605038 | D38503 | postmeiotic segregation increased 2-like 1 |
| SERPINF2 | Hs.159509 | 5345 | 262850 | NM_000934 | serine (or cysteine) proteinase inhibitor, clade F (alpha-2 antiplasmin, pigment epithelium derived factor), member 2 |
| SLC27A2 | Hs.11729 | 11001 | 603247 | NM_003645 | solute carrier family 27 (fatty acid transporter), member 2 |
| SLN | Hs.334629 | 6588 | 602203 | NM_003063 | Sarcolipin |
| SOX9 | Hs.2316 | 6662 | 114290 | NM_000346 | SRY (sex determining region Y)-box 9 (campomelic dysplasia, autosomal sex-reversal) |
| SULT2A1 | Hs.515835 | 6822 | 125263 | U08024 | sulfotransferase family, cytosolic, 2A, dehydroepiandrosterone (DHEA)-preferring, member 1 |
| TFPI | Hs.516578 | 7035 | 152310 | BF511231 | Tissue factor pathway inhibitor (lipoprotein-associated coagulation inhibitor) |
| ZHX1 | Hs.521264 | 11244 | 604764 | AI123518 | zinc fingers and homeoboxes 1 |
| ZNF467 | Hs.112158 | 168544 | | BE549732 | zinc finger protein 467 |
| ZNF503 | Hs.195710 | 84858 | | AA603467 | zinc finger protein 503 |
| | Hs.142869 | | | AI935586 | Transcribed locus |

TABLE 2

Markers expressed in dorsally-biased PDX1-positive foregut endoderm

| Gene_Symbol | Unigene | LocusLink | OMIM | SeqDerivedFrom | Gene Descriptor |
|---|---|---|---|---|---|
| ADORA2A | Hs.197029 | 135 | 102776 | NM_000675 | adenosine A2a receptor |
| AMSH-LP | Hs.16229 | 57559 | | AI638611 | associated molecule with the SH3 domain of STAM (AMSH) like protein |
| BAIAP2L1 | Hs.489237 | 55971 | | AA628400 | BAI1-associated protein 2-like 1 |
| CD47 | Hs.446414 | 961 | 601028 | BG230614 | CD47 antigen (Rh-related antigen, integrin-associated signal transducer) |
| CHN2 | Hs.203663 | 1124 | 602857 | AK026415 | Chimerin (chimaerin) 2 |
| CLDN3 | Hs.25640 | 1365 | 602910 | BE791251 | claudin 3 |
| CPVL | Hs.233389 | 54504 | | NM_031311 | carboxypeptidase, vitellogenic-like /// carboxypeptidase, vitellogenic-like |
| CREB3L1 | Hs.405961 | 90993 | | AF055009 | cAMP responsive element binding protein 3-like 1 |
| DACT1 | Hs.48950 | 51339 | 607861 | NM_016651 | dapper homolog 1, antagonist of β-catenin (*xenopus*) |
| DPP6 | Hs.490684 | 1804 | 126141 | AW071705 | Dipeptidylpeptidase 6 |
| ELF3 | Hs.67928 | 1999 | 602191 | AF017307 | E74-like factor 3 (ets domain transcription factor, epithelial-specific) |
| ENPP2 | Hs.190977 | 5168 | 601060 | L35594 | ectonucleotide pyrophosphatase/phosphodiesterase 2 (autotaxin) |
| EPB41L1 | Hs.437422 | 2036 | 602879 | AA912711 | erythrocyte membrane protein band 4.1-like 1 |
| FAM46C | Hs.356216 | 54855 | | AL046017 | family with sequence similarity 46, member C |
| FAM49A | Hs.467769 | 81553 | | NM_030797 | family with sequence similarity 49, member A /// family with sequence similarity 49, member A |
| FLJ30596 | Hs.81907 | 133686 | | AI453203 | hypothetical protein FLJ30596 |
| HOXA1 | Hs.67397 | 3198 | 142955 | S79910 | homeo box A1 |
| HOXA3 | Hs.533357 | 3200 | 142954 | AW137982 | homeo box A3 |
| HOXB2 | Hs.514289 | 3212 | 142967 | NM_002145 | homeo box B2 |
| LAF4 | Hs.444414 | 3899 | 601464 | AW085505 | Lymphoid nuclear protein related to AF4 |
| LOC283658 | Hs.87194 | 283658 | | AA233912 | hypothetical protein LOC283658 |

TABLE 2-continued

Markers expressed in dorsally-biased PDX1-positive foregut endoderm

| Gene_Symbol | Unigene | LocusLink | OMIM | SeqDerivedFrom | Gene Descriptor |
|---|---|---|---|---|---|
| MAF | Hs.134859 | 4094 | 177075 | AF055376 | v-maf musculoaponeurotic fibrosarcoma oncogene homolog (avian) |
| MAG | Hs.515354 | 4099 | 159460 | X98405 | myelin associated glycoprotein |
| MYCPBP | Hs.513817 | 10260 | 600382 | BE268538 | c-myc promoter binding protein |
| NR4A2 | Hs.165258 | 4929 | 168600/ | NM_006186 | nuclear receptor subfamily 4, group A, member 2 |
| NRXN3 | Hs.368307 | 9369 | 600567 | AI129949 | neurexin 3 |
| NSE1 | Hs.260855 | 151354 | | AI601101 | NSE1 |
| PCGF5 | Hs.500512 | 84333 | | AL045882 | polycomb group ring finger 5 |
| PDE11A | Hs.130312 | 50940 | 604961 | AB038041 | phosphodiesterase 11A |
| PDE5A | Hs.370661 | 8654 | 603310 | BF221547 | Phosphodiesterase 5A, cGMP-specific |
| PGA3 | | 5220 | 169710 | AI570199 | pepsinogen 3, group I (pepsinogen A) |
| PLN | Hs.170839 | 5350 | 115200 | NM_002667 | Phospholamban |
| PTGIS | Hs.302085 | 5740 | 145500 | NM_000961 | prostaglandin I2 (prostacyclin) synthase /// prostaglandin I2 (prostacyclin) synthase |
| RARB | Hs.436538 | 5915 | 180220 | NM_000965 | retinoic acid receptor, β |
| RGN | Hs.77854 | 9104 | 300212 | D31815 | regucalcin (senescence marker protein-30) |
| RND1 | Hs.124940 | 27289 | 609038 | U69563 | Rho family GTPase 1 |
| SFRP5 | Hs.279565 | 6425 | 604158 | NM_003015 | secreted frizzled-related protein 5 |
| SGKL | Hs.380877 | 23678 | 607591 | AV690866 | serum/glucocorticoid regulated kinase-like |
| SLC16A10 | Hs.520321 | 117247 | 607550 | N30257 | solute carrier family 16 (monocarboxylic acid transporters), member 10 |
| SLC16A2 | Hs.75317 | 6567 | 300095 | NM_006517 | solute carrier family 16 (monocarboxylic acid transporters), member 2 |
| SLC1A3 | Hs.481918 | 6507 | 600111 | NM_004172 | solute carrier family 1 (glial high affinity glutamate transporter), member 3 |
| SLC30A4 | Hs.162989 | 7782 | 602095 | NM_013309 | solute carrier family 30 (zinc transporter), member 4 |
| SLICK | Hs.420016 | 343450 | | AI732637 | sodium- and chloride-activated ATP-sensitive potassium channel |
| SLITRK4 | Hs.272284 | 139065 | | AL080239 | SLIT and NTRK-like family, member 4 |
| ST8SIA3 | Hs.298923 | 51046 | | NM_015879 | ST8 alpha-N-acetyl-neuraminide alpha-2,8-sialyltransferase 3 wingless-type MMTV integration site family, member 5A /// wingless-type |
| WNT5A | Hs.152213 | 7474 | 164975 | AI968085 | MMTV integration site family, member 5A |
| XPR1 | Hs.227656 | 9213 | 605237 | AF089744 | xenotropic and polytropic retrovirus receptor |
| | Hs.535688 | | | AK001582 | CDNA FLJ10720 fis, clone NT2RP3001116 |
| | Hs.127009 | | | AI935541 | Transcribed locus |
| | Hs.4749 | | | AL137310 | CDNA FLJ31660 fis, clone NT2RI2004410 |

The PDX1-positive foregut endoderm cells, such as those produced according to the methods described herein, are progenitors which can be used to produce fully differentiated pancreatic hormone secreting or endocrine cells, e.g., insulin-producing β-cells. In some embodiments of the present invention, PDX1-positive foregut endoderm cells are produced by differentiating definitive endoderm cells that do not substantially express PDX1 (PDX1-negative definitive endoderm cells; also referred to herein as definitive endoderm) so as to form PDX1-positive foregut endoderm cells.

As used herein, "pancreatic endoderm," "pancreatic epithelial," "pancreatic epithelium" (all can be abbreviated "PE") "pancreatic progenitor," "PDX-1 positive pancreatic endoderm or equivalents thereof, such as pancreatic endoderm cells ("PEC"), are all precursor or progenitor pancreatic cells. PEC as described herein is a progenitor cell population after stage 4 differentiation (about day 12-14) and includes at least two major distinct populations: i) pancreatic progenitor cells that express NKX6.1 but do not express CHGA (or CHGA negative, CHGA−); and ii) polyhormonal endocrine cells that express CHGA (CHGA positive, CHGA+). Without being bound by theory, the cell population that expresses NKX6.1 but not CHGA is hypothesized to be the more active or therapeutic component of PEC, whereas the population of CHGA-positive polyhormonal endocrine cells is hypothesized to further differentiate and mature in vivo into glucagon-expressing islet cells. See Kelly et al. (2011) Cell-surface markers for the isolation of pancreatic cell types derived from human embryonic stem cells, *Nat Biotechnol.* 29(8):750-756, published online 31 Jul. 2011 and Schulz et al. (2012), A Scalable System for Production of Functional Pancreatic Progenitors from Human Embryonic Stem Cells, PLosOne 7(5): 1-17, e37004, the disclosures of which are both incorporated herein by reference in there in their entireties.

Still, sometimes, pancreatic endoderm cells are used without reference to PEC as described just above, but to refer to at least stages 3 and 4 type cells in general. The use and meaning will be clear from the context. Pancreatic endoderm derived from pluripotent stem cells, and at least hES and hIPS cells, in this manner are distinguished from other endodermal lineage cell types based on differential or high levels of expression of markers selected from PDX1, NKX6.1, PTF1A, CPA1, cMYC, NGN3, PAX4, ARX and NKX2.2 markers, but do not substantially express genes which are hallmark of pancreatic endocrine cells, for example, CHGA, INS, GCG, GHRL, SST, MAFA, PCSK1 and GLUT1. Additionally, some "endocrine progenitor cells" expressing NGN3 can differentiate into other non-pancreatic structures (e.g., duodenum). In one embodiment, the NGN3 expressing endocrine progenitor described herein differentiates into mature pancreatic lineage cells, e.g., pancreatic endocrine cells. Pancreatic endoderm or endocrine progenitor cell populations and methods thereof are also described in U.S. patent application Ser. No. 11/773, 944, entitled Methods of producing pancreatic hormones, filed Jul. 5, 2007, and U.S. patent application Ser. No. 12/107, 020, entitled METHODS FOR PURIFYING ENDODERM AND PANCREATIC ENDODERM CELLS DERIVED FORM HUMAN EMBRYONIC STEM CELLS, filed Apr. 21, 2008, the disclosures of which are incorporated herein by reference in their entireties.

As used herein, "endocrine precursor cell" refers to a multipotent cell of the definitive endoderm lineage that expresses neurogenin 3 (NEUROG3) and which can further differentiate into cells of the endocrine system including, but not limited to, pancreatic islet hormone-expressing cells. Endocrine precursor cells cannot differentiate into as many different cell, tissue and/or organ types as compared to less specifically differentiated definitive endoderm lineage cells, such as PDX1-positive pancreatic endoderm cell.

As used herein, "pancreatic islet hormone-expressing cell," "pancreatic endocrine cell," or equivalents thereof refer to a cell, which has been derived from a pluripotent cell in vitro, which can be polyhormonal or singly-hormonal. The endocrine cells can therefore express one or more pancreatic hormones, which have at least some of the functions of a human pancreatic islet cell. Pancreatic islet hormone-expressing cells can be mature or immature. Immature pancreatic islet hormone-expressing cells can be distinguished from mature pancreatic islet hormone-expressing cells based on the differential expression of certain markers, or based on their functional capabilities, e.g., glucose responsiveness.

Many stem cell media culture or growth environments are envisioned in the embodiments described herein, including defined media, conditioned media, feeder-free media, serum-free media and the like. As used herein, the term "growth environment" or "milieu" or equivalents thereof is an environment in which undifferentiated or differentiated stem cells (e.g., primate embryonic stem cells) will proliferate in vitro. Features of the environment include the medium in which the cells are cultured, and a supporting structure (such as a substrate on a solid surface) if present. Methods for culturing or maintaining pluripotent cells and/or differentiating pluripotent cells are also described in PCT/US2007/062755 entitled COMPOSITIONS AND METHODS USEFUL FOR CULTURING DIFFERENTIABLE CELLS, filed Feb. 23, 2007; U.S. application Ser. No. 11/993,399, entitled EMBRYONIC STEM CELL CULTURE COMPOSITIONS AND METHODS OF USE THEREOF, filed Dec. 20, 2007; and U.S. application Ser. No. 11/875,057, entitled Methods and compositions for feeder-free pluripotent stem cell media containing human serum, filed Oct. 19, 2007, which are incorporated herein by reference in their entireties.

The term "essentially" or "substantially" means either a de minimus or a reduced amount of a component or cell present in any cell aggregate suspension type, e.g., cell aggregates in suspension described herein are "essentially or substantially homogenous", "essentially or substantially homo-cellular" or are comprised of "essentially hES cells", "essentially or substantially definitive endoderm cells", "essentially or substantially foregut endoderm cells", "essentially or substantially PDX1-negative foregut endoderm cells", "essentially or substantially PDX1-positive pre-pancreatic endoderm cells", "essentially or substantially PDX1-positive pancreatic endoderm or progenitor cells", "essentially or substantially PDX1-positive pancreatic endoderm tip cells", "essentially or substantially pancreatic endocrine precursor cells", "essentially or substantially pancreatic endocrine cells" and the like.

With respect to cells in cell cultures or in cell populations, the term "substantially free of" means that the specified cell type of which the cell culture or cell population is free, is present in an amount of less than about 10%, less than about 9%, less than about 8%, less than about 7%, less than about 6%, less than about 5%, less than about 4%, less than about 3%, less than about 2% or less than about 1% of the total number of cells present in the cell culture or cell population.

Cell cultures can be grown in medium containing reduced serum or substantially free of serum or no serum. Under certain culture conditions, serum concentrations can range from about 0% (v/v) to about 10% (v/v). For example, in some differentiation processes, the serum concentration of the medium can be less than about 0.05% (v/v), less than about 0.1% (v/v), less than about 0.2% (v/v), less than about 0.3% (v/v), less than about 0.4% (v/v), less than about 0.5% (v/v), less than about 0.6% (v/v), less than about 0.7% (v/v), less than about 0.8% (v/v), less than about 0.9% (v/v), less than about 1% (v/v), less than about 2% (v/v), less than about 3% (v/v), less than about 4% (v/v), less than about 5% (v/v), less than about 6% (v/v), less than about 7% (v/v), less than about 8% (v/v), less than about 9% (v/v) or less than about 10% (v/v). In some processes, preprimitive streak cells are grown without serum or without serum replacement. In still other processes, preprimitive streak cells are grown in the presence of B27. In such processes, the concentration of B27 supplement can range from about 0.1% (v/v) to about 20% (v/v).

In still other processes, immature pancreatic islet hormone-expressing cells are grown in the presence of B27. In such processes, the concentration of B27 supplement can range from about 0.1% (v/v) to about 20% (v/v) or in concentrations greater than about 20% (v/v). In certain processes, the concentration of B27 in the medium is about 0.1% (v/v), about 0.2% (v/v), about 0.3% (v/v), about 0.4% (v/v), about 0.5% (v/v), about 0.6% (v/v), about 0.7% (v/v), about 0.8% (v/v), about 0.9% (v/v), about 1% (v/v), about 2% (v/v), about 3% (v/v), about 4% (v/v), about 5% (v/v), about 6% (v/v), about 7% (v/v), about 8% (v/v), about 9% (v/v), about 10% (v/v), about 15% (v/v) or about 20% (v/v). Alternatively, the concentration of the added B27 supplement can be measured in terms of multiples of the strength of a commercially available B27 stock solution. For example, B27 is available from Invitrogen (Carlsbad, Calif.) as a 50× stock solution. Addition of a sufficient amount of this stock solution to a sufficient volume of growth medium produces a medium supplemented with the desired amount of B27. For example, the addition of 10 ml of 50×B27 stock solution to 90 ml of growth medium would produce a growth medium supplemented with 5×B27. The concentration of B27 supplement in the medium can be about 0.1×, about 0.2×, about 0.3×, about 0.4×, about 0.5×, about 0.6×, about 0.7×, about 0.8×, about 0.9×, about 1×, about 1.1×, about 1.2×, about 1.3×, about 1.4×, about 1.5×, about 1.6×, about 1.7×, about 1.8×, about 1.9×, about 2×, about 2.5×, about 3×, about 3.5×, about 4×, about 4.5×, about 5×, about 6×, about 7×, about 8×, about 9×, about 10×, about 11×, about 12×, about 13×, about 14×, about 15×, about 16×, about 17×, about 18×, about 19×, about 20× and greater than about 20×.

As used herein, "exogenously added," compounds such as growth factors, differentiation factors, and the like, in the context of cultures or conditioned media, refers to growth factors that are added to the cultures or media to supplement any compounds or growth factors that may already be present in the culture or media. For example, in some embodiments, cells cultures and or cell populations do not include an exogenously-added retinoid.

As used herein, "retinoid" refers to retinol, retinal or retinoic acid as well as derivatives of any of these compounds. In a preferred embodiment, the retinoid is retinoic acid.

By "FGF family growth factor," "a fibroblast growth factor" or "member of the fibroblast growth factor family" is meant an FGF selected from the group consisting of FGF1, FGF2, FGF3, FGF4, FGF5, FGF6, FGF7, FGF8, FGF9, FGF10, FGF11, FGF12, FGF13, FGF14, FGF15, FGF16, FGF17, FGF18, FGF19, FGF20, FGF21, FGF22 and FGF23. In some embodiments, "FGF family growth factor," "a fibroblast growth factor" or "member of the fibroblast growth factor family" means any growth factor having homology and/or function similar to a known member of the fibroblast growth factor family.

As used herein, "expression" refers to the production of a material or substance as well as the level or amount of production of a material or substance. Thus, determining the expression of a specific marker refers to detecting either the relative or absolute amount of the marker that is expressed or simply detecting the presence or absence of the marker.

As used herein, "marker" refers to any molecule that can be observed or detected. For example, a marker can include, but is not limited to, a nucleic acid, such as a transcript of a specific gene, a polypeptide product of a gene, a non-gene product polypeptide, a glycoprotein, a carbohydrate, a glycolipid, a lipid, a lipoprotein or a small molecule (for example, molecules having a molecular weight of less than 10,000 amu).

For most markers described herein, the official Human Genome Organization (HUGO) gene symbol is provided. Such symbols, which are developed by the HUGO Gene Nomenclature Committee, provide unique abbreviations for each of the named human genes and gene products. These gene symbols are readily recognized and can easily be associated with a corresponding unique human gene and/or protein sequence by those of ordinary skill in the art.

In accordance with the HUGO designations, the following gene symbols are defined as follows: GHRL—ghrelin; IAPP—islet amyloid polypeptide; INS—insulin; GCG—glucagon; ISL1—ISL1 transcription factor; PAX6—paired box gene 6; PAX4—paired box gene 4; NEUROG3—neurogenin 3 (NGN3); NKX2-2—NKX2 transcription factor related, locus 2 (NKX2.2); NKX6-1—NKX6 transcription factor related, locus 1 (NKX6.1); IPF1—insulin promoter factor 1 (PDX1); ONECUT1—one cut domain, family member 1 (HNF6); HLXB9—homeobox B9 (HB9); TCF2—transcription factor 2, hepatic (HNF1b); FOXA1—forkhead box A1; HGF—hepatocyte growth factor; IGF1—insulin-like growth factor 1; POU5F1—POU domain, class 5, transcription factor 1 (OCT4); NANOG—Nanog homeobox; SOX2—SRY (sex determining region Y)-box 2; CDH1—cadherin 1, type 1, E-cadherin (ECAD); T—brachyury homolog (BRACH); FGF4—fibroblast growth factor 4; WNT3—wingless-type MMTV integration site family, member 3; SOX17—SRY (sex determining region Y)-box 17; GSC—goosecoid; CER1—(cerberus 1, cysteine knot superfamily, homolog (CER); CXCR4—chemokine (C—X—C motif) receptor 4; FGF17—fibroblast growth factor 17; FOXA2—forkhead box A2; SOX7—SRY (sex determining region Y)-box 7; SOX1—SRY (sex determining region Y)-box 1; AFP—alpha-fetoprotein; SPARC—secreted protein, acidic, cysteine-rich (osteonectin); and THBD—thrombomodulin (TM), NCAM—neural cell adhesion molecule; SYP—synaptophysin; ZIC1—Zic family member 1; NEF3—neurofilament 3 (NFM); SST—somatostatin; MAFA—v-maf musculoaponeurotic fibrosarcoma oncogene homolog A; MAFB—v-maf musculoaponeurotic fibrosarcoma oncogene homolog B; SYP—synaptophysin; CHGA—chromogranin A (parathyroid secretory protein 1).

The following provides the full gene names corresponding to non-HUGO gene symbols as well as other abbreviations that may be used herein: SS—somatostatin (SOM); PP—pancreatic polypeptide; C-peptide—connecting peptide; Ex4—exendin 4; NIC—nicotinamide and DAPT—N—[N-(3,5-difluorophenacetyl)-L-alanyl]-S-phenylglycine t-butyl ester; RA—retinoic acid; RPMI—Roswell Park Memorial Institute medium; CMRL—Connaught Medical Research Labs medium; FBS—fetal bovine serum; NBP10—NCAM binding protein 10; PTF1a—pancreas specific transcription factor 1a.

The progression of pluripotent cells to various multipotent and/or differentiated cells can be monitored by determining the relative expression of genes, or gene markers, characteristic of a specific cell, as compared to the expression of a second or control gene, e.g., housekeeping genes. In some processes, the expression of certain markers is determined by detecting the presence or absence of the marker. Alternatively, the expression of certain markers can be determined by measuring the level at which the marker is present in the cells of the cell culture or cell population. In such processes, the measurement of marker expression can be qualitative or quantitative. One method of quantitating the expression of markers that are produced by marker genes is through the use of quantitative PCR (Q-PCR). Methods of performing Q-PCR are well known in the art. Other methods which are known in the art can also be used to quantitate marker gene expression. For example, the expression of a marker gene product can be detected by using antibodies specific for the marker gene product of interest.

In some processes, the higher expression of the following genes are indicative of certain populations of cells, for example: SOX17, SOX7, AFP or THBD are indicative of extraembryonic endoderm; NODAL and/or FGF8 are indicative of preprimitive streak; brachyury, FGF4, SNAI1 and/or WNT3 are indicative of mesendoderm; CER, GSC, CXCR4, SOX17 and FOXA2 are indicative of definitive endoderm cells; SOX17, FOXA2, FOXA1, HNF1B and HNF4A are indicative of foregut endoderm (or PDX1-negative endoderm); PDX1, HNF6, SOX9 and PROX1 are indicative PDX1-positive endoderm; PDX1, NKX6.1, PTFA1, CPA and cMYC are indicative of pancreatic epithelium (PE or pancreatic progenitor); NGN3, PAX4, ARX and NKX2.2 are indicate of endocrine precursor cells; and INS, GCG, GHRL, SST and PP are indicative of the various endocrine cells; relative high MAFA to MAFB gene expression is indicative of insulin secreting endocrine cell; and relative high expression of MAFB to MAFA gene expression is indicative of glucagon secreting endocrine cells.

The terms fibroblast growth factor 7 (FGF7) and keratinocyte growth factor (KGF) are synonymous.

Methods for Production of Induced Pluripotent Stem (iPS) Cells

Embodiments described herein are not limited to any one type of iPS cell or any one method of producing the iPS cell. Embodiments are not limited or dependent on levels of efficiency of production of the iPS cells, because various methods exist. Embodiments described herein apply to differentiation of iPS cells into endoderm-lineage cells and uses thereof.

Viral, nonviral and nonintegrating viral methods for generating induced pluripotent stem cells (iPSCs) using adenovirus, plasmids or excision of reprogramming factors using Cre-loxP3, or piggyBAC transposition have been described. See Stadtfeld, M., et al., *Science* 322, 945-949 (2008); Okita, K. et al., *Science* 322, 949-953 (2008); Kaji, K. et al. *Nature* 458, 771-775 (2009); Soldner, F. et al. *Cell* 136, 964-977 (2009); and Woltjen, K. et al. *Nature* 458, 766-770 (2009), which are herein incorporated in their entireties by reference. Also, see U.S. Patent Application number 20100003757 to Mack, A. et al. (published Jan. 7, 2010) and No.: PCT/US2009/037429 to Shi et al, which are herein also incorporated by reference in its entireties. These methods, however, have low reprogramming efficiencies (<0.003%), and may leave residual vector sequences despite excision, which limits their therapeutic applications. For example, viral integration in the host genome and over expression of the above transcription factors has been associated with tumorigenesis; and a residual transgene expression is potentially the feature which distinguishes ES cells and iPS cells. See Solder, F. et al., *Cell* 136:964-977 (2009); Foster et al., Oncogene 24:1491-1500 (2005); and Hochedlinger, K. et al., *Cell* 121: 465-477 (2005), which are herein incorporated by reference in their entireties.

In other embodiments of the invention, methods for generating iPSCs include episomal vectors derived from the Epstein-Barr virus. See Yu, J. et al. *Science* 324, 797-801 (2009) and U.S. Patent Application Publication No. 2010/0003757 to Mack, A. et al. published on Jan. 7, 2010, which references are herein incorporated in their entireties. These methods require three separate plasmids carrying a combination of seven factors, including the oncogene SV40.

In another embodiment of the invention, methods for generating iPSCs include protein-based iPSCs from mouse and human fetal and neonatal cells. See Zhou, H. et al. *Cell Stem Cell* 4, 381-384 (2009); and Kim, D. et al. *Cell Stem Cell* 4, 472-476 (2009), which are herein incorporated by reference in their entireties. These methodologies are accomplished using a chemical treatment (e.g. valproic acid in the case of Zhou et al. 2009 supra) or many rounds of treatment (Kim et al. 2009, supra).

In another embodiment of the invention, minicircle vectors or plasmids, which are supercoiled DNA molecules that lack a bacterial origin of replication and antibiotic resistance genes, can be used. See Chen, Z.-Y. et al., *Mol. Ther.* 8, 495-500 (2003); Chen, Z.-Y. et al., *Hum. Gene Ther.* 16, 126-131 (2005); and Jia, F. et al., *Nature Methods* Advance Publication Online 7 Feb. 2010, which are herein incorporated by reference in their entireties. These methodologies generate iPSCs with higher transfection efficiencies and longer ectopic expression because they have lower activation of exogenous silencing mechanisms.

Still in another embodiment of the invention, iPS cells can be generated from human patients with various diseases including, diabetic patients, ALS, spinal muscular dystrophy and Parkinson patients. See Maehr et al. PNAS USA 106(37): 15768-73 (2009); Dimos et al., Science, 321:1218-21 (2008); Ebert et al. Nature 457:277-80 (2009); Park et al. Cell 134: 877-886 (2008); and Soldner et al., Cell 136:964-977, which are herein incorporated by reference in their entireties. At least one advantage of producing hIPS cells from patients with specific diseases is that the cell derived would contain the genotype and cellular responses of the human disease. Also, see Table 3 listing at least some existing human iPS cell lines. This information was derived from the literature and publicly available databases including for example the National Institutes of Health (NIH) Stem Cell Registry, the Human Embryonic Stem Cell Registry and the International Stem Cell Registry located at the University of Massachusetts Medical School, Worcester, Mass., USA. These databases are periodically updated as cell lines become available and registration obtained.

Embodiments of the compositions and methods described herein contemplate the use of various differentiable primate pluripotent stem cells including human pluripotent stem cells such as hESC, including but not limited to, CyT49, CyT212, CyT203, CyT25, (commercially available at least at the time of filing of this instant application from ViaCyte Inc. located at 3550 General Atpmics Court, San Deigo Calif. 92121) BGO1, BG02 and MEL1, and induced pluripotent stem (iPS) cells such as iPSC-482c7 and iPSC-603 (Cellular Dynamics International, Inc., Madison, Wis.) and iPSC-G4 (hereinafter "G4") and iPSC-B7 (hereinafter, "B7") (Shinya Yamanaka, Center for iPS Cell Research, Kyoto University); studies using G4 and B7 are described in detail herein. Certain of these human pluripotent stem cells are registered with national registries such as the National Institutes of Health (NIH) and listed in the NIH Human Stem Cell Registry (e.g., CyT49 Registration No. #0041). Information on CyT49, other available cell lines can also be found on the worldwide web at stemcells.nih.gov/research/registry. Still other cell lines, e.g., BG01 and BG01v, are sold and distributed to third parties by WiCell®, an affiliate of the Wisconsin International Stem Cell (WISC) Bank (Catalog name, BG01) and ATCC (Catalog No. SCRC-2002), respectively. While other cell lines described herein may not be registered or distributed by a biological repository, such as WiCell® or ATCC, such cell lines are available to the public directly or indirectly from the principle investigators, laboratories and/or institutions. Public requests for cell lines and reagents, for example, are customary for those skilled in the art in the life sciences. Typically, transfer of these cells or materials is by way of a standard material transfer agreement between the proprietor of the cell line or material and the recipient. These types of material transfers occur frequently in a research environment, particularly in the life sciences. In fact, Applicant has routinely transferred cells since the time they were derived and characterized, including CyT49 (2006), CyT203 (2005), Cyt212 (2009), CyT25 (2002), BG01 (2001), BG02 (2001), BG03 (2001) and BG01v (2004), through such agreements with commercial and non-profit industry partners and collaborators. The year in parenthesis next to each cell line in the previous list indicates the year when the cell lines or materials became publicly available and immortal (e.g. cell banks were made) and thus destruction of another embryo has not been performed or required since the establishment of these cell lines in order to make the compositions and practice the methods described herein.

In August 2006, Klimanskaya et al. demonstrated that hESC can be derived from single blastomeres, hence keeping the embryo intact and not causing their destruction. Biopsies were performed from each embryo using micromanipulation techniques and nineteen (19) ES-cell-like outgrowths and two (2) stable hESC lines were obtained. These hESC lines were able to be maintained in an undifferentiated state for over six (6) months, and showed normal karyotype and expression of markers of pluripotency, including Oct-4, SSEA-3, SSEA-4, TRA-1-60, TRA-1-81, Nanog and Alkaline Phosphatase. These hESC can differentiate and form derivatives of all three (3) embryonic germ layers both in vitro and form in teratomas in vivo. These methods to create new stem cell lines without destruction of embryos addresses the ethical concerns of using human embryos. See Klimanskaya et al. (2006) *Nature* 444:481-5, Epub 2006 August 23, the disclosure of which is incorporated herein by reference in its entirety. However, Klimanskaya et al. co-cultured the derived hESC line with other hESC. Later, in 2008, Chung Y. et al., were able to obtain hES cell lines again from a single blastomere but without co-culture with hESC. See Chung Y. et al., *Cell Stem Cell* 2008, 2(2), 113-117, which is incorporated herein by reference in its entirety. Thus the compositions and methods described herein, and in particular, the such compositions and methods as related to induced pluripotent stem cells or genetically dedifferentiated pluripotent stem cells, do not require the destruction of a human embryo.

Tables 3 and 4 are non-exhaustive lists of certain iPSC and hESCs, respectively, which are available worldwide for research and/or commercial purposes, and are suitable for use in the methods and compositions of the present invention. The information in Tables 3 and 4 were derived from the literature and publicly available databases including, for example, the National Institutes of Health (NIH) Human Stem Cell Registry, the Human Embryonic Stem Cell Registry and the International Stem Cell Registry located at the University of Massachusetts Medical School, Worcester, Mass., USA. These databases are periodically updated as cell lines become available and registration obtained.

Human iPSC described herein (at least iPSC-603 and iPSC-482-c7) were provided by Cellular Dynamics International, Inc. (Madison, Wis., USA).

TABLE 3

| Listing of human induced pluripotent stem (hIPS) cell lines | |
|---|---|
| University of Wisconsin - Madison (USA) | 1. IPS(FORESKIN)-1 (Normal; 46XY; Yu, J., et al. [Thomson] Science. 2007 Induced pluripotent stem cell lines derived from human somatic cells 318(5858): 1917-20.)<br>2. IPS(FORESKIN)-2 (Normal; 46XY; Yu, J., et al. [Thomson] Science. 2007 Induced pluripotent stem cell lines derived from human somatic cells 318(5858): 1917-20.)<br>3. IPS(FORESKIN)-3 (Normal; 46XY; Yu, J., et al. [Thomson] Science. 2007 Induced pluripotent stem cell lines derived from human somatic cells 318(5858): 1917-20.)<br>4. IPS(FORESKIN)-4 (Normal; 46XY; Yu, J., et al. [Thomson] Science. 2007 Induced pluripotent stem cell lines derived from human somatic cells 318(5858): 1917-20.)<br>5. IPS(IMR90)-1 (Normal; 46XX; Yu, J., et al. [Thomson] Science. 2007 Induced pluripotent stem cell lines derived from human somatic cells 318(5858): 1917-20.)<br>6. IPS(IMR90)-2 (Normal; 46XX; Yu, J., et al. [Thomson] Science. 2007 Induced pluripotent stem cell lines derived from human somatic cells 318(5858): 1917-20.)<br>7. IPS(IMR90)-3 (Normal; 46XX; Yu, J., et al. [Thomson] Science. 2007 Induced pluripotent stem cell lines derived from human somatic cells 318(5858): 1917-20.)<br>8. IPS(IMR90)-4 (Normal; 46XX; Yu, J., et al. [Thomson] Science. 2007 Induced pluripotent stem cell lines derived from human somatic cells 318(5858): 1917-20.)<br>9. IPS-SMA-3.5 (Normal; 46XY; Type 1 Spinal Muscular Atrophy; Ebert, A. D., et al. 2009. Induced pluripotent stem cells from a spinal muscular atrophy patient Nature. 457: 277-80)<br>10. IPS-SMA-3.6 (Normal; 46XY; Type 1 Spinal Muscular Atrophy; Ebert, A. D., et al. 2009. Induced pluripotent stem cells from a spinal muscular atrophy patient Nature. 457: 277-80)<br>11. IPS-WT (Normal; 46XX; Type 1 Spinal Muscular Atrophy; Ebert, A. D., et al. 2009. Induced pluripotent stem cells from a spinal muscular atrophy patient Nature. 457: 277-80) |
| University of California, Los Angeles (USA) | 1. IPS-1 (Karumbayaram, S. et al. 2009. Directed Differentiation of Human-Induced Pluripotent Stem Cells Generates Active Motor NeuronsStem Cells. 27: 806-811; Lowry, W. E., et al. 2008. Generation of human induced pluripotent stem cells from dermal fibroblasts Proc Natl Acad Sci USA. 105: 2883-8)<br>2. IPS-2 (Karumbayaram, S. et al. 2009. Directed Differentiation of Human-Induced Pluripotent Stem Cells Generates Active Motor NeuronsStem Cells. 27: 806-811; Lowry, W. E., et al. 2008. Generation of human induced pluripotent stem cells from dermal fibroblastsProc Natl Acad Sci USA. 105: 2883-8)<br>3. IPS-5 (Lowry, W. E., et al. 2008. Generation of human induced pluripotent stem cells from dermal fibroblasts Proc Natl Acad Sci USA. 105: 2883-8)<br>4. IPS-7 (Lowry, W. E., et al. 2008. Generation of human induced pluripotent stem cells from dermal fibroblasts Proc Natl Acad Sci USA. 105: 2883-8)<br>5. IPS-18 (Karumbayaram, S. et al. 2009. Directed Differentiation of Human-Induced Pluripotent Stem Cells Generates Active Motor NeuronsStem Cells. 27: 806-811; Lowry, W. E., et al. 2008. Generation of human induced pluripotent stem cells from dermal fibroblastsProc Natl Acad Sci USA. 105: 2883-8)<br>6. IPS-24 (Lowry, W. E., et al. 2008. Generation of human induced pluripotent stem cells from dermal fibroblasts Proc Natl Acad Sci USA. 105: 2883-8)<br>7. IPS-29 (Lowry, W. E., et al. 2008. Generation of human induced pluripotent stem cells from dermal fibroblasts Proc Natl Acad Sci USA. 105: 2883-8) |
| Mt. Sinai Hospital (Samuel Lunenfeld Research Institute; USA) | 1. 60 (Woltjen, K. et al. 2009. PiggyBac transposition reprograms fibroblasts to induced pluripotent stem cells Nature. 458(7239): 766-70)<br>2. 61 (Woltjen, K. et al. 2009. PiggyBac transposition reprograms fibroblasts to induced pluripotent stem cells Nature. 458(7239): 766-70)<br>3. 66 (Woltjen, K. et al. 2009. PiggyBac transposition reprograms fibroblasts to induced pluripotent stem cells Nature 458(7239): 766-70)<br>4. 67 (Woltjen, K. et al. 2009. PiggyBac transposition reprograms fibroblasts to induced pluripotent stem cells Nature 458(7239): 766-70)<br>5. HIPSC117 (Kaji K, et al. 2009 Virus-free induction of pluripotency and subsequent excision of reprogramming factors Nature 458(7239): 771-5) |

TABLE 3-continued

Listing of human induced pluripotent stem (hIPS) cell lines

|  |  |
|---|---|
|  | 6. HIPSC121 (Kaji K, et al. 2009 Virus-free induction of pluripotency and subsequent excision of reprogramming factors Nature 458(7239): 771-5) |
|  | 7. HIPSC122 (Kaji K, et al. 2009 Virus-free induction of pluripotency and subsequent excision of reprogramming factors Nature 458(7239): 771-5) |
| Children's Hospital - Boston (USA) | 1. 551-IPS8 (Park IH, et al. 2008. Reprogramming of human somatic cells to pluripotency with defined factors Nature 451: 141-6). |
|  | 2. ADA-IPS2 ((ADA-SCID) Adenosine Deaminase Deficiency-related Severe Combined Immunodeficiency (GGG > AGG, exon 7, ADA gene); Park, I. H. et al. 2008. Disease-Specific Induced Pluripotent Stem Cells Cell 134(5): 877-86) |
|  | 3. ADA-IPS3 ((ADA-SCID) Adenosine Deaminase Deficiency-related Severe Combined Immunodeficiency (GGG > AGG, exon 7, ADA gene); Park, I. H. et al. 2008. Disease-Specific Induced Pluripotent Stem Cells Cel l134(5): 877-86) |
|  | 4. BJ1-IPS1 (Park, I. H. et al. 2008. Disease-Specific Induced Pluripotent Stem Cells Cell 134(5): 877-86) |
|  | 5. BMD-IPS1 (Male; (BMD) Becker Muscular Dystrophy (Unidentified mutation in dystrophin); Park, I. H. et al. 2008. Disease-Specific Induced Pluripotent Stem Cells Cell 134(5): 877-86) |
|  | 6. BMD-IPS4 (Normal; 46XY; (BMD) Becker Muscular Dystrophy (Unidentified mutation in dystrophin); Park, I. H. et al. 2008. Disease-Specific Induced Pluripotent Stem Cells Cell 134(5): 877-86) |
|  | 7. DH1CF16-IPS1 (Normal; 46XY; Park, I. H. et al. 2008. Disease-Specific Induced Pluripotent Stem Cells Cell 134(5): 877-86) |
|  | 8. DH1CF32-IPS2 (Male; Park, I. H. et al. 2008. Disease-Specific Induced Pluripotent Stem Cells Cell 134(5): 877-86) |
|  | 9. DH1F-IPS3-3(Normal; 46XY; Park, I. H. et al. 2008. Disease-Specific Induced Pluripotent Stem Cells Cell 134(5): 877-86) |
|  | 10. DMD-IPS1 ((Normal; 46XY; DMD) Duchenne Muscular Dystrophy (Deletion of exon 45-52, dystrophin gene; Park, I. H. et al. 2008. Disease-Specific Induced Pluripotent Stem Cells Cell 134(5): 877-86) |
|  | 11. DMD-IPS2 (Male; (DMD) Duchenne Muscular Dystrophy (Deletion of exon 45-52, dystrophin gene; Park, I. H. et al. 2008. Disease-Specific Induced Pluripotent Stem Cells Cell 134(5): 877-86) |
|  | 12. DS1-IPS4 (Male; Down syndrome (Trisomy 21); Park, I. H. et al. 2008. Disease-Specific Induced Pluripotent Stem Cells Cell 134(5): 877-86) |
|  | 13. DS2-IPS1 (Male; Down syndrome (Trisomy 21); Park, I. H. et al. 2008. Disease-Specific Induced Pluripotent Stem Cells Cell 134(5): 877-86) |
|  | 14. DS2-IPS10 (Male; Down syndrome (Trisomy 21); Park, I. H. et al. 2008. Disease-Specific Induced Pluripotent Stem Cells Cell 134(5): 877-86) |
|  | 15. GD- IPS1(Male; (GD) Gaucher Disease type III (AAC > AGC, exon 9, G-insertion, nucleotide 84 of cDNA, GBA gene; Park, I. H. et al. 2008. Disease-Specific Induced Pluripotent Stem Cells Cell 134(5): 877-86) |
|  | 16. GD-IPS3 (Male; (GD) Gaucher Disease type III (AAC > AGC, exon 9, G-insertion, nucleotide 84 of cDNA, GBA gene; Park, I. H. et al. 2008. Disease-Specific Induced Pluripotent Stem Cells Cell 134(5): 877-86) |
|  | 17. HFIB2-IPS2 (Park, I. H., et al. 2008. Generation of human-induced pluripotent stem cells Nat Protoc. 3: 1180-6; Park, I. H. et al. 2008. Reprogramming of human somatic cells to pluripotency with defined factors Nature 451: 141-6) |
|  | 18. HFIB2-IPS4 (Park, I. H., et al. 2008. Generation of human-induced pluripotent stem cells Nat Protoc. 3: 1180-6; Park, I. H. et al. 2008. Reprogramming of human somatic cells to pluripotency with defined factors Nature 451: 141-6) |
|  | 19. HFIB2-IPS5 (Park, I. H., et al. 2008. Generation of human-induced pluripotent stem cells Nat Protoc. 3: 1180-6; Park, I. H. et al. 2008. Reprogramming of human somatic cells to pluripotency with defined factors Nature 451: 141-6) |
|  | 20. JDM-IPS1 (Normal, 46XX; Juvenile diabetes mellitus (multifactorial); Park, I. H. et al. 2008. Disease-Specific Induced Pluripotent Stem Cells Cell 134(5): 877-86) |
|  | 21. JDM-IPS1 (Normal, 46XX; Juvenile diabetes mellitus (multifactorial); Park, I. H. et al. 2008. Disease-Specific Induced Pluripotent Stem Cells Cell 134(5): 877-86) |
|  | 22. JDM-IPS2 (Female; Juvenile diabetes mellitus (multifactorial); Park, I. H. et al. 2008. Disease-Specific Induced Pluripotent Stem Cells Cell 134(5): 877-86) |
|  | 23. JDM-IPS3 (Female; Juvenile diabetes mellitus (multifactorial); Park, I. H. et al. 2008. Disease-Specific Induced Pluripotent Stem Cells Cell 134(5): 877-86) |
|  | 24. LNSC-IPS2 (Female; Lesch-Nyhan syndrome (carrier, heterozygosity of HPRT1; Park, I. H. et al. 2008. Disease-Specific Induced Pluripotent Stem Cells Cell 134(5): 877-86) |
|  | 25. MRC5-IPS7 (Male; Park, I. H. et al. 2008. Disease-Specific Induced Pluripotent Stem Cells Cell134(5): 877-86) |

TABLE 3-continued

Listing of human induced pluripotent stem (hIPS) cell lines

| | |
|---|---|
| | 26. MRC5-IPS12 (Normal; 46XY; Park, I. H. et al. 2008. Disease-Specific Induced Pluripotent Stem Cells Cell 134(5): 877-86) |
| | 27. MRC5-IPS1 (Male; Park, I. H. et al. 2008. Disease-Specific Induced Pluripotent Stem Cells Cell 134(5): 877-86) |
| | 28. PD-IPS1 (Male; Parkinson disease (multifactorial); Park, I. H. et al. 2008. Disease-Specific Induced Pluripotent Stem Cells Cell 134(5): 877-86) |
| | 29. SBDS-IPS1 (Male; Swachman-Bodian-Diamond syndrome (IV2 + 2T > C and IV3 − 1G > A, SBDS gene; Park, I. H. et al. 2008. Disease-Specific Induced Pluripotent Stem Cells Cell 134(5): 877-86) |
| | 30. SBDS-IPS2 |
| | 31. SBDS-IPS3 (Normal; 46XY; Swachman-Bodian-Diamond syndrome (IV2 + 2T > C and IV3 − 1G > A, SBDS gene; Park, I. H. et al. 2008. Disease-Specific Induced Pluripotent Stem Cells Cell 134(5): 877-86) |
| Harvard University (USA) | 1. A29a (46XX; (ALS) Amyotrophic Lateral Sclerosis (L144F [Leu144 > Phe] dominant allele of the superoxide dismutase (SOD1) gene; Caucasian; Dimos, J. T., et al. 2008. Induced pluripotent stem cells generated from patients with ALS can be differentiated into motor neurons Science. 321: 1218-21) |
| | 2. A29b (46XX; (ALS) Amyotrophic Lateral Sclerosis (L144F [Leu144 > Phe] dominant allele of the superoxide dismutase (SOD1) gene; Caucasian; Dimos, J. T., et al. 2008. Induced pluripotent stem cells generated from patients with ALS can be differentiated into motor neurons Science. 321: 1218-21) |
| | 3. A29c (46XX; (ALS) Amyotrophic Lateral Sclerosis (L144F [Leu144 > Phe] dominant allele of the superoxide dismutase (SOD1) gene; Caucasian; Dimos, J. T., et al. 2008. Induced pluripotent stem cells generated from patients with ALS can be differentiated into motor neurons Science 321: 1218-21) |
| Salk Institute (USA) | 1. HAIR-IPS1 (Aasen, T., et al [Belmonte, J. C.] 2008. Efficient and rapid generation of induced pluripotent stem cells from human keratinocytes Nat Biotechnol 26: 1276-84) |
| | 2. HAIR-IPS2 (Aasen, T., et al [Belmonte, J. C.] 2008. Efficient and rapid generation of induced pluripotent stem cells from human keratinocytes Nat Biotechnol 26: 1276-84) |
| Royan Institute (Iran) | 1. R.1.H.iPSC.1(OCT4, Sox2, KLF4, c-Myc; Human fibroblasts) |
| | 2. BOM.1.H.iPSC.1 (OCT4, Sox2, KLF4, c-Myc; Human fibroblasts) |
| | 3. FHC.1.H.iPSC.3 (OCT4, Sox2, KLF4, c-Myc; Human fibroblasts) |
| | 4. GSD.1.H.iPSC.7 (OCT4, Sox2, KLF4, c-Myc; Human fibroblasts) |
| | 5. TYR.1.H.iPSC.1 (OCT4, Sox2, KLF4, c-Myc; Human fibroblasts) |
| | 6. HER.1.H.iPSC.1 (OCT4, Sox2, KLF4, c-Myc; Human fibroblasts) |
| | 7. R.1.H.iPSC.4 (OCT4, Sox2, KLF4, c-Myc; Human fibroblasts) |
| | 8. R.1.H.iPSC.9 (OCT4, Sox2, KLF4, c-Myc; Human fibroblasts) |
| | 9. RP2.H.iPSC.3 (OCT4, Sox2, KLF4, c-Myc; iPS cells) |
| | 10. LCA.1.H.iPSC.1 (OCT4, Sox2, KLF4, c-Myc; iPS cells) |
| | 11. USH.1.H.iPSC.6 (OCT4, Sox2, KLF4, c-Myc; Human fibroblasts) |
| | 12. RP.1.H.iPSC.2 (OCT4, Sox2, KLF4, c-Myc; Human fibroblasts) |
| | 13. ARMD.1.H.iPSC.2 (OCT4, Sox2, KLF4, c-Myc; Human fibroblasts) |
| | 14. LHON.1.H.iPSC.5 (OCT4, Sox2, KLF4, c-Myc; iPS cells) |
| | 15. CNS.1.H.iPSC.10 (OCT4, Sox2, KLF4, c-Myc; iPS cells) |
| | 16. CNS.2.H.iPSC.7 (OCT4, Sox2, KLF4, c-Myc; iPS cells) |
| Centre of Regenerative Medicine in Barcelona (Spain) | 1. KiPS4F-1 (OCT4, Sox2, KLF4, c-Myc; human foreskin keratinocytes; 46XY) |
| | 2. KiPS3F-7 (OCT4, Sox2, KLF4); human foreskin keratinocytes) |
| | 3. KiPS4F-8 (OCT4, Sox2, KLF4, c-Myc human foreskin keratinocytes; 46XY) |
| | 4. cFA404-KiPS4F-1 (OCT4, Sox2, KLF4, c-Myc; Epidermal keratinocytes; 46XY) |
| | 5. cFA404-KiPS4F-3 (OCT4, Sox2, KLF4, c-Myc; Epidermal keratinocytes; 46XY) |
| Université Paris-Sud 11 (France) | 1. PB03 (Oct4, Sox2, Lin28, Nanog; Primary Amniocytes; 46XX; Lentivirus) |
| | 2. PB04 (Oct4, Sox2, Lin28, Nanog; Primary Amniocytes; B-Thalassemia affected; 46XY; Lentivirus) |
| | 3. PB05-1 (Oct4, Sox2, Lin28, Nanog; Primary Amniocytes; B-Thalassemia affected; 46XY; Lentivirus) |
| | 4. PB05 (Oct4, Sox2, Lin28, Nanog; Primary Amniocytes; B-Thalassemia affected; 46XY; Lentivirus) |
| | 5. PB06 (Oct4, Sox2, Lin28, Nanog; Primary Amniocytes; Down Syndrome; 47XY, +21; Lentivirus) |
| | 6. PB06-1 (Oct4, Sox2, Lin28, Nanog; Primary Amniocytes; Down Syndrome; 47XY, +21; Lentivirus) |
| | 7. PB07 (OCT4, Sox2, KLF4, c-Myc; Primary Amniocytes; 46XY; Retrotivirus) |
| | 8. PB08 (OCT4, Sox2, KLF4, c-Myc; Primary Amniocytes; 46XY; Retrotivirus) |
| | 9. PB09 (Oct4, Sox2, Lin28, Nanog; Primary Amniocytes; 46XY; Lentivirus) |
| | 10. PB10 (Oct4, Sox2; Primary Amniocytes46XY, Lentivirus) |

TABLE 3-continued

Listing of human induced pluripotent stem (hIPS) cell lines

| | |
|---|---|
| Kyoto University (Japan) | 1. 201B1 (human fibroblast; 46XX)<br>2. 201B2 (human fibroblast; 46XX)<br>3. 201B3 (human fibroblast; 46XX)<br>4. 201B6 (human fibroblast; 46XX)<br>5. 201B7 (human fibroblast; 46XX)<br>6. 243H1 (human fibroblast)<br>7. 243H7 (human fibroblast)<br>8. 246B1 (Normal, 46XX)<br>9. 246B2 (Normal, 46XX)<br>10. 246B3 (Normal, 46XX)<br>11. 246B4 (Normal, 46XX)<br>12. 246B5 (Normal, 46XX)<br>13. 246B6 (Normal, 46XX)<br>14. 246G1 (human fibroblast; Takahashi, K., et al. 2007. Induction of pluripotent stem cells from adult human fibroblasts by defined factors Cell. 131: 861-72)<br>15. 246G3 (human fibroblast; Takahashi, K., et al. 2007. Induction of pluripotent stem cells from adult human fibroblasts by defined factors Cell. 131: 861-72)<br>16. 246G4 (human fibroblast; Takahashi, K., et al. 2007. Induction of pluripotent stem cells from adult human fibroblasts by defined factors Cell. 131: 861-72)<br>17. 246G5 (human fibroblast; Takahashi, K., et al. 2007. Induction of pluripotent stem cells from adult human fibroblasts by defined factors Cell. 131: 861-72)<br>18. 246G6 (human fibroblast; Takahashi, K., et al. 2007. Induction of pluripotent stem cells from adult human fibroblasts by defined factors Cell. 131: 861-72)<br>19. 253F1 (Normal, 46XX; Takahashi, K., et al. 2007. Induction of pluripotent stem cells from adult human fibroblasts by defined factors Cell. 131: 861-72)<br>20. 253F2 (Normal, 46XX; Takahashi, K., et al. 2007. Induction of pluripotent stem cells from adult human fibroblasts by defined factors Cell. 131: 861-72)<br>21. 253F3 (Normal, 46XX; Takahashi, K., et al. 2007. Induction of pluripotent stem cells from adult human fibroblasts by defined factors Cell. 131: 861-72)<br>22. 253F4 (Normal, 46XX; Takahashi, K., et al. 2007. Induction of pluripotent stem cells from adult human fibroblasts by defined factors Cell. 131: 861-72)<br>23. 253F5 (Normal, 46XX; Takahashi, K., et al. 2007. Induction of plunpotent stem cells from adult human fibroblasts by defined factors Cell. 131: 861-72) |
| Shanghai Institutes for Biological Sciences (China) | 24. HAFDC-IPS-6 (Li C., et al. 2009 Pluripotency can be rapidly and efficiently induced in human amniotic fluid-derived cells Hum Mol Genet. 2009 Nov. 15; 18(22): 4340-9)<br>25. IPS-S (Liao, J., et al. 2008. Enhanced efficiency of generating induced pluripotent stem (iPS) cells from human somatic cells by a combination of six transcription factors Cell Res. 18: 600-3) |

Another advantage is that such hIPS cells would be an immunologically matched autologous cell population; and patient-specific cells would allow for studying origin and progression of the disease. Thus, it is possible to understand the root causes of a disease, which can provide insights leading to development of prophylactic and therapeutic treatments for the disease.

Pluripotent Human Embryonic Stem (hES) Cells

Some embodiments are directed to methods for deriving definitive endoderm cells and ultimately any endoderm-lineage derived cell type, including but not limited to, foregut endoderm, pancreatic endoderm, endocrine precursor cells and/or pancreatic islet hormone-expressing cells using human embryonic stem (hES) cells as the starting material. These hES cells can be cells that originate from the morula, embryonic inner cell mass or those obtained from embryonic gonadal ridges. Human embryonic stem cells can be maintained in culture in a pluripotent state without substantial differentiation using methods that are known in the art. Such methods are described, for example, in U.S. Pat. Nos. 5,453, 357, 5,670,372, 5,690,926 5,843,780, 6,200,806 and 6,251, 671 the disclosures of which are incorporated herein by reference in their entireties.

In some processes, pluripotent stem cells, e.g. hES cells, are maintained on a feeder layer. In such processes, any feeder layer which allows pluripotent cell to be maintained in a pluripotent state can be used. One commonly used feeder layer for the cultivation of human embryonic stem cells is a layer of mouse fibroblasts. More recently, human fibroblast feeder layers have been developed for use in the cultivation of pluripotent cell (see US Patent Application Publication No. 2002/0072117, the disclosure of which is incorporated herein by reference in its entirety). Alternative processes permit the maintenance of pluripotent cells without the use of a feeder layer. Methods of maintaining pluripotent cells under feeder-free conditions have been described in US Patent Application Publication No. 2003/0175956, the disclosure of which is incorporated herein by reference in its entirety.

The pluripotent cells described herein can be maintained in culture either with or without serum, with or without extracellular matrix, with or without FGF. In some pluripotent cell maintenance procedures, serum replacement is used. These and other methods for culturing and differentiation pluripotent or multipotent cells, respectively, are described in PCT/US2007/062755, filed Feb. 23, 2007, and titled COMPOSI- TIONS AND METHODS FOR CULTURING DIFFERENTIAL CELLS and PCT/US2008/080516, filed Oct. 20, 2008, and titled METHODS AND COMPOSITIONS FOR FEEDER-FREE PLURIPOTENT STEM CELL MEDIA CONTAINING HUMAN SERUM, which are herein incorporated in their entireties.

The invention described herein is useful with all hES cell lines, and at least those listed in Table 4. This information was derived from the literature and publicly available databases including for example the National Institutes of Health (NIH) Stem Cell Registry, the Human Embryonic Stem Cell Registry and the International Stem Cell Registry located at the University of Massachusetts Medical School, Worcester, Mass., USA. These databases are periodically updated as cell lines become available and registration obtained. As of the filing date of this application there were 254 iPSC lines listed with the Internation Stem Cell Registry and 1211 hESC lines. Table 4 below is not inclusive of all hESC and iPSC that are listed, but rather, are examples of the pluripotent stem cells potentially available.

TABLE 4

Listing of human embryonic stem (hES) cell lines

| Institution (Country) | Name |
|---|---|
| U.S.A. | |
| BresaGen, Inc., Athens, Georgia (USA) | BG01, BG02, BG03; BG04; BG01v |
| Invitrogen (USA) | BG01v/hOG |
| CyThera, Inc., San Diego, California (USA) | CyT49, CyT203, CyT25 |
| Geron Corporation, Menlo Park, California (USA) | GE01, GE07, GE09, GE13, GE14, GE91, GE92 (H1, H7, H9, H13, H14, H9.1, H9.2) |
| University of California, San Francisco, California (USA) | UC01, UC06 (HSF-1, HSF-6); UCSFB1, UCSFB2, UCSFB3, UCSFB4, UCSFB5, UCSFB6, UCSFB7, UCSFB8, UCSFB9 & UCSFB10 |
| Wisconsin Alumni Research Foundation, Madison, Wisconsin (USA) | WA01, WA07, WA09, WA13, WA14 (H1, H7, H9, H13, H14) |
| Children's Hospital Corporation (USA) | CHB-1, CHB-2 CHB-3 CHB-4, CHB-5, CHB-6, CHB-8, CHB-9, CHB-10, CHB-11 & CHB-12 |
| The Rockefeller University (USA) | RUES1, RUES2 & RUES3 |
| Harvard University (USA) | HUES1, HUES2, HUES3, HUES4, HUES5, HUES6, HUES7, HUES8, HUES9, HUES10, HUES11, HUES12, HUES13, HUES14, HUES15, HUES16, HUES17, HUES18, HUES19, HUES20, HUES21, HUES22, HUES23, HUES24, HUES25, HUES26, HUES27; HUES28; HUES48; HUES49; HUES53; HUES55 & HUES 56 |
| Mt Sinai Hospital-Samuel Lunenfeld Research Institute (USA) | CA1 & CA2 |
| Children's Memorial Hospital (USA) | CM-1, CM-2, CM-5, CM-6, CM-7, CM-8, CM-11, CM-12, CM-13, CM-14, CM-16 |
| The University of Texas Health Science Center at Houston (USA) | CR1 & CR2 |
| California Stem Cell, Inc. (USA) | CSC14 |
| University of Connecticut School of Medicine/Dentistry (USA) | CSC14, CT1, CT2, CT3, & CT4 |
| The Third Affiliated Hospital of Guangzhou Medical College (USA) | FY-3PN; FY-hES-1; FY-hES-3; FY-hES-5; FY-hES-7 & FY-hES-8 |
| Advanced Cell Technology, Inc. (USA) | MA 01; MA 09; MA 42; MA 50; MA135; NED 1; NED 2; NED 3 & NED 4 |
| Stanford University (USA) | MFS5 |
| New York University School of Medicine (USA) | NYUES1; NYUES2; NYUES3; NYUES4; NYUES5; NYUES6 & NYUES7 |
| Reprogenetics, LLC (USA) | RNJ7 |
| University of California, Los Angeles (USA) | UCLA1; UCLA2 & UCLA3 |
| Eastern Virginia Medical School (USA) | ES-76; ES-78-1; ES-78-2 |
| Reproductive Genetics Institute (USA) | RG-222; RG-230; RG-249; RG-308; RG-313; RG-148; DYSTROPHIA MYOTONICA 1 (DM1), affected, 46, XY; RG-153; DYSTROPHIA MYOTONICA 1 (DM1), affected, 46, XX; RG-170; MUSCULAR DYSTROPHY, BECKER TYPE (BMD), affected, 46, XY; RG-186; HUNTINGTON DISEASE (HD), affected, 46, XX; RG-194; HUNTINGTON DISEASE (HD), affected, 46, XY; RG-233; HEMOGLOBIN B LOCUS (HBB), affected (HbS/HbS - sickle cell anemia), 46, XX; RG-245; EMERY-DREIFUSS MUSCULAR DYSTROPHY, X-LINKED (EDMD), carrier, 47, XXY; RG-246; EMERY-DREIFUSS MUSCULAR DYSTROPHY, X-LINKED (EDMD), affected, 46, XY; RG-271; TORSION DYSTONIA 1 (DYT1), AUTOSOMAL DOMINANT, affected (N/GAG del), 46, XY; |

TABLE 4-continued

Listing of human embryonic stem (hES) cell lines

| Institution (Country) | Name |
|---|---|
| | RG-283; MUSCULAR DYSTROPHY, DUCHENNE TYPE (DMD), affected, 46, XY; RG-288; CYSTIC FIBROSIS (CF), affected (deltaF508/deltaF508), 46, XY; RG-289; CYSTIC FIBROSIS (CF), affected (deltaF508/deltaF508), 46, XX; RG-301; MUSCULAR DYSTROPHY, DUCHENNE TYPE(DMD) affected, 46, XY; RG-302; MUSCULAR DYSTROPHY, DUCHENNE TYPE (DMD), carrier, 46, XX; RG-315; NEUROFIBROMATOSIS, TYPE I (NF1), affected (R19 47X/N), 46, XY; RG-316; TUBEROUS SCLEROSIS, TYPE 1(TSC1), affected (N/IVS7 + 1 G-A); RG-316; TUBEROUS SCLEROSIS, TYPE 1(TSC1), affected (N/IVS7 + 1 G-A); RG-320; TUBEROUS SCLEROSIS, TYPE 1(TSC1), affected (N/IVS7 + 1 G-A); RG-326; POPLITEAL PTERYGIUM SYNDROME (PPS), affected (R84H/N), 46, XY; RG-328; FACIOSCAPULOHUMERAL MUSCULAR DYSTROPHY 1A(FSHD), affected, 46, XY; RG-330; FACIOSCAPULOHUMERAL MUSCULAR DYSTROPHY 1A (FSHD), affected, 46, XY; RG-333; FACIOSCAPULOHUMERAL MUSCULAR DYSTROPHY 1A (FSHD), affected, 46, XX; RG-356; HEMOGLOBIN ALPHA LOCUS (HBA), affected (-alpha/--), 46, XX; RG-357; EMERY-DREIFUSS MUSCULAR DYSTROPHY, X-LINKED (EDMD), affected, 46, XY; RG-358; EMERY-DREIFUSS MUSCULAR DYSTROPHY, X-LINKED (EDMD), affected, 46, XY; RG-399; FACIOSCAPULOHUMERAL MUSCULAR DYSTROPHY 1A (FSHD), affected, 46, XX; RG-401; FACIOSCAPULOHUMERAL MUSCULAR DYSTROPHY 1A (FSHD), affected, 46, XX; RG-402; FACIOSCAPULOHUMERAL MUSCULAR DYSTROPHY 1A (FSHD), affected, 46, XX; RG-403; FACIOSCAPULOHUMERAL MUSCULAR DYSTROPHY 1A (FSHD), affected; RG-404; SPINAL MUSCULAR ATROPHY, TYPE I (SMA1), affected, 46, XY; RG-406; TORSION DYSTONIA 1, AUTOSOMAL DOMINANT (DYT1), affected (N/GAG del); RG-413; BREAST CANCER, FAMILIAL (BRCA2), affected (N/IVS7 GT del) & MULTIPLE ENDOCRINE NEOPLASIA, TYPE I (MEN1), affected (N/3036 4bp del); RG-414; MULTIPLE ENDOCRINE NEOPLASIA, TYPE I (MEN1), affected (N/3036 4bp del); RG-415; HUNTINGTON DISEASE (HD), affected; RG-416; CYSTIC FIBROSIS (CF), affected (deltaF508/1717-1 G-A); RG-417; CYSTIC FIBROSIS (CF), affected (deltaF508/1717-1 G-A); RG-418; HEMOGLOBIN B LOCUS (HBB), affected (cd8 + G/619del); RG-420; HEMOGLOBIN B LOCUS (HBB), affected (cd8 + G/619del); RG-422; CYSTIC FIBROSIS (CF), affected (N1303K/deltaF508); RG-423; CYSTIC FIBROSIS (CF), carrier (N/deltaF508); RG-424; MULTIPLE ENDOCRINE NEOPLASIA, TYPE 2 (MEN2B), affected (M918T/N); RG-426; PELIZAEUS-MERZBACHER DISEASE (PMLD), affected; |

TABLE 4-continued

Listing of human embryonic stem (hES) cell lines

| Institution (Country) | Name |
|---|---|
| | RG-428; TUBEROUS SCLEROSIS, TYPE 1 (TSC1), affected (N/IVS7 + 1 G-A); |

South American

| Institution (Country) | Name |
|---|---|
| Institute de Biociências, São Paulo (Brazil) | BR-1 |

Middle East

| Institution (Country) | Name |
|---|---|
| Technion-Israel Institute of Technology, Haifa (Israel) | TE03, TE04, TE06 (I 3, I 4, I 6) |
| Hadassah University Hospital (Israel) | HAD 1; HAD 2; HAD 3; HAD 4; HAD 5; HAD 6 |
| Hebrew University of Jerusalem | HEFX1 |
| Technion - Israel Institute of Technology | I3; I3.2; I3.3; 14; 16; 16.2; J3; J3.2 |
| Royan Institute (Iran) | ARMD.1.H.iPSC.2; BOM.1.H.iPSC.1; CNS.1.H.iPSC.10; CNS.2.H.iPSC.7; FHC.1.H.iPSC.3; GSD.1.H.iPSC.7; HER.1.H.iPSC.1; LCA.1.H.iPSC.1; LHON.1.H.iPSC.5; R.1.H.iPSC.1; R.1.H.iPSC.4; R.1.H.iPSC.9; Royan H1; Royan H10; Royan H2; Royan H3; Royan H4; Royan H5; Royan H6; Royan H7; Royan H8; Royan H9; RP.1.H.iPSC.2; RP2.H.iPSC.3; TYR.1.H.iPSC.1; USH.1.H.iPSC.6 |

Europe

| Institution (Country) | Name |
|---|---|
| Cellartis AB, Gotenberg (Sweden) | SA001, SA002 (Sahlgrenska 1, Sahlgrenska 2); SA002.2; SA003; AS034.1; AS034.1.1; AS034.2; AS038; AS046; FC018; ASo85; AS094; SA111; SA121; SA142; SA167; SA181; SA191; SA196; SA202; SA203; SA211; SA218; SA240; SA279; SA348; SA352; SA399; SA461; SA502; SA506; SA521; SA540; SA611 |
| Karolinska Institutet (Sweden) | HS181; HS207; HS235; HS237; HS293; HS306; HS346; HS351; HS356; HS360; HS361; HS362; HS363; HS364; HS366; HS368; HD380; HS382; HS400; HS401; HS402; HS415; HS420; HS422; HS426; HS429; HS429A; HS429B; HS429C; HS429D; HS475; HS480; HS481; HS539 |
| Göteborg University, Göteborg (Sweden) | SA04-SA19 (Sahlgrenska 4-Sahlgrenska 19) |
| Karolinska Institute, Stockholm (Sweden) | KA08, KA09, KA40, KA41, KA42, KA43 (hICM8, hICM9, hICM40, hICM41, hICM42, hICM43) |
| Geneva University (Switzerland) | CH-ES1 |
| University of Basel (Switzerland) | CH-ES3; CH-ES3; CH-ES5 |
| Roslin Cells Ltd (UK) | RC2; RC3; RC4; RC5 |
| University of Newcastle upon Tyne (UK) | NCL-1; NCL-2; NCL-3; NCL-4; NCL-5; NCL-6; NCL-7; NCL-8; NCL-9 |
| Roslin Institute (Edinburgh) & Geron Corporation (UK) | RH1; RH2; RH3; RH4; RH5; RH6; RH7; RH9; |
| University of Manchester (UK) | Man 2 |
| King's College London (UK) | KCL-001 (formerly WT3) |
| The University of Sheffield, Sheffield (UK) | SHEF-1; SHEF-2; SHEF-3; SHEF-4; SHEF-5; SHEF-6; SHEF-7; SHEF-8 |
| Universities of Edinburgh & Oxford; University of Cambridge (UK) | Edi-1; Edi-2; Edi-3; Edi-4 |
| Roslin Cells Ltd, Roslin Institute, Universities of Edinburgh & Manchester, Central Manchester & Manchester Children's University Hospitals NHS Trust (UK) | RCM-1; RC-1; RC-2; RC-3; RC-4; RC-5; RC-6; RC-7; RC-8; RC-9; RC-10 |
| King's College London & Guy's Hospital Trust/Charitable Foundation of Guy's & St Thomas (UK) | KCL-003-CF1 (formerly CF1); KCL-005-HD1; KCL008-HD-2; KCL009-trans-1; KCL-001 (WT-3); KCL-001 (WT-4) |
| Stem Cell Sciences Ltd, Australia (SCS) & Australian Stem Cell Centre (ASCC) | MEL-1; MEL-2; MEL-3; MEL-4 |
| University of Edinburgh (UK) | CB660 |
| Axordia Ltd. (UK) | Shef-1; Shef-2; Shef-3; Shef-4; Shef-5; Shef-6; Shef-7 |
| University of Nottingham (UK) | Nott-1; Nott-2 |
| Centre of Regenerative Medicine in Barcelona (Spain) | ES-2; ES-3; ES-4; ES-5; ES-6; ES-7; ES-8; ES-9; ES-10; ES-11EM; cFA404-KiPS4F-1; cFA404-KiPS4F-3; KiPS3F-7; KiPS4F-1; KiPS4F-8 |
| Principe Felipe Centre de Investigacion (Spain) | VAL-3; VAL-4; VAL-5; VAL-6M; VAL-7; VAL-8; VAL-9; VAL-10B |
| Université Libre de Bruxelles (Belgium) | ERA-1; ERA2; ERA-3; ERAMUC-1; ERAMUC-1 |

TABLE 4-continued

Listing of human embryonic stem (hES) cell lines

| Institution (Country) | Name |
|---|---|
| Vrije Universiteit Brussel (Belgium) | VUB01; VUB02; VUB06; VUB07; VUB03__DM1; VUB04__CF; VUB05__HD; VUB08__MFS; VUB09__FSHD; VUB10__SCA7; VUB11__FXS; VUB13__FXS; VUB14; VUB19__DM1; VUB20__CMT1A; VUB22__CF; VUB23__OI; VUB24__DM1; VUB26; VUB27; VUB28__HD__MFS |
| Central Manchester and Manchester Children's University Hospitals NHS (UK) | Man 1; Man 2 |
| Université Paris-Sud 11 (France) | CL01; CL02; CL03; PB04; PB05; PB05-1; PB06; PB06-1; PB07; PB08; PB09; PB10 |
| INSERM (France) | OSCAR; STR-I-155-HD; STR-I-171-GLA; STR-I-189-FRAXA; STR-I-203-CFTR; STR-I-209-MEN2a; STR-I-211-MEN2a; STR-I-221-Sca2; STR-I-229-MTMX; STR-I-231-MTMX; STR-I-233-FRAXA; STR-I-251-CFTR; STR-I-301-MFS; STR-I-305-APC; STR-I-315-CMT1a; STR-I-347-FRAXA; STR-I-355-APC; STR-I-359-APC |
| Masaryk University (Czech Republic) | CCTL 6; CCTL 8; CCTL 9; CCTL 10; CCTL 12; CCTL 13; CCRL 14 |
| Aalborg University (Denmark) | CLS1; CLS2; CLS3; CLS4 |
| University of Copenhagen (Denmark) | LRB001; LRB002; LRB003; LRB004; LRB005; LRB006; LRB007; LRB008; LRB009; LRB010; LRB011; LRB013; LRB014; LRB016; LRB017; LRB018; |
| University of Southern Denmark | KMEB1; KMEB2; KMEB3; KMEB4; KMEB |
| University of Helsinki (Finland) | FES21; FES22; FES29; FES30; FES61; FES75 |
| University of Tampere (Finland) | Regea 06/015; Regea 06/040; Regea 07/027; Regea 07/046; Regea 08/013; Regea 08/017; Regea 08/023; Regea 08/056 |
| Leiden University Medical Center (Netherlands) | HESC-NL1; HESC-NL2; HESC-NL3; HESC-NL4 |
| Russian Academy of Sciences (Russia) | ESM01; ESM02; ESM03; |
| Instanbul Memorial Hospital (Turkey) | MINE: NS-2; NS-3; NS-4; NS-5; NS-6; NS-7; NS-8; NS-9; NS-10; OZ-1; OZ-2; OZ-3; OZ-4; OZ-5; OZ-6; OZ-7; OZ-8 |
| Australia | |
| Monash University (Australia) | Envy |
| Prince of Wales Hospital, Sydney (Australia) | E1C1; E1C2; E1C3; E1C4; Endeavour 1; Endeavour 2; hES3.1; hES3.2; hES3.3 |
| Sydney IVF Limited (Australia) | SIVF01; SIVF03; SIVF05; SIVF06; SIVF07; SIVF08; SIVF09; SIVF10; SIVF11; SIVF12; SIVF13 |
| Asia | |
| Kyoto University (Japan) | 201B1; 201B2; 201B3; 201B6; 201B7; 243H1; 243H7; 246G1; 246G3; 246G4; 246G5; 246G6; khES-1; khES-2; khES-3; |
| Singapore Stem Cell Consortium | ESI-013; ESI-014; ESI-017; ESI-027; ESI-035; ESI-049; ESI-051; ESI-053 |
| ES Cell International Pte Ld (Singapore) | ES01, ES02, ES03, ES04, ES05, ES06 (HES-1, HES-2, HES-3, HES-4, HES-5, HES-6 |
| Maria Biotech Co. Ltd. - Maria Infertility Hospital Medical Institute, Seoul (Korea) | MB01; MB02; MB03; MB04; MB05; MB06; MB07; MB08; MB09 |
| MizMedi Hospital-Seoul National University, Seoul (Korea) | MI01 (Miz-hES1); Miz-hES2; Miz-hES3; Miz-hES4; Miz-hES5; Miz-hES6; Miz-hES7; Miz-hES8; Miz-hES9; Miz-hES10; Miz-hES11; Miz-hES12; Miz-hES13; Miz-hES14; Miz-hES15; |
| Pochon CHA University College of Medicine (Korea) | CHA-hES3; CHA-hES4 |
| Seoul National University (Korea) | SNUhESl; SNUhES2; SNUhES3; SNUhES4; SNUhES11; SNUhES16 |
| National Centre for Biological Sciences/Tata Institute of Fundamental Research, Bangalore (India) | NC01, NC02, NC03 (FCNCBS1, FCNCBS2, FCNCBS3); BJN-hem19; BJN-hem20 |
| Reliance Life Sciences, Mumbai (India) | RL05, RL07, RL10, RL13, RL15, RL20, RL21 (RLS ES 05, RLS ES 07, RLS ES 10, |
| National Institute for Research in Reproductive Health (India) | KIND-1; KIND-2 |
| Tata Institute of Fundamental Research (India) | FCNCBS1; FCNCBS2; FCNCBS3 |
| Kaohsiung Medical University (Taiwan) | T1; T2; T3; T4; T5 |
| Central South University (China) | chESC-3 (H3); chESC-8; chESC-20; chESC-22; EBNA1 + H9 |
| Graduate University of Chinese Academy of Sciences (China) | hPES-1; hPES-2 |
| Huazhong University of Science and Technology (China) | hES-8; hES18 |
| Peking University Third Hospital (China) | B4; B7; PKU1; PKU2 |
| Shanghai Jiao Tong University School of Medicine (China) | SHhES1 |

TABLE 4-continued

Listing of human embryonic stem (hES) cell lines

| Institution (Country) | Name |
|---|---|
| Shanghei Second Medical University (China) | SH1; SH2; SH4; SH7; SH28; SH35; SH35a; SH38; SH39; SH42 |
| Sun Yat-sen University (China) | CHES-1; SYSU-1; SYSU-2 |
| Sun Yat-sen University Second Affiliated Hospital (China) | CHE-1; CHE-2; CHE-3 |
| The Third Affiliated Hospital of Guangzhou Medical College (China) | FY-hES-5; FY-hES-9; FY-hES-10; FY-hES-11 |

Pluripotent Dedifferentiated Somatic Cells

Recently, studies using certain nuclear reprogramming factors have allowed pluripotent stem cells or pluripotent-like stem cells to be derived from a patient's own somatic cells. These cells are also called induced pluripotent stem (iPS) cells. The present invention describes various iPS cell lines provided by Shinya Yamanaka, Kyoto University. However, other iPS cell lines, for example, those described by James Thomson et al. are by the invention herein. See U.S. Publication 20090047263, International Publication WO2005/80598, U.S. Publication 20080233610 and International Publication WO2008/11882, which are herein incorporated in their entirety by reference. Thus, as used herein, "induced pluripotent stem (iPS) cells" means cells having properties similar to other pluripotent stem cells, e.g., hES cells, hEG cells, pPS (primate pluripotent stem) cells, parthenogenic cells and the like.

Nuclear programming factors are described in U.S. Patent Application Publication No. 2009/0047263, International Patent Application Publication No. WO2005/80598, U.S. Patent Application Publication No. 2008/0233610 and International Patent Application Publication No. WO2008/11882 and were used to induce reprogramming of a differentiated cell without using eggs, embryos, or ES cells. Methods for preparing induced iPS cells from somatic cells by using the nuclear reprogramming factor similar to that used and described in the present invention are not particularly limited. In preferred embodiments, the nuclear reprogramming factor contacts the somatic cells under an environment in which the somatic cells and induced pluripotent stem cells can proliferate. An advantage of the certain embodiments described herein is that an induced pluripotent stem cell can be prepared by contacting a nuclear reprogramming factor with a somatic cell in the absence of eggs, embryos, or embryonic stem (ES) cells. By using a nuclear reprogramming factor, the nucleus of a somatic cell can be reprogrammed to obtain an iPS cell or an "ES-like cell."

Pluripotent stem cells described herein, whether it be hES cells or iPS cells, may express any number of pluripotent cell markers, including but not limited to: alkaline phosphatase (AP); ABCG2; stage specific embryonic antigen-1 (SSEA-1); SSEA-3; SSEA-4; TRA-1-60; TRA-1-81; Tra-2-49/6E; ERas/ECAT5, E-cadherin; .β.III-tubulin; .alpha.-smooth muscle actin (.alpha.-SMA); fibroblast growth factor 4 (Fgf4), Cripto, Dax1; zinc finger protein 296 (Zfp296); N-acetyltransferase-1 (Nat1); (ES cell associated transcript 1 (ECAT1); ESG1/DPPA5/ECAT2; ECAT3; ECAT6; ECAT7; ECAT8; ECAT9; ECAT10; ECAT15-1; ECAT15-2; Fthl17; Sal14; undifferentiated embryonic cell transcription factor (Utf1); Rex1; p53; G3PDH; telomerase, including TERT; silent X chromosome genes; Dnmt3a; Dnmt3b; TRIM28; F-box containing protein 15 (Fbx15); Nanog/ECAT4; Oct3/4; Sox2; Klf4; c-Myc; Esrrb; TDGF1; GABRB3; Zfp42, FoxD3; GDF3; CYP25A1; developmental pluripotency-associated 2 (DPPA2); T-cell lymphoma breakpoint 1 (Tcl1); DPPA3/Stella; DPPA4 and the like. It is understood that the present invention is not limited to those markers listed herein, and encompasses markers such as cell surface markers, antigens, and other gene products including ESTs, RNA (including microRNAs and antisense RNA), DNA (including genes and cDNAs), and portions thereof.

In one embodiment, the iPS cell lines used herein contain the following nuclear reprogramming factor genes: an Oct family gene, a Klf family gene, and a Sox family gene. In one iPS cell line, each of the following three kinds of genes are provided: Oct3/4, Klf4, and Sox2. Other iPS cell lines gene products of each of the following three kinds of genes were employed: an Oct family gene, a Klf family gene, and a Myc family gene, e.g., Oct3/4, Klf4 and c-Myc. Accordingly, it is understood that the nuclear reprogramming factor can be with or without the Myc family gene.

The nuclear reprogramming factors described herein and also known in the art, can be used to generate iPS cells from differentiated adult somatic cells, and is not limited by the type of somatic cells to be reprogrammed, i.e., any kind of somatic cell may be reprogrammed or dedifferentiated. Because reprogramming a somatic does not require an egg and/or embryo, an iPS cell can be a mammalian cell, therefore, providing an opportunity to generate patient- or disease-specific pluripotent stem cells.

Aggregate Suspension of Pluripotent Stem Cells

In contrast to previously known methods of tissue engineering which are based on seeding individual cells into polymer scaffolds, matrices and/or gels, embodiments described herein can use cell aggregate suspensions formed from pluripotent stem cell, single cell suspensions or differentiated single cell suspensions derived therefrom. Methods of processing and/or manufacturing of stem cell aggregate suspension and differentiation of cells thereof is described in International Applications PCT/US2007/062755 and PCT/US2008/082356, which are herein incorporated by reference in their entireties.

In one embodiment, methods are provided for producing pluripotent stem cell aggregate suspensions from a single cell suspension of pluripotent stem cell cultures, e.g. hES or iPS cell cultures. The pluripotent stem cell can be initially cultured on fibroblast feeders or can be feeder-free. Methods of isolating hES cells and culturing such on human feeder cells is described in U.S. Pat. No. 7,432,104, which is herein incorporated in its entirety by reference.

As used herein, "single cell suspension" or equivalents thereof refers to a pluripotent, multipotent or terminally differentiated single cell suspension, or a single cell suspension derived from a pluripotent or multipotent cell, by any mechanical or chemical means. Several methods exist for dissociating cell clusters to form single cell suspensions from primary tissues, attached cells in culture, and aggregates, e.g., physical forces (mechanical dissociation such as cell scraper, trituration through a narrow bore pipette, fine needle aspiration, vortex disaggregation and forced filtration through a fine nylon or stainless steel mesh), enzymes (enzymatic dissociation such as trypsin, collagenase, Accutase™ and the like), or a combination of both. Further, methods and culture media conditions capable of supporting single-cell dissociation of pluripotent, multipotent or differentiated cells are useful for expansion, cell sorting, and defined seeding for multi-well plate assays and enable automatization of culture procedures and clonal expansion.

Other embodiments provide for methods of producing pluripotent stem cell aggregate suspensions directly into a differentiation media, e.g., a differentiating media containing an agent, preferably a TGFβ family member, which is capable of activating a TGFβ family of receptor, e.g., Activin A, Activin B, GDF-8, GDF-11, and Nodal. Growth factors for production of endoderm is described in International Application No., PCT/US2008/065686, which is herein incorporated by reference in its entirety. Methods of producing cell aggregate suspension in a differentiation media can be distinguished from other methods, also described herein, which provide for production of cell aggregate suspension cultures in a pluripotent stem cell media, e.g., StemPro® hES SFM (Invitrogen) based on the heregulin-based DC-HAIF media described in PCT/US2007/062755.

Embodiments described herein relate to methods for generating a pluripotent cell aggregate in suspension from a pluripotent adherent culture, by culturing a pluripotent cell in an adherent growth culture condition which allows for expansion in an undifferentiated state; disassociating the adherent pluripotent cell culture into a single cell suspension culture; contacting the single cell suspension culture with a first differentiating culture condition which allows for formation of hES-derived cell aggregates in suspension by agitating the single cell suspension culture until such a period of time when the single cell suspension culture forms a pluripotent-derived cell aggregate in suspension, and thereby generating a pluripotent-derived cell aggregate in suspension. In preferred embodiments, agitation of the single cell suspension culture is performed by rotation at about 80 rpm to 160 rpm. In certain other embodiments described herein, a rho-kinase inhibitor is used to facilitate pluripotent stem cell aggregation, growth, proliferation, expansion and/or cell mass.

Embodiments described herein also relate to methods for generating a pluripotent-derived cell aggregate in suspension from a pluripotent-derived single cell suspension, by culturing a hES cell in an adherent growth culture condition which allows for expansion in an undifferentiated state; contacting the undifferentiated hES cell with a first differentiating culturing condition suitable for differentiating the hES cell and resulting in an adherent pluripotent-derived cell; disassociating the adherent hES-derived cell into a single cell suspension culture; contacting the single cell suspension culture with a second differentiating culture condition which allows for formation of hES-derived cell aggregates in suspension by agitating the single cell suspension culture until such a period of time when the single cell suspension culture forms a pluripotent-derived cell aggregate in suspension, and thereby generating a pluripotent-derived cell aggregate in suspension. In preferred embodiments, agitation of the single cell suspension culture is performed by rotation at about 80 rpm to 160 rpm.

In preferred embodiments, manufacturing-scale suspension cultures utilize continuous perfusion of media as a method for maintaining cell viability while maximizing cell density. In this context, media exchange contributes fluid shear to the culture affecting adherent cells and suspended aggregates differently. Immobile adherent cells are subject to fluid shear stress as the media flows tangentially across the cell surface. In contrast, suspended aggregates experience significantly less shear stress across the aggregate surface, as aggregates are free to tumble in response to applied shear force. It is expected that prolonged shear stress will be detrimental to adherent pluripotent cells and that the suspended aggregate format is preferred for optimal survival and function. Thus, based on a need for an efficient manufacturing process for production of pluripotent stem cells and/or multipotent progenitor cells derived from pluripotent stem cells and the above observed mechanics relating to shear rate and shear stress, embodiments described herein provide, for the first time, methods of manufacturing for the production of pluripotent stem cells and/or multipotent progenitor cells derived from pluripotent stem cells in suspension format, in particular, cell aggregate suspension format.

In yet another embodiment, hES cell aggregate suspensions were cultured in a media substantially free of serum and further in the absence of exogenously added fibroblast growth factor (FGF). This is distinguished from U.S. Pat. No. 7,005,252 to Thomson, J., which requires culturing hES cells in a media without serum but containing exogenously added growth factors, including FGF. In some embodiments, iPS cell aggregate suspensions are cultured in a media substantially free of serum and/or further in the absence of exogenously added fibroblast growth factor (FGF).

In contrast to cell aggregates produced by previously known methods that may vary in both size and shape, the cell aggregates and methods described herein have a narrow size and shape distribution, i.e., the cell aggregates are substantially uniform in size and/or shape. The size uniformity of the cell aggregates is critical for differentiation performance and the culture homogeneity. Applying basic mass transport analysis to the aggregates, it is expected that diffusion of oxygen and nutrients into the center of large aggregates will be slow compared to diffusion into smaller aggregates, assuming equal permeability. As differentiation of aggregated ES cells, or iPS cells, into pancreatic lineage cells is dependent on the temporal application of specific growth factors, a culture with a mixture of aggregates of different diameters is likely to be de-synchronized as compared to a uniform (size and shape) culture of cell aggregates. This mixture of cell aggregates gives rise to heterogeneity and may result in poor differentiation performance and ultimately not lend itself to being amenable to manufacturing, scale-up, and production. Hence, as used herein, the phrase "substantially uniform" or "substantially uniform in size and shape" or equivalents thereof, refers to the spread in uniformity of the aggregates and is not more than about 20%. In another embodiment, the spread in uniformity of the aggregates is not more than about 15%, 10% or 5%.

Although the exact number of cells per aggregate is not critical, it will be recognized by those skilled in the art that the size of each aggregate (and thus the number of cells per aggregate) is limited by the capacity of oxygen and nutrients to diffuse to the central cells, and that this number may also vary depending on cell type and the nutritive requirements of that cell type. Cell aggregates may comprise a minimal number of cells (e.g., two or three cells) per aggregate, or may comprise many hundreds or thousands of cells per aggregate. Typically, cell aggregates comprise hundreds to thousands of cells per aggregate. For purposes of the present invention, the cell aggregates are typically from about 50 microns to about 600 microns in size, although, depending on cell type, the size may be less or greater than this range. In one embodiment, the cell aggregates are from about 50 microns to about 250 microns in size, or about 75 to 200 microns in size, and preferably they are about 100 to 150 microns in size.

Still other methods describe making embryoid bodies (EBs). As used herein, the term "embryoid bodies", "aggregate bodies" or equivalents thereof, refer to aggregates of differentiated and undifferentiated cells that appear when ES cells overgrow in monolayer cultures, or are maintained in suspension cultures in undefined media or are differentiated via non-directed protocols towards multiple germ layer tissues. That is, EBs are not formed from a single cell suspension of pluripotent stem cells as described herein; nor are EBs formed from adherent cultures of pluripotent-derived multipotent cells. These features alone make the present invention clearly distinguished from an embryoid body.

In contrast to embryoid bodies, which are a mixture of differentiated and undifferentiated cells and typically consist of cells from several germ layers and go through random differentiation, the cell aggregates described herein are essentially or substantially homo-cellular, existing as aggregates of pluripotent, multipotent, bipotent, or unipotent type cells, e.g., embryonic cells, definitive endoderm, foregut endoderm, PDX1 positive pancreatic endoderm, pancreatic endocrine cells and the like.

Embodiments described herein address the above problems by providing a cost efficient manufacturing process or methods capable of reproducibly producing cell aggregates that are substantially uniform in size and shape using a process that can easily be applied to large-scale manufacturing. In one particular embodiment, the differentiable cells are expanded in a suspension culture, using the cell media of the present invention. In another particular embodiment, the differentiable cells can be maintained and expanded in suspension, i.e., they remain undifferentiated or are prevented from further differentiating. The term "expand" in the context of cell culture is used as it is in the art, and refers to cellular proliferation and increase the number of cells, preferably increase in number of viable cells. In a specific embodiment, the cells are expanded in a culture suspension by culturing for more than about one day, i.e., about 24 hours. In a more specific embodiment, the cells are expanded in a suspension culture by culturing for at least 1, 2, 3, 4, 5, 6, 7 days, or at least 2, 3, 4, 5, 6, 7, 8 weeks.

Still other embodiments of the invention provide for methods of producing cell aggregate suspensions formed from differentiated pluripotent stem cell cultures e.g., cells produced from the pluripotent cells described herein, and including cells from stages 1, 2, 3, 4 and 5 as described in d'Amour 2005 and 2006, supra. Hence, methods for making the cell aggregates described herein are not limited to any one pluripotent or multipotent cell or cell stage, rather the manner of use and need for cell type optimization will dictate which methods are preferred.

The methods described herein for producing aggregate suspension cultures of pluripotent cells, e.g., hES or iPS cells, and cells derived from other pluripotent cell sources, for example, embryonic germ or parthenote cells, are substantially as described in PCT/US2007/062755, filed Feb. 23, 2007, and titled Compositions and methods for culturing differential cells and PCT/US2008/080516, filed Oct. 20, 2008, and titled Methods and compositions for feeder-free pluripotent stem cell media containing human serum, which are herein incorporated by reference in their entireties.

The methods described herein in no way require first coating the culturing vessels with an extracellular matrix, e.g., as described in U.S. Pat. No. 6,800,480 to Bodnar et al. and assigned to Geron Corporation. In some embodiments described herein, iPS cells can be cultured in the same way that other pluripotent stem cells, e.g., hES and iPS cells, are cultured using soluble human serum as substantially described in U.S. Application, PCT/US2008/080516, filed Oct. 20, 2008, and titled Methods and compositions for feeder-free pluripotent stem cell media containing human serum, which is herein incorporated by reference in its entirety.

The methods described herein in no way require exogenously added fibroblast growth factor (FGF) supplied from a source other than just a fibroblast feeder layer as described in U.S. Pat. No. 7,005,252 to Thomson, J. and assigned to the Wisconsin Alumni Research Foundation (WARF), which is herein incorporated by reference in its entirety.

Multipotent and Differentiated Cell Compositions

Cell compositions produced by the methods described herein include cell cultures comprising pluripotent stem cells, preprimitive streak, mesendoderm, definitive endoderm, foregut endoderm, PDX1-positive foregut endoderm, PDX1-positive pancreatic endoderm or PDX1/NKX6.1 co-positive pancreatic endoderm, endocrine precursor or NGN3/NKX2.2 co-positive endocrine precursor, and hormone secreting endocrine cells or INS, GCG, GHRL, SST, PP singly-positive endocrine cells, wherein at least about 5-90% of the cells in culture are the preprimitive streak, mesendoderm, definitive endoderm, foregut endoderm, PDX1-positive foregut endoderm, PDX1-positive pancreatic endoderm or PDX1/NKX6.1 co-positive pancreatic endoderm, endocrine precursor or NGN3/NKX2.2 co-positive endocrine precursor, and hormone secreting endocrine cells or INS, GCG, GHRL, SST, PP singly-positive endocrine cells produced.

Some embodiments described herein relate to compositions, such as cell populations and cell cultures that comprise both pluripotent cells, such as stem cells and iPS cells, and multipotent cells, such as preprimitive streak, mesendoderm or definitive endoderm, as well as more differentiated, but still potentially multipotent, cells, such as PDX1-positive foregut endoderm, PDX1-positive pancreatic endoderm or PDX1/NKX6.1 co-positive pancreatic endoderm, endocrine precursor or NGN3/NKX2.2 co-positive endocrine precursor, and hormone secreting endocrine cells or INS, GCG, GHRL, SST, PP singly-positive endocrine cells. For example, using the methods described herein, compositions comprising mixtures of pluripotent stem cells and other multipotent or differentiated cells can be produced. In some embodiments, compositions comprising at least about 5 multipotent or differentiated cells for about every 95 pluripotent cells are produced. In other embodiments, compositions comprising at least about 95 multipotent or differentiated cells for about every 5 pluripotent cells are produced. Additionally, compositions comprising other ratios of multipotent or differentiated cells to pluripotent cells are contemplated. For example, compositions comprising at least about 1 multipotent or differentiated cell for about every 1,000,000 pluripotent cells, at least about 1 multipotent or differentiated cell for about every 100,000 pluripotent cells, at least about 1 multipotent or differentiated cell for about every 10,000 pluripotent cells, at least about 1 multipotent or differentiated cell for about every 1000 pluripotent cells, at least about 1 multipotent or differentiated cell for about every 500 pluripotent cells, at least about 1 multipotent or differentiated cell for about every 100 pluripotent cells, at least about 1 multipotent or differentiated cell for about every 10 pluripotent cells, at least about 1 multipotent or differentiated cell for about every 5 pluripotent cells, and up to about every 1 pluripotent cell and at least about 1,000,000 multipotent or differentiated cell for about every 1 pluripotent cell are contemplated.

Some embodiments described herein relate to cell cultures or cell populations comprising from at least about 5% multipotent or differentiated cell to at least about 99% multipotent or differentiated cells. In some embodiments the cell cultures or cell populations comprise mammalian cells. In preferred embodiments, the cell cultures or cell populations comprise human cells. For example, certain specific embodiments relate to cell cultures comprising human cells, wherein from at least about 5% to at least about 99% of the human cells are multipotent or differentiated cell. Other embodiments relate to cell cultures comprising human cells, wherein at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, at least about 99%, or greater than 99% of the human cells are multipotent or differentiated cells. In embodiments where the cell cultures or cell populations comprise human feeder cells, the above percentages are calculated without respect to the human feeder cells in the cell cultures Pluripotent, multipotent or differentiated cells are capable of differentiating, or further differentiating, into preprimitive streak, mesendoderm, definitive endoderm cells as well as cells, tissues and/or organs derived therefrom. Mesendoderm cells are capable of differentiating into mesoderm cells and/or definitive endoderm cells as well as cells, tissues and/or organs derived from either of these lineages. In some embodiments, the preprimitive streak cells are converted, through a mesendoderm intermediate, into terminally differentiated cells of either the mesoderm or definitive endoderm lineages. For example, such processes can provide the basis for efficient production of human endodermal derived tissues, such as pancreas, liver, lungs, stomach, intestine, thyroid, parathyroid, thymus, pharynx, gallbladder and urinary bladder. Importantly, production of preprimitive streak cells and/or mesendoderm cells is an early step in differentiation of a pluripotent stem cell to a functional insulin-producing β-cell. As another example, preprimitive streak cell and/or mesendoderm cell differentiation can provide the basis for efficient production of human mesodermal derived tissues, such as blood cells, cardiovascular tissues, skeletal tissues as well as other structural and connective tissues.

The compositions and methods described herein have several useful features. For example, the cell cultures and cell populations comprising, multipotent cells, e.g., preprimitive streak cells and/or mesendoderm cells as well as the methods for producing such cell cultures and cell populations, are useful for modeling the early stages of human development. Furthermore, the compositions and methods described herein can also serve for therapeutic intervention in disease states, such as diabetes mellitus. For example, since preprimitive streak cells and/or mesendoderm cells serve as the source for only a limited number of tissues, they can be used in the development of pure tissue or cell types. In some processes for producing preprimitive streak cells, the pluripotent cells used as starting material are pluripotent stem cells, e.g., hES, hEG or iPS cells.

Trophectoderm Cells

Using the methods described herein, compositions comprising trophectoderm cells substantially free of other cell types can be produced. In some embodiments described herein, the trophectoderm cell populations or cell cultures produced by the methods described herein substantially have high expression of markers selected from the group consisting of HAND1, Eomes, MASH2, ESXL1, HCG, KRT18, PSG3, SFXN5, DLX3, PSX1, ETS2, and ERRB genes as compared to the expression levels of HAND1, Eomes, MASH2, ESXL1, HCG, KRT18, PSG3, SFXN5, DLX3, PSX1, ETS2, and ERRB in non-trophectoderm cells or cell populations.

Preprimitive Streak Cells

Using the methods described herein, compositions comprising preprimitive streak cells substantially free of other cell types can be produced. In some embodiments described herein, the preprimitive streak cell populations or cell cultures produced by the methods described herein are substantially express FGF8 and/or NODAL marker genes as compared to BRACHURYlow, FGF4 low, SNAI1 low, SOX17 low, FOXA2 low, SOX7 low and SOX1 low.

Extraembryonic Cells

Using the methods described herein, compositions comprising extraembryonic cells substantially free of other cell types can be produced. Primitive, visceral and parietal endoderm cells are extraembryonic cells. Primitive endoderm cells give rise to visceral and parietal endoderm cells. Visceral endoderm cells are endoderm cells that form part of the yolk sac. Visceral endoderm cells function in both nutrient uptake and transport. Parietal endoderm cells are contiguous with an extraembryonic tissue known as Reichert's membrane. One of the roles of parietal endoderm cells is to produce basement membrane components. Together, visceral endoderm cells and parietal endoderm cells form what is often referred to as extraembryonic endoderm. As the name suggests, extraembryonic endoderm cells do not give rise to embryonic structures formed during development. In contrast, definitive endoderm cells and other endoderm-lineage or pancreatic-lineage cells described herein are embryonic or derived from embryonic cells and give rise to tissues that are derived from the gut tube that forms during embryonic development. In some embodiments described herein, the extraembryonic cell populations or cell cultures produced by the methods described herein substantially have high expression of markers selected from the group consisting of SOX7, SOX17, THBD, SPARC, DAB1, HNF4alpha or AFP genes as compared to the expression levels of at least SOX7, SOX17, THBD, SPARC, DAB1, or AFP, which is not expressed in other types of cells or cell populations, for example, definitive endoderm.

Mensendoderm Cells

Using the methods described herein, compositions comprising mesendoderm cells substantially free of other cell types can be produced. In some embodiments described herein, the mesendoderm cell populations or cell cultures produced by the methods described herein substantially have high expression of markers selected from the group consisting of FGF4, SNAI1 MIXL1 and/or WNT3 marker genes, as compared to SOX17 low, CXCR4 low, FOXA2 low, SOX7 low and SOX1 low.

Screening Methods

In some embodiments, screening methods are employed to obtain certain cell populations comprising pluripotent, multipotent and/or differentiated cells, such as human pluripotent stem cells, induced pluripotent stem cells, preprimitive streak cells, mensendoderm cells, definitive endoderm cells, foregut endoderm or PDX1-negative foregut endoderm cells, PDX1-positive foregut endoderm or PDX1-positive pancreatic endoderm cells or pancreatic progenitor cells, endocrine precursor cells, and/or endocrine cells. The cell population is then provided with a candidate differentiation factor. At a first time point, which is prior to or at approximately the same time as providing the candidate differentiation factor, expression of a marker is determined. Alternatively, expression of the marker can be determined after providing the candidate differentiation factor. At a second time point, which is subsequent to the first time point and subsequent to the step of providing the candidate differentiation factor to the cell population, expression of the same marker is again determined Whether the candidate differentiation factor is capable of promoting the differentiation of the pancreatic precursor cells is determined by comparing expression of the marker at the first time point with the expression of the marker at the second time point. If expression of the marker at the second time point is increased or decreased as compared to expression of the marker at the first time point, then the candidate differentiation factor is capable of promoting the differentiation of pancreatic progenitor cells.

Some embodiments of the screening methods described herein utilize cell populations or cell cultures which comprise human definitive endoderm, PDX-1 negative foregut endoderm, PDX-1 positive foregut endoderm, PDX-1 positive pancreatic endoderm, or pancreatic progenitor or endocrine precursor cells. For example, the cell population can be a substantially purified population of PDX-1-positive pancreatic endoderm or pancreatic progenitor cells. For example, the cell population can be an enriched population of human pancreatic progenitor cells, wherein at least about 50% to 97% of the human cells in the cell population are human pancreatic progenitor cells, the remainder comprising of endocrine precursor or endocrine cells and other cell types.

In embodiments of the screening methods described herein, the cell population is contacted or otherwise provided with a candidate (test) differentiation factor. The candidate differentiation factor can comprise any molecule that may have the potential to promote the differentiation of any of the above-mentioned cells, e.g. human pancreatic progenitor cells. In some embodiments described herein, the candidate differentiation factor comprises a molecule that is known to be a differentiation factor for one or more types of cells. In alternate embodiments, the candidate differentiation factor comprises a molecule that is not known to promote cell differentiation. In preferred embodiments, the candidate differentiation factor comprises a molecule that is not known to promote the differentiation of human pancreatic progenitor cells.

In some embodiments of the screening methods described herein, the candidate differentiation factor comprises a small molecule. In preferred embodiments, a small molecule is a molecule having a molecular mass of about 10,000 amu or less.

In other embodiments described herein, the candidate differentiation factor comprises a large molecule, e.g., a polypeptide. The polypeptide can be any polypeptide including, but not limited to, a glycoprotein, a lipoprotein, an extracellular matrix protein, a cytokine, a chemokine, a peptide hormone, an interleukin or a growth factor. Preferred polypeptides include growth factors.

In some embodiments of the screening methods described herein, the candidate differentiation factors comprise one or more growth factors selected from the group consisting of Amphiregulin, B-lymphocyte stimulator, IL-16, Thymopoietin, TRAIL/Apo-2, Pre B cell colony enhancing factor, Endothelial differentiation-related factor 1 (EDF1), Endothelial monocyte activating polypeptide II, Macrophage migration inhibitory factor (MIF), Natural killer cell enhancing factor (NKEFA), Bone morphogenetic protein 2, Bone morphogenetic protein 8 (osteogeneic protein 2), Bone morphogenic protein 6, Bone morphogenic protein 7, Connective tissue growth factor (CTGF), CGI-149 protein (neuroendocrine differentiation factor), Cytokine A3 (macrophage inflammatory protein 1-alpha), Gliablastoma cell differentiation-related protein (GBDR1), Hepatoma-derived growth factor, Neuromedin U-25 precursor, Vascular endothelial growth factor (VEGF), Vascular endothelial growth factor B (VEGF-B), T-cell specific RANTES precursor, thymic dendritic cell-derived factor 1, Transferrin, Interleukin-1 (IL 1), Interleukin-2 (IL 2), Interleukin-3 (IL 3), Interleukin-4 (IL 4), Interleukin-5 (IL 5), Interleukin-6 (IL 6), Interleukin-7 (IL 7), Interleukin-8 (IL 8), Interleukin-9 (IL 9), Interleukin-10 (IL 10), Interleukin-11 (IL 11), Interleukin-12 (IL 12), Interleukin-13 (IL 13), Granulocyte-colony stimulating factor (G-CSF), Granulocyte macrophage colony stimulating factor (GM-CSF), Macrophage colony stimulating factor (M-CSF), Erythropoietin, Thrombopoietin, Vitamin D3, Epidermal growth factor (EGF), Brain-derived neurotrophic factor, Leukemia inhibitory factor, Thyroid hormone, Basic fibroblast growth factor (bFGF), aFGF, FGF-4, FGF-6, FGF-7/Keratinocyte growth factor (KGF), Platelet-derived growth factor (PDGF), Platelet-derived growth factor-BB, β nerve growth factor, activin A, Transforming growth factor β1 (TGFβ1), Interferon-α, Interferon-β, Interferon-γ, Tumor necrosis factor-α, Tumor necrosis factor-β, Burst promoting activity (BPA), Erythroid promoting activity (EPA), PGE2, insulin growth factor-1 (IGF-1), IGF-II, Neutrophin growth factor (NGF), Neutrophin-3, Neutrophin 4/5, Ciliary neurotrophic factor, Glial-derived nexin, Dexamethasone, β-mercaptoethanol, Retinoic acid, Butylated hydroxyanisole, 5-azacytidine, Amphotericin B, Ascorbic acid, Ascrorbate, isobutylxanthine, indomethacin, β-glycerolphosphate, nicotinamide, DMSO, Thiazolidinediones, TWS119, oxytocin, vasopressin, melanocyte-stimulating hormone, corticortropin, lipotropin, thyrotropin, growth hormone, prolactin, luteinizing hormone, human chorionic gonadotropin, follicle stimulating hormone, corticotropin-releasing factor, gonadotropin-releasing factor, prolactin-releasing factor, prolactin-inhibiting factor, growth-hormone releasing factor, somatostatin, thyrotropin-releasing factor, calcitonin gene-related peptide, parathyroid hormone, glucagon-like peptide 1, glucose-dependent insulinotropic polypeptide, gastrin, secretin, cholecystokinin, motilin, vasoactive intestinal peptide, substance P, pancreatic polypeptide, peptide tyrosine, neuropeptide tyrosine, insulin, glucagon, placental lactogen, relaxin, angiotensin II, calctriol, atrial natriuretic peptide, and melatonin. thyroxine, triiodothyronine, calcitonin, estradiol, estrone, progesterone, testosterone, cortisol, corticosterone, aldosterone, epinephrine, norepinepherine, androstiene, calcitriol, collagen, Dexamethasone, β-mercaptoethanol, Retinoic acid, Butylated hydroxyanisole, 5-azacytidine, Amphotericin B, Ascorbic acid, Ascrorbate, isobutylxanthine, indomethacin, β-glycerolphosphate, nicotinamide, DMSO, Thiazolidinediones, and TWS119.

In some embodiments of the screening methods described herein, the candidate differentiation factor is provided to the cell population in one or more concentrations. In some embodiments, the candidate differentiation factor is provided to the cell population so that the concentration of the candidate differentiation factor in the medium surrounding the cells ranges from about 0.1 ng/ml to 10 mg/ml. In some embodiments, the concentration of the candidate differentiation factor in the medium surrounding the cells ranges from about 1 ng/ml to about 1 mg/ml. In other embodiments, the concentration of the candidate differentiation factor in the medium surrounding the cells ranges from about 10 ng/ml to about 100 μg/ml. In still other embodiments, the concentration of the candidate differentiation factor in the medium surrounding the cells ranges from about 100 ng/ml to about 10 µg/ml. In preferred embodiments, the concentration of the candidate differentiation factor in the medium surrounding the cells ranges from about 5 ng/ml to 1000 µg/ml.

In some embodiments, steps of the screening methods described herein comprise determining expression of at least one marker at a first time point and a second time point. In some of these embodiments, the first time point can be prior to or at approximately the same time as providing the cell population with the candidate differentiation factor. Alternatively, in some embodiments, the first time point is subsequent to providing the cell population with the candidate differentiation factor. In some embodiments, expression of a plurality of markers is determined at a first time point.

In addition to determining expression of at least one marker at a first time point, some embodiments of the screening methods described herein contemplate determining expression of at least one marker at a second time point, which is subsequent to the first time point and which is subsequent to providing the cell population with the candidate differentiation factor. In such embodiments, expression of the same marker is determined at both the first and second time points. In some embodiments, expression of a plurality of markers is determined at both the first and second time points. In such embodiments, expression of the same plurality of markers is determined at both the first and second time points. In some embodiments, marker expression is determined at a plurality of time points, each of which is subsequent to the first time point, and each of which is subsequent to providing the cell population with the candidate differentiation factor. In certain embodiments, marker expression is determined by Q-PCR. In other embodiments, marker expression is determined by immunocytochemistry.

In certain embodiments of the screening methods described herein, the marker having its expression determined at the first and second time points is a marker that is associated with the differentiation of pancreatic progenitor cells to cells which are the precursors of terminally differentiated cells which make up pancreatic islet tissues. Such cells can include immature pancreatic islet hormone-expressing cells.

In some embodiments of the screening methods described herein, sufficient time is allowed to pass between providing the cell population with the candidate differentiation factor and determining marker expression at the second time point. Sufficient time between providing the cell population with the candidate differentiation factor and determining expression of the marker at the second time point can be as little as from about 1 hour to as much as about 10 days. In some embodiments, the expression of at least one marker is determined multiple times subsequent to providing the cell population with the candidate differentiation factor. In some embodiments, sufficient time is at least about 1 hour, at least about 6 hours, at least about 12 hours, at least about 16 hours, at least about 1 day, at least about 2 days, at least about 3 days, at least about 4 days, at least about 5 days, at least about 6 days, at least about 7 days, at least about 8 days, at least about 9 days, at least about 10 days, at least about 11 days, at least about 12 days, at least about 13 days, at least about 14 days, at least about 1 week, at least about 2 weeks, at least about 3 weeks, at least about 4 weeks, at least about 5 weeks, at least about 6 weeks, at least about 7 weeks, or at least about 8 weeks.

In some embodiments of the methods described herein, it is further determined whether the expression of the marker at the second time point has increased or decreased as compared to the expression of this marker at the first time point. An increase or decrease in the expression of the at least one marker indicates that the candidate differentiation factor is capable of promoting the differentiation of the endocrine precursor cells. Similarly, if expression of a plurality of markers is determined, it is further determined whether the expression of the plurality of markers at the second time point has increased or decreased as compared to the expression of this plurality of markers at the first time point. An increase or decrease in marker expression can be determined by measuring or otherwise evaluating the amount, level or activity of the marker in the cell population at the first and second time points. Such determination can be relative to other markers, for example housekeeping gene expression, or absolute. In certain embodiments, wherein marker expression is increased at the second time point as compared with the first time point, the amount of increase is at least about 2-fold, at least about 5-fold, at least about 10-fold, at least about 20-fold, at least about 30-fold, at least about 40-fold, at least about 50-fold, at least about 60-fold, at least about 70-fold, at least about 80-fold, at least about 90-fold, at least about 100-fold or more than at least about 100-fold. In some embodiments, the amount of increase is less than 2-fold. In embodiments where marker expression is decreased at the second time point as compared with the first time point, the amount of decrease is at least about 2-fold, at least about 5-fold, at least about 10-fold, at least about 20-fold, at least about 30-fold, at least about 40-fold, at least about 50-fold, at least about 60-fold, at least about 70-fold, at least about 80-fold, at least about 90-fold, at least about 100-fold or more than at least about 100-fold. In some embodiments, the amount of decrease is less than 2-fold.

Monitoring the Production of Multipotent or Differentiated Cells

The progression of pluripotent cells to multipotent cells to further multipotent cells or differentiated cells, such as pancreatic progenitors or hormone endocrine secreting cells, can be monitored by determining the expression of markers characteristic of the specific cells, including genetic markers and phenotypic markers such as, the expression of islet hormones and the processing of proinsulin into insulin and C peptide in endocrine cells. In some processes, the expression of certain markers is determined by detecting the presence or absence of the marker. Alternatively, the expression of certain markers can be determined by measuring the level at which the marker is present in the cells of the cell culture or cell population. For example, in certain processes, the expression of markers characteristic of immature pancreatic islet hormone-expressing cells as well as the lack of significant expression of markers characteristic of pluripotent cells, definitive endoderm, foregut endoderm, PDX1-positive foregut endoderm, endocrine precursor, extraembryonic endoderm, mesoderm, ectoderm, mature pancreatic islet hormone-expressing cells and/or other cell types is determined.

As described in connection with monitoring the production of other less differentiated cell types of the definitive endoderm lineage, qualitative or semi-quantitative techniques, such as blot transfer methods and immunocytochemistry, can be used to measure marker expression. Alternatively, marker expression can be accurately quantitated through the use of technique such as Q-PCR. Additionally, it will be appreciated that at the polypeptide level, many of the markers of pancreatic islet hormone-expressing cells are secreted proteins. As such, techniques for measuring extracellular marker content, such as ELISA, may be utilized.

For example, in one embodiment, PDX1 is a marker gene that is associated with PDX1-positive foregut endoderm. As such, in some embodiments of the present invention, the expression of PDX1 is determined. In other embodiments, the expression of other markers, which are expressed in PDX1-positive foregut endoderm, including, but not limited to, SOX17, HNF6, SOX9 and PROX1 is also determined. Since PDX1 can also be expressed by certain other cell types (that is, visceral endoderm and certain neural ectoderm), some embodiments of the present invention relate to demonstrating the absence or substantial absence of marker gene expression that is associated with visceral endoderm and/or neural ectoderm. For example, in some embodiments, the expression of markers, which are expressed in visceral endoderm and/or neural cells, including, but not limited to, SOX7, AFP, SOX1, ZIC1 and/or NFM is determined.

In some embodiments, PDX1-positive foregut endoderm cell cultures produced by the methods described herein are substantially free of cells expressing the SOX7, AFP, SOX1, ZIC1 or NFM marker genes. In certain embodiments, the PDX1-positive foregut endoderm cell cultures produced by the processes described herein are substantially free of visceral endoderm, parietal endoderm and/or neural cells.

The developmental progression of the pluripotent cells described herein (e.g., cells produced as a result of Stages or Steps 1-5 as described in D'Amour et al. 2006, supra) can be monitored by determining the expression of markers characteristic of each hES-derived or iPS-derived cell type along the developmental pathway. In some processes, the identification and characterization of a hES-derived or iPS-derived cell type is by expression of a certain marker or different expression levels and patterns of more than one marker. That is, the presence or absence, the high or low expression, of one or more the marker(s) typifies and identifies a cell-type. Also, certain markers can have transient expression, whereby the marker is highly expressed during one stage of development and poorly expressed in another stage of development. The expression of certain markers can be determined by measuring the level at which the marker is present in the cells of the cell culture or cell population as compared to a standardized or normalized control marker. In such processes, the measurement of marker expression can be qualitative or quantitative. One method of quantitating the expression of markers that are produced by marker genes is through the use of quantitative PCR (Q-PCR). Methods of performing Q-PCR are well known in the art.

In some embodiments of the present invention, the presence, absence and/or level of expression of a marker is determined by quantitative PCR (Q-PCR). For example, the amount of transcript produced by certain genetic markers, such as SOX17, CXCR4, OCT4, AFP, TM, SPARC, SOX7, CDX2, MIXL1, GATA4, HNF3β, HNF4alpha, GSC, FGF17, VWF, CALCR, FOXQ1, CMKOR1, CRIP1 and other markers described herein is determined by quantitative Q-PCR.

In other embodiments, immunohistochemistry is used to detect the proteins expressed by the above-mentioned genes. In still other embodiments, Q-PCR can be used in conjunction with immunohistochemical techniques or flow cytometry techniques to effectively and accurately characterize and identify cell types and determine both the amount and relative proportions of such markers in a subject cell type. In one embodiment, Q-PCR can quantify levels of RNA expression in a cell culture containing a mixed population of cells. However, Q-PCR cannot provide or qualify whether the subject markers or proteins are co-expressed on the same cell. In another embodiment, Q-PCR is used in conjunction with flow cytometry methods to characterize and identify cell types. Thus, by using a combination of the methods described herein, and such as those described above, complete characterization and identification of various cell types, including endoderm lineage type cells, can be accomplished and demonstrated.

For example, in one preferred embodiment, pancreatic progenitors or pancreatic endoderm or PDX-1 positive pancreatic endoderm, expresses at least PDX1, Nkx6.1, PTF1A, CPA and/or cMYC as demonstrated by Q-PCR and/or ICC, but such a cell at least co-expresses PDX1 and Nkx6.1 as demonstrated by ICC and does not express other markers including SOX17 CXCR4, or CER, to be identified as a PDX1-positive expressing cell. Similarly, for proper identification of a mature hormone secreting pancreatic cell, in vitro or in vivo, for example, there is demonstrated that C-peptide (a product of proper processing of pro-insulin in a mature and functioning β cell) and insulin are co-expressed by ICC in the insulin secreting cell.

Still, other methods which are known in the art can also be used to quantitate marker gene expression. For example, the expression of a marker gene product can be detected by using antibodies specific for the marker gene product of interest (e.g., e.g. Western blot, flow cytometry analysis, and the like). In certain processes, the expression of marker genes characteristic of hES-derived cells as well as the lack of significant expression of marker genes characteristic of hES-derived cells. Still further methods for characterizing and identifying hES-derived cells types are described in related applications as indicated above, which are herein incorporated by reference in their entirety.

Amplification probe/primer combinations suitable for use in amplification assays include the following: Insulin (INS) (GenBank NM_000207): primers AAGAGGCCATCAAG-CAGATCA (SEQ ID NO: 1); CAGGAGGCGCATCCACA (SEQ ID NO: 2); Nkx6.1 (NM_006168): primers CTGGC-CTGTACCCCTCATCA (SEQ ID NO: 3); CTTC-CCGTCTTTGTCCAACAA (SEQ ID NO: 4); Pdx1 (NM_000209): primers AAGTCTACCAAAGCTCACGCG (SEQ ID NO: 5); GTAGGCGCCGCCTGC (SEQ ID NO: 6); Ngn3 (NM_020999): primers GCTCATCGCTCTCTAT-TCTTTTGC (SEQ ID NO: 7); GGTTGAGGCGTCATC-CTTTCT (SEQ ID NO: 8); FOXA2 (HNF3B) (NM_021784): primers GGGAGCGGTGAAGATGGA (SEQ ID NO: 9); TCATGTTGCTCACGGAGGAGTA (SEQ ID NO: 10); Glucagon (GCG) (NM_002054): primers AAGCATT-TACTTTGTGGCTGGATT (SEQ ID NO: 11); TGATCTG-GATTTCTCCTCTGTGTCT (SEQ ID NO: 12); HNF6 (NM_030712): primers CGCTCCGCTTAGCAGCAT (SEQ ID NO: 13); GTGTTGCCTCTATCCTTCCCAT (SEQ ID NO: 14); HNF4Alpha (NM_000457): primers GAAGAAG-GAAGCCGTCCAGA (SEQ ID NO: 15); GACCTTCGAGT-GCTGATCCG (SEQ ID NO: 16); Sox17 (NM_022454): primers GGCGCAGCAGAATCCAGA (SEQ ID NO: 17); NNNNNNNNNNNNNNN NNNNN (SEQ ID NO: 18); HLxB9 (NM_005515): primers CACCGCGGGCATGATC (SEQ ID NO: 19); ACTTCCCCAGGAGGTTCGA (SEQ ID NO: 20); Nkx2.2 (NM_002509): primers GGCCTTCAG-TACTCCCTGCA (SEQ ID NO: 21); GGGACTTGGAGCT-TGAGTCCT (SEQ ID NO: 22); PTF1a (NM_178161): primers GAAGGTCATCATCTGCCATCG (SEQ ID NO: 23) GGCCATAATCAGGGTCGCT (SEQ ID NO: 24); SST (NM_001048): primers CCCCAGACTCCGTCAGTTTC (SEQ ID NO: 25); TCCGTCTGGTTGGGTTCAG (SEQ ID NO: 26); PAX6 (NM_000280): primers CCAGAAAGGAT-GCCTCATAAAGG (SEQ ID NO: 27); TCTGCGCGC-CCCTAGTTA (SEQ ID NO: 28); Oct4 primers: TGGGCTC-GAGAAGGATGTG (SEQ ID NO: 29) GCATAGTCGCTGCTTGATCG (SEQ ID NO: 30); MIXL1 primers CCGAGTCCAGGATCCAGGTA (SEQ ID NO: 31)

CTCTGACGCCGAGACTTGG (SEQ ID NO: 32); GATA4 primers CCTCTTGCAATGCGGAAAG (SEQ ID NO: 33) CGGGAGGAAGGCTCTCACT (SEQ ID NO: 34); GSC primers GAGGAGAAAGTGGAGGTCTGGTT (SEQ ID NO: 35) CTCTGATGAGGACCGCTTCTG (SEQ ID NO: 36); CER primers ACAGTGCCCTTCAGCCAGACT (SEQ ID NO: 37) ACAACTACTTTTTCACAGCCTTCGT (SEQ ID NO: 38); AFP primers GAGAAACCCACTGGAGAT-GAACA (SEQ ID NO: 39) CTCATGGCAAAGTTCTTC-CAGAA (SEQ ID NO: 40); SOX1 primers ATGCACCGC-TACGACATGG (SEQ ID NO: 41) CTCATGTAGCCCTGCGAGTTG (SEQ ID NO: 42); ZIC1 primers CTGGCTGTGGCAAGGTCTTC (SEQ ID NO: 43) CAGCCCTCAAACTCGCACTT (SEQ ID NO: 44); NFM primers ATCGAGGAGCGCCACAAC (SEQ ID NO: 45) TGCTGGATGGTGTCCTGGT (SEQ ID NO: 46). Other primers are available through ABI Taqman including FGF17 (Hs00182599_1), VWF (Hs00169795_1), CMKOR1 (Hs00604567_1), CRIP1 (Hs00832816_1), FOXQ1 (Hs00536425_1), CALCR (Hs00156229_1) and CHGA (Hs00154441_1).

Summary of the Production of PDX1-Positive Pancreatic Endoderm (Stages 1 to 4) and Insulin Production In Vivo The methods for production of certain endoderm-lineage and pancreatic endoderm-lineage cells are provided herein, and discussed elsewhere in related applications such as U.S. application Ser. No. 11/773,944, entitled METHODS OF PRODUCING PANCREATIC HORMONES, filed Jul. 5, 2007, which is a continuation-in-part of U.S. patent application Ser. No. 11/681,687, entitled ENDOCRINE PRECURSOR CELLS, PANCREATIC HORMONE-EXPRESSING CELLS AND METHODS OF PRODUCTION, filed Mar. 2, 2007; which are incorporated herein by reference in their entirety.

Briefly, the directed differentiation methods herein for pluripotent stem cells, for example, hES and iPS cells, can be described into at least four or five stages. Stage 1 is the production of definitive endoderm from pluripotent stem cells and takes about 2 to 5 days, preferably 2 or 3 days. Pluripotent stem cells are suspended in media comprising RPMI, a TGFβ superfamily member growth factor, such as Activin A, Activin B, GDF-8 or GDF-11 (100 ng/ml), a Wnt family member or Wnt pathway activator, such as Wnt3a (25 ng/ml), and alternatively a rho-kinase or ROCK inhibitor, such as Y-27632 (10 µM) to enhance growth, survival and proliferation as well as promoting cell-cell adhesion. After about 24 hours, the media is exchanged for media comprising RPMI with serum, such as 0.2% FBS, and a TGFβ superfamily member growth factor, such as Activin A, Activin B, GDF-8 or GDF-11 (100 ng/ml), and alternatively a rho-kinase or ROCK inhibitor for another 24 (day 1) to 48 hours (day 2). Alternatively, after about 24 hours in a medium comprising Activin/Wnt3a, the cells are cultured during the subsequent 24 hours in a medium comprising Activin alone (i.e., the medium does not include Wnt3a). Importantly, production of definitive endoderm requires cell culture conditions low in serum content and thereby low in insulin or insulin-like growth factor content. See McLean et al. (2007) Stem Cells 25: 29-38, which is herein incorporated in its entirety. McLean et al. also show that contacting hES cells with insulin in concentrations as little as 0.2 µg/ml at Stage 1 can be detrimental to the production of definitive endoderm. Still others skilled in the art have modified the Stage 1 differentiation of pluripotent cells to definitive endoderm substantially as described here and in D'Amour et al. (2005), for example, at least, Agarwal et al., Efficient Differentiation of Functional Hepatocytes from Human Embryonic Stem Cells, Stem Cells (2008) 26:1117-1127; Borowiak et al., Small Molecules Efficiently Direct Endodermal Differentiation of Mouse and Human Embryonic Stem Cells, (2009) Cell Stem Cell 4:348-358; and Brunner et al., Distinct DNA methylation patterns characterize differentiated human embryonic stem cells and developing human fetal liver, (2009) Genome Res. 19:1044-1056. Proper differentiation, specification, characterization and identification of definitive are necessary in order to derive other endoderm-lineage cells. Definitive endoderm cells at this stage co-express SOX17 and HNF3β (FOXA2) and do not appreciably express at least HNF4alpha, HNF6, PDX1, SOX6, PROX1, PTF1A, CPA, cMYC, NKX6.1, NGN3, PAX3, ARX, NKX2.2, INS, GSC, GHRL, SST, or PP.

Stage 2 takes the definitive endoderm cell culture from Stage 1 and produces foregut endoderm or PDX1-negative foregut endoderm by incubating the suspension cultures with RPMI with low serum levels, such as 0.2% FBS, in a 1:1000 dilution of ITS, 25 ng KGF (or FGF7), and alternatively a ROCK inhibitor for 24 hours (day 2 to day 3) to enhance growth, survival, proliferation and promote cell-cell adhesion. After 24 hours (day 3 to day 4), the media is exchanged for the same media minus a TGFβ inhibitor, but alternatively still a ROCK inhibitor to enhance growth, survival and proliferation of the cells, for another 24 (day 4 to day 5) to 48 hours (day 6). A critical step for proper specification of foregut endoderm is removal of TGFβ family growth factors. Hence, a TGFβ inhibitor can be added to Stage 2 cell cultures, such as 2.5 µM TGFβ inhibitor no. 4 or 5 µM SB431542, a specific inhibitor of activin receptor-like kinase (ALK), which is a TGFβ type I receptor. Foregut endoderm or PDX1-negative foregut endoderm cells produced from Stage 2 co-express SOX17, HNF1β and HNF4alpha and do not appreciably co-express at least SOX17 and HNF3β (FOXA2), nor HNF6, PDX1, SOX6, PROX1, PTF1A, CPA, cMYC, NKX6.1, NGN3, PAX3, ARX, NKX2.2, INS, GSC, GHRL, SST, or PP, which are hallmark of definitive endoderm, PDX1-positive pancreatic endoderm or pancreatic progenitor cells or endocrine precursors as well as singly or poly hormonal type cells.

Stage 3 (days 5-8) takes the foregut endoderm cell culture from Stage 2 and produces a PDX1-positive foregut endoderm cell by DMEM or RPMI in 1% B27, 0.25 µM KAAD cyclopamine, a retinoid, such as 0.2 µM retinoic acid (RA) or a retinoic acid analog such as 3 nM of TTNPB, and 50 ng/mL of Noggin for about 24 (day 7) to 48 hours (day 8). Specifically, Applicants have used DMEM-high glucose since about 2003 and all patent and non-patent disclosures as of that time employed DMEM-high glucose, even if not mentioned as "DMEM-high glucose" and the like. This is, in part, because manufacturers such as Gibco did not name their DMEM as such, e.g. DMEM (Cat. No 11960) and Knockout DMEM (Cat. No 10829). It is noteworthy, that as of the filing date of this application, Gibco offers more DMEM products but still does not put "high glucose" in certain of their DMEM products that contain high glucose e.g. Knockout DMEM (Cat. No. 10829-018). Thus, it can be assumed that in each instance DMEM is described, it is meant DMEM with high glucose and this was apparent by others doing research and development in this field. Again, a ROCK inhibitor or rho-kinase inhibitor such as Y-27632 can be used to enhance growth, survival, proliferation and promote cell-cell adhesion. PDX1-positive foregut cells produced from Stage 3 co-express PDX1 and HNF6 as well as SOX9 and PROX, and do not appreciably co-express markers indicative of definitive endoderm or foregut endoderm (PDX1-negative foregut endoderm) cells or PDX1-positive foregut endoderm cells as described above in Stages 1 and 2.

Stage 4 (days 8-14) takes the media from Stage 3 and exchanges it for media containing DMEM in 1% vol/vol B27 supplement, plus 50 ng/mL KGF and 50 ng/mL of EGF and sometimes also 50 ng/mL Noggin. Again, a ROCK inhibitor such as Y-27632 can be used to enhance growth, survival, proliferation and promote cell-cell adhesion. PDX1-positive pancreatic endoderm cells produced from Stage 4 co-express at least PDX1 and NRx6.1 as well as PTF1A, and do not appreciably express markers indicative of definitive endoderm or foregut endoderm (PDX1-negative foregut endoderm) cells as described above in Stages 1, 2 and 3.

Alternatively, the cells from Stage 4 can be further differentiated in Stage 5 to produce endocrine precursor or progenitor type cells and/or singly and poly-hormonal pancreatic endocrine type cells from Stage 4 cells in a medium containing DMEM in 1% vol/vol B27 supplement for about 1 to 6 days (days 15-20). Endocrine precursors produced from Stage 5 co-express at least NGN3 and PAX4 as well as NRx2.2, and do not appreciably express markers indicative of definitive endoderm or foregut endoderm (PDX1-negative foregut endoderm) or PDX1-positive pancreatic endoderm or progenitor cells as described above in Stages 1, 2, 3 and 4.

PDX1-positive pancreatic endoderm produced from Stage 4 are loaded and wholly contained in a macro-encapsulation device and transplanted in a patient, and the PDX1-positive pancreatic endoderm cells mature into pancreatic hormone secreting cells, e.g., insulin secreting cells, in vivo. Encapsulation of the PDX1-positive pancreatic endoderm cells and production of insulin in vivo is described in detail in U.S. patent application Ser. No. 12/618,659 (the '659 application"), entitled ENCAPSULATION OF PANCREATIC LINEAGE CELLS DERIVED FROM HUMAN PLURIPOTENT STEM CELLS, filed Nov. 13, 2009. The '659 application claims the benefit of priority to U.S. Provisional Patent Application No. 61/114,857, entitled ENCAPSULATION OF PANCREATIC PROGENITORS DERIVED FROM HES CELLS, filed Nov. 14, 2008; and U.S. Provisional Patent Application No. 61/121,084, entitled ENCAPSULATION OF PANCREATIC ENDODERM CELLS, filed Dec. 9, 2008. The disclosures of each of these applications are incorporated herein by reference in their entirety.

The methods, compositions and devices described herein are presently representative of preferred embodiments and are exemplary and are not intended as limitations on the scope of the invention. Changes therein and other uses will occur to those skilled in the art which are encompassed within the spirit of the invention and are defined by the scope of the disclosure. Accordingly, it will be apparent to one skilled in the art that varying substitutions and modifications may be made to the invention disclosed herein without departing from the scope and spirit of the invention.

For example, Activin A, a member of the TGFβ superfamily of growth factors or signaling proteins, is used to produce definitive endoderm from pluripotent cells, e.g., hES cells and iPS cells, however, other TGFβ super family members can be used, for example GDF-8 and GDF-11, to produce definitive endoderm such as those described in International Patent Application No. PCT/US2008/065686, entitled GROWTH FACTORS FOR PRODUCTION OF DEFINITIVE ENDODERM, filed Jun. 3, 2008, which is herein incorporated by reference in its entirety.

Retinoic acid (RA) is used to differentiate PDX1-negative foregut endoderm cells in Stage 2 to PDX1-positive foregut cells in Stage 3. However, other retinoids or retinoic acid analogues such as 4-[(E)-2-(5,6,7,8-tetrahydro-5,5,8,8-tetramethyl-2-napthalenyl)-1-propenyl]benzoic acid (or TTNPB) and similar analogs (e.g., 4-HBTTNPB) can be used.

Noggin is a protein for example that inactivates members of the TGFβ superfamily signaling proteins, such as bone morphogenetic protein-4 (BMP4). However, other BMP4 inhibitors such as Chordin and Twisted Gastrulation (Tsg) or anti-BMP neutralizing antibodies can prevent BMP binding to its cell surface receptors, thereby effectively inhibiting the BMP signaling. Alternatively, the gene for human Noggin has been cloned and sequenced. See U.S. Pat. No. 6,075,007, which is herein incorporated by reference. Analysis of the Noggin sequence shows a carboxy terminal region having homology to a Kunitz-type protease inhibitor, indicating that potentially other Kunitz-type protease inhibitors may have a similar effect on inhibiting BMP.

Lastly, the macro-encapsulation devices described herein and in U.S. patent application Ser. No. 12/618,659 and incorporated herein by reference in its entirety, are again only exemplary and are not intended as limitations on the scope of the invention. Particularly, changes to the device design such as size of the device, plurality of chambers or subcompartments in the device, or plurality of ports, or even mechanisms for loading and extracting the device are all encompassed within the spirit of the invention. Hence, it will be apparent to one skilled in the art that varying substitutions and modifications not only to the described differentiation methods herein but to the encapsulation device as well may be made to the invention disclosed herein without departing from the scope and spirit of the invention.

Production and Compositions of Definitive Endoderm (Stage 1)

In some processes, differentiation to definitive endoderm is achieved by providing to the pluripotent cell culture a growth factor of the TGFβ superfamily in an amount sufficient to promote differentiation to definitive endoderm. Growth factors of the TGFβ superfamily which are useful for the production of definitive endoderm are selected from the Nodal/Activin, GDF-8, -9, -10, -11 and the like or BMP subgroups. In some preferred differentiation processes, the growth factor is selected from the group consisting of Nodal, Activin A, Activin B, GDF-8, GDF-11 and BMP4. Additionally, the growth factor Wnt3a, other Wnt family members, and Wnt pathway activators are useful for the production of definitive endoderm cells. In certain differentiation processes, combinations of any of the above-mentioned growth factors can be used. This and other methods are described in detail in U.S. Pat. No. 7,510,876, which is herein incorporated by reference in its entirety.

With respect to some of the processes for the differentiation of pluripotent cells to definitive endoderm cells, the above-mentioned growth factors are provided to the cells so that the growth factors are present in the cultures at concentrations sufficient to promote differentiation of at least a portion of the pluripotent cells to definitive endoderm cells. In some processes, the above-mentioned growth factors are present in the cell culture at a concentration of at least about 5 ng/ml, at least about 10 ng/ml, at least about 25 ng/ml, at least about 50 ng/ml, at least about 75 ng/ml, at least about 100 ng/ml, at least about 200 ng/ml, at least about 300 ng/ml, at least about 400 ng/ml, at least about 500 ng/ml, at least about 1000 ng/ml, at least about 2000 ng/ml, at least about 3000 ng/ml, at least about 4000 ng/ml, at least about 5000 ng/ml or more than about 5000 ng/ml.

In certain processes for the differentiation of pluripotent cells to definitive endoderm cells, the above-mentioned growth factors are removed from the cell culture subsequent to their addition. For example, the growth factors can be removed within about one day, about two days, about three days, about four days, about five days, about six days, about seven days, about eight days, about nine days or about ten days after their addition. In a preferred process, the growth factors are removed about four days after their addition.

In some embodiments of the processes described herein, definitive endoderm cells are enriched, isolated and/or purified prior to further differentiation. In such embodiments, definitive endoderm cells can be enriched, isolated and/or purified using any known method. In preferred embodiments, the definitive endoderm cells are enriched, isolated and/or purified using one or more of the methods described in U.S. patent application Ser. No. 11/021,618, entitled DEFINITIVE ENDODERM, filed Dec. 23, 2004, and U.S. Provisional Patent Application No. 60/736,598, entitled MARKERS OF DEFINITIVE ENDODERM, filed Nov. 14, 2005, the disclosures of which are incorporated herein by reference in their entireties.

In a preferred embodiment, the definitive endoderm cells produced and described herein have relatively high levels of CER, GSC, CXCR4, SOX17 and FOXA2 gene expression when normalized and compared to levels of control genes, such as housekeeping genes.

Production and Compositions of PDX1-Negative Foregut Endoderm (Stage 2)

Definitive endoderm cells can be specified toward pancreatic differentiation by further differentiation of these cells to produce PDX1-negative foregut endoderm cells. In some of the differentiation processes described herein, cell cultures as well as enriched or purified cell populations comprising definitive endoderm cells can be used for further differentiation to cell cultures and/or enriched cell populations comprising PDX1-negative foregut endoderm cells.

Typically, definitive endoderm cells are differentiated to PDX1-negative foregut endoderm cells by reducing or eliminating or removing TGFβ superfamily growth factor signaling in a cell culture or cell population of SOX17-positive definitive endoderm cells. In some embodiments, reducing or eliminating TGFβ superfamily growth factor signaling is mediated by diluting or removing an exogenously added TGFβ superfamily growth factor, such as activin A, from the cell culture or cell population of definitive endoderm. In other embodiments, TGFβ superfamily growth factor signaling is reduced or eliminated by providing the definitive endoderm cells with a compound that blocks TGFβ superfamily growth factor signaling, such as follistatin and/or noggin. In some embodiments, TGFβ superfamily growth factor signaling can be reduced or eliminated for about one day, about two days, about three days, about four days, about five days, about six days, about seven days, about eight days, about nine days, about ten days or greater than about ten days subsequent to the differentiation of the human pluripotent cells to definitive endoderm cells.

In some embodiments, differentiation of definitive endoderm cells to foregut endoderm cells is enhanced by providing the definitive endoderm cell culture or cell population with an FGF-family growth factor and/or a hedgehog pathway inhibitor. In such embodiments the FGF-family growth factor and/or hedgehog pathway inhibitor is provided at about one day, about two days, about three days, about four days, about five days, about six days, about seven days, about eight days, about nine days, about ten days or greater than about ten days subsequent to reducing or eliminating TGFβ superfamily growth factor signaling in the definitive endoderm cell culture. In a preferred embodiment, the FGF-family growth factor and/or hedgehog pathway inhibitor is provided at about the same time as reducing or eliminating TGFβ superfamily growth factor signaling in the definitive endoderm cell culture.

In a preferred embodiment, the FGF-family growth factor provided to the definitive endoderm cell culture or cell population is FGF10 and/or FGF7. However, it will be appreciated that other FGF-family growth factors or FGF-family growth factor analogs or mimetics may be provided instead of or in addition to FGF10 and/or FGF7. For example, an FGF-family growth factor selected from the group consisting of FGF1, FGF2, FGF3, and the like up to and including FGF23 may be provided. In such embodiments, the FGF-family growth factor and/or the FGF-family growth factor analog or mimetic is provided to the cells of a cell culture such that it is present at a concentration of at least about 10 ng/ml, at least about 25 ng/ml, at least about 50 ng/ml, at least about 75 ng/ml, at least about 100 ng/ml, at least about 200 ng/ml, at least about 300 ng/ml, at least about 400 ng/ml, at least about 500 ng/ml, or at least about 1000 ng/ml.

In other preferred embodiments, the hedgehog inhibitor is KAAD-cyclopamine. However, it will be appreciated that other hedgehog inhibitors can be used. Such inhibitors include, but are not limited to, KAAD-cyclopamine analogs, jervine, jervine analogs, hedgehog pathway blocking antibodies and any other inhibitors of hedgehog pathway function known to those of ordinary skill in the art. When used alone or in conjunction with FGF-family growth factor, the hedgehog inhibitor can be provided at a concentration of at least about 0.01 µM to 50 µM.

In a preferred process for the production of a population of PDX1-negative foregut endoderm cells from definitive endoderm cells, TGFβ superfamily growth factor signaling is reduced or eliminated for about two day subsequent to the differentiation of a substantial portion of human pluripotent cells to definitive endoderm (for example, after a three day, four or five day differentiation protocol as described in the examples below). At about the same time, the cell culture or cell population of definitive endoderm cells is provided noggin and KAAD-cyclopamine, e.g., 50 ng/ml of Noggin and 0.25 µM KAAD-cyclopamine in DMEM medium in the presence of 2 mM RA or 3 nM TTNPB.

In some embodiments, the PDX1-negative foregut endoderm cells can be further differentiated to PDX1-positive foregut endoderm cells by contacting the cells with a medium comprising, or otherwise providing to the cells, a retinoid, such as retinoic acid (RA). In some embodiments, the retinoid is provided to the cells of a cell culture such that it is present at a concentration of at least about 1 nM to 50 µM. In such embodiments, the retinoid is provided to the cells at about one day, about two days, about three days, about four days, about five days, about six days, about seven days, about eight days, about nine days, about ten days or greater than about ten days subsequent to reducing or eliminating TGFβ superfamily growth factor signaling in the definitive endoderm cell culture. In a preferred embodiment, from about 0.05 µM RA to about 2 µM RA is provided to the PDX-1 negative foregut endoderm cell culture about 2 to 3 days subsequent to reducing or eliminating TGFβ superfamily growth factor signaling.

In some of the differentiation processes described herein, the above-mentioned differentiation factors are removed from the cell culture subsequent to their addition. For example, the above-mentioned differentiation factors can be removed within about one day, about two days, about three days, about four days, about five days, about six days, about seven days, about eight days, about nine days or about ten days after their addition.

In a preferred embodiment, the PDX1-negative foregut endoderm cells produced and described herein have relatively high levels of SOX17, FOXA1, HNF1B and HNF4A gene expression when normalized to levels of control genes, such as housekeeping genes. In particular, levels of HNF4A gene expression does not substantially increase until removal of TGFβ superfamily growth factor signaling (e.g., Activin) from a, definitive endoderm culture, for example.

Production and Compositions of PDX1-Positive Foregut Endoderm (Stage 3)

PDX1-negative foregut endoderm cells can be further specified toward pancreatic differentiation by further differentiation of these cells to produce PDX1-positive foregut endoderm cells or PDX1-positive pancreatic endoderm or equivalents thereof. In some of the differentiation processes described herein, cell cultures as well as enriched or purified cell populations comprising definitive endoderm cells can be used for further differentiation to cell cultures and/or enriched cell populations comprising PDX1-positive foregut endoderm cells.

Typically, PDX1-negative foregut endoderm cells are differentiated to PDX1-positive foregut endoderm cells by providing to a cell culture comprising SOX17-positive foregut endoderm cells a retinoid, such as retinoic acid (RA). In some of the differentiation processes, PDX1-negative foregut endoderm cells in culture are also provided with a member of the fibroblast growth factor family either prior to or about the same time as the addition of RA. A preferred fibroblast growth factor is FGF-7. In another preferred process, the fibroblast growth factor comprises any fibroblast growth factor or a ligand that stimulates or otherwise interacts with the fibroblast growth factor 2 receptor Mb (FGFR2(IIIb)). In even more preferred processes, the FGF family growth factor is used in conjunction with a hedgehog pathway inhibitor. A preferred hedgehog pathway inhibitor is KAAD-cyclopamine. In especially preferred differentiation processes, FGF-10 and/or KAAD-cyclopamine are provided to a cell culture comprising PDX1-negative definitive endoderm cells in the presence of RA. In certain processes, BMP4 may be included with FGF 10 and/or KAAD-cyclopamine in the presence of RA. In some processes, the retinoid is used in conjunction with a member of the TGFβ superfamily of growth factors and/or Connaught Medical Research Labs medium (CRML medium) (Invitrogen, Carlsbad, Calif.).

With respect to some of the embodiments of differentiation processes described herein, the retinoid and/or a combination of the above-mentioned differentiation factors are provided to the cells so that these factors are present in the cell culture or cell population at concentrations sufficient to promote differentiation of at least a portion of the PDX1-negative foregut endoderm cell culture or cell population to PDX1-positive foregut endoderm cells.

In other processes, FGF-10 is provided to the cells of a cell culture such that it is present at a concentration of at least about 1 ng/ml, at least about 2 ng/ml, at least about 5 ng/ml, at least about 10 ng/ml, at least about 25 ng/ml and up to 50 µM. In some embodiments of the present invention, a fibroblast growth factor or a ligand that stimulates or otherwise interacts with the fibroblast growth factor 2 receptor Mb (FGFR2(IIIb)) is provided either alone or in combination with the hedgehog pathway inhibitor.

In a preferred process for the production of a population of PDX1-positive foregut endoderm cells from PDX1-negative foregut endoderm cells, a cell culture or an enriched cell population of PDX1-negative foregut endoderm cells is provided with FGF-7, KAAD-cyclopamine and retinoic acid (RA), e.g., 25 ng/ml of FGF-7 and 0.2 µM KAAD-cyclopamine in CMRL medium in the presence of 2 µM RA.

In some processes described herein, TGFβ signaling factor, e.g., activin A and/or activin B, GDF-8, GDF-11 and the like are provided to the cell culture along with the retinoid and/or the fibroblast growth factor and the hedgehog inhibitor. For example, in such processes, activin A and/or activin B and/or GDF-8 and/or GDF-11 is provided to the cell culture at a concentration of at least about 5 ng/ml, at least about 10 ng/ml, at least about 25 ng/ml, at least about 50 ng/ml, at least about 75 ng/ml, at least about 100 ng/ml, at least about 200 ng/ml, at least about 300 ng/ml, at least about 400 ng/ml, at least about 500 ng/ml, or at least about 1000 ng/ml.

In some processes, the differentiation factors and/or CRML medium is provided to the PDX1-negative foregut endoderm cells at about one day, two days, three days, at about four days, at about five days, at about six days, at about seven days, at about eight days, at about nine days, at about ten days or at about greater than ten days subsequent to the initiation of differentiation from pluripotent cells. In preferred processes, differentiation factors and/or CRML medium is provided to the PDX1-negative foregut endoderm cells at about three or four or five days subsequent to the initiation of differentiation from pluripotent stem cells.

In certain processes described herein, the above-mentioned differentiation factors are removed from the cell culture subsequent to their addition. For example, the above-mentioned differentiation factors can be removed within about one day, about two days, about three days, about four days, about five days, about six days, about seven days, about eight days, about nine days or about ten days after their addition.

These and other methods are described in detail in U.S. Provisional Patent Application No. 60/730,917, entitled PDX1-EXPRESSING DORSAL AND VENTRAL FOREGUT ENDODERM, filed Oct. 27, 2005, and PDX1-positive foregut endoderm cells can be found in U.S. patent application Ser. No. 11/115,868, entitled PDX1 EXPRESSING ENDODERM, filed Apr. 26, 2005, the disclosures of which are incorporated herein by reference in their entirety.

In a preferred embodiment, the PDX1-positive foregut endoderm cells produced and described herein have relatively high levels of PDX1, NKX6.1, PTF1A, CPA and cMYC gene expression when normalized and compared to levels of control genes, such as housekeeping genes.

Production and Compositions of PDX1-Positive Pancreatic Endoderm (Stage 4)

Production and compositions of PDX1-positive pancreatic endoderm or "pancreatic epithelium" or more generally pancreatic progenitors is described in detail in U.S. patent application Ser. No. 12/167,227, entitled METHODS OF PRODUCING PANCREATIC HORMONES, filed Jul. 2, 2008, which issued May 19, 2009 as U.S. Pat. No. 7,534,608. The Ser. No. 12/167,227 application is a continuation of U.S. patent application Ser. No. 11/773,944, entitled METHODS OF PRODUCING PANCREATIC HORMONES, filed Jul. 5, 2007, which is a continuation-in-part of U.S. patent application Ser. No. 11/681,687, entitled ENDOCRINE PRECURSOR CELLS, PANCREATIC HORMONE-EXPRESSING CELLS AND METHODS OF PRODUCTION, filed Mar. 2, 2007. The disclosures of each of these applications are incorporated herein by reference in their entirety.

Example 22 of the Ser. No. 12/167,227 application describes in detail various modifications of the cell culture conditions described herein in Stages 1 to 4. In general, Stage 3 PDX1-positive foregut endoderm type cells are cultured in media containing DMEM in 1% vol/vol B27 supplement plus Noggin, or another BMP4 specific inhibitor for about 1 to 3 days, or about 1 to 4 days, or 1 to 5 days, or about 1 to 6 days. At the end of Stage 4, a PDX1-positive pancreatic endoderm is produced, which cell at least co-expresses PDX1 and NRx6.1 as well as PTF1A. The cell culture does not appreciably express cells indicative of singly or poly-hormonal endocrine cells of Stage 5, or definitive endoderm cells of Stage 1, or PDX1-negative foregut endoderm cells of Stage 2, or PDX1-positive foregut endoderm cells of Stage 3.

Production and Compositions of Endocrine Precursor Cells (Stage 5)

Some embodiments described herein relate to methods of producing endocrine precursor cells starting from pluripotent cells. As described above, endocrine precursor cells can be produced by first differentiating pluripotent cells to produce definitive endoderm cells then further differentiating the definitive endoderm cells to produce PDX1-positive foregut endoderm cells. In such embodiments, PDX1-positive foregut endoderm cells are further differentiated to multipotent endocrine precursor cells, which are capable of differentiating into human pancreatic islet hormone-expressing cells.

In one embodiment, PDX1-positive foregut endoderm cells are differentiated to endocrine precursor cells by continuing the incubation of PDX1-positive foregut endoderm cells in the presence of a retinoid, such as retinoic acid, for an amount of time sufficient to produce endocrine precursor cells. In some embodiments, the amount of time sufficient for the production of endocrine precursor cells ranges from about 1 hour to about 10 days subsequent to the expression of the PDX1 marker in a portion of the cells in the cell culture. In some embodiments, the retinoid is maintained in the cell culture for about 1 hour, about 2 hours, about 4 hours, about 6 hours, about 8 hours, about 10 hours, about 12 hours, about 16 hours, about 1 day, about 2 days, about 3 days, about 4 days, about 5 days, about 6 days, about 7 days, about 8 days, about 9 days, about 10 days or greater than about 10 days subsequent to the expression of the PDX1 marker in a portion of the cells in the cell culture.

In some processes described herein, the concentration of retinoid used to differentiate PDX1-positive foregut endoderm cells in the cell culture or cell population to endocrine precursor cells ranges from about 1 nM to about 100 µM.

In some preferred embodiments, differentiation from PDX1-positive foregut endoderm cells to pancreatic endocrine precursor cells is mediated by providing a cell culture or cell population comprising human PDX1-positive foregut endoderm cells with a gamma secretase inhibitor. In a preferred embodiment, the gamma secretase inhibitor is N—[N-(3,5-Difluorophenacetyl-L-alanyl)]-S-phenylglycine t-Butyl Ester (DAPT).

In other embodiments, the gamma secretase inhibitor is provided at the start of the differentiation process, for example, at the pluripotent stage, and remains in the cell culture throughout the differentiation to pancreatic islet hormone-expressing cells. In still other embodiments, the gamma secretase inhibitor is added subsequent to the initiation of differentiation but prior to differentiation to the PDX1-positive foregut endoderm stage. In preferred embodiments, the gamma secretase inhibitor is provided to the cell culture or cell population at about the same time as providing the differentiation factors which promote the conversion of definitive endoderm to PDX1-positive endoderm. In other preferred embodiments, the gamma secretase inhibitor is provided to the cell culture or cell population after a substantial portion of the cells in the cell culture or cell population have differentiated to PDX1-positive foregut endoderm cells.

With respect to some embodiments regarding the differentiation of PDX1-positive foregut endoderm cells to endocrine precursor cells, the gamma secretase inhibitor is provided to the cells so that it is present in the cell culture or cell population at concentrations sufficient to promote differentiation of at least a portion of the PDX1-positive cells to endocrine precursor cells. In some embodiments, the gamma secretase inhibitor is present in the cell culture or cell population at a concentration ranging from about 0.01 µM to about 1000 µM. In preferred embodiments, the gamma secretase inhibitor is present in the cell culture or cell population at a concentration ranging from about 0.1 µM to about 100 µM.

In certain embodiments of the processes for producing endocrine precursor cells as described herein, the gamma secretase inhibitor is provided after one or more previously provided differentiation factors have been removed from the cell cultures. For example, the one or more previously provided differentiation factors can be removed about 1 day to 10 days or more than about 10 days prior to the addition of the gamma secretase inhibitor. In other embodiments, the gamma secretase inhibitor is provided to cell cultures or cell populations comprising one or more differentiation factors that were previously provided or provided at about the same time as the gamma secretase inhibitor. In preferred embodiments, differentiation factors that were previously provided or provided at about the same time as the gamma secretase inhibitor include, but are not limited to, FGF-10, KAAD-cyclopamine, activin A, activin B, GDF-8, GDF-11, BMP4 and/or RA.

In some embodiments of the invention described herein, exendin 4 is provided to the differentiating cell culture or cell population at about the same time as the gamma secretase inhibitor. In certain embodiments, exendin 4 is provided so as to be in present in the cell culture or cell population at a concentration of at least about 0.1 ng/ml, to 1000 ng/ml.

In a preferred process for the production of endocrine precursor cells from PDX1-positive foregut endoderm cells, a cell culture or cell population of PDX1-positive foregut endoderm cells is provided with 3 µM DAPT and 40 ng/ml exendin 4. In especially preferred embodiments, the cells are differentiated in CMRL. In another especially preferred process, for the production of a endocrine precursor cells from PDX1-positive foregut endoderm cells, a cell culture or cell population of PDX1-positive foregut endoderm cells is provided with 3 µM DAPT and 40 ng/ml exendin 4 in the presence of 2 µM RA.

It will be appreciated that NGN3, NKX2.2 and/or PAX4 marker expression is induced over a range of different levels in endocrine precursor cells depending on the differentiation conditions. As such, in some embodiments described herein, the expression of the NGN3, NKX2.2 and/or PAX4 marker in endocrine precursor cells or cell populations is at least about 2-fold higher to at least about 10.000-fold higher than the expression of the NGN3, NKX2.2 and/or PAX4 marker in non-endocrine precursor cells or cell populations, for example pluripotent stem cells, definitive endoderm cells, PDX1-positive foregut endoderm cells, immature pancreatic islet hormone-expressing cells, mature pancreatic islet hormone-expressing cells, extraembryonic endoderm cells, mesoderm cells and/or ectoderm cells. In other embodiments, the expression of the NGN3, NKX2.2 and/or PAX4 marker in endocrine precursor cells or cell populations is at least about 4-fold higher, at least about 6-fold higher to 10,000-fold higher than the expression of the NGN3, NKX2.2 and/or PAX4 marker in non-endocrine precursor cells or cell populations, for example pluripotent stem cells, definitive endoderm cells, PDX1-positive foregut endoderm cells, immature pancreatic islet hormone-expressing cells, mature pancreatic islet hormone-expressing cells, extraembryonic endoderm cells, mesoderm cells and/or ectoderm cells. In some embodiments, the expression of the NGN3, NKX2.2 and/or PAX4 marker in endocrine precursor cells or cell populations is infinitely higher than the expression of the NGN3, NKX2.2 and/or PAX4 marker in non-endocrine precursor cells or cell populations, for example pluripotent cells like iPS cells and hES cells, definitive endoderm cells, PDX1-positive foregut endoderm cells, immature pancreatic islet hormone-expressing cells, mature pancreatic islet hormone-expressing cells, extraembryonic endoderm cells, mesoderm cells and/or ectoderm cells.

Further embodiments of the present invention relate to compositions, such as cell cultures or cell populations, comprising human cells, including human endocrine precursor cells, wherein the expression of the NGN3 marker is greater than the expression of the AFP, SOX7, SOX1, ZIC1, NFM, MAFA, SYP, CHGA, INS, GCG, SST, GHRL, and/or PAX6 marker in at least about 2% of the human cells. In other embodiments, the expression of the NGN3 marker is greater than the expression of the AFP, SOX7, SOX1, ZIC1, NFM, MAFA, SYP, CHGA, INS, GCG, SST, GHRL, and/or PAX6 marker in at least about 5% to 98% of the human cells. In some embodiments, the percentage of human cells in the cell cultures or populations, wherein the expression of NGN3 is greater than the expression of the AFP, SOX7, SOX1, ZIC1, NFM, MAFA, SYP, CHGA, INS, GCG, SST, GHRL, and/or PAX6 marker, is calculated without regard to feeder cells.

It will be appreciated that some embodiments of the present invention relate to compositions, such as cell cultures or cell populations, comprising human endocrine precursor cells, wherein the expression of NKX2.2 and/or PAX4 is greater than the expression of the AFP, SOX7, SOX1, ZIC1, NFM, MAFA, SYP, CHGA, INS, GCG, SST, GHRL, and/or PAX6 marker in from at least about 2% to greater than at least about 98% of the human cells. In some embodiments, the expression of NKX2.2 and/or PAX4 is greater than the expression of the AFP, SOX7, SOX1, ZIC1, NFM, MAFA, SYP, CHGA, INS, GCG, SST, GHRL, and/or PAX6 marker in at least about 5% of the human cells to 98% of the human cells. In some embodiments, the percentage of human cells in the cell cultures or populations, wherein the expression of NKX2.2 and/or PAX4 is greater than the expression of the AFP, SOX7, SOX1, ZIC1, NFM, MAFA, SYP, CHGA, INS, GCG, SST, GHRL, and/or PAX6 marker, is calculated without regard to feeder cells.

Additional embodiments of the present invention relate to compositions, such as cell cultures or cell populations, comprising mammalian cells differentiated from definitive endoderm in vitro, such as human cells differentiated from definitive endoderm in vitro, wherein the expression of the NGN3, NKX2.2 and/or PAX4 marker is greater than the expression of the AFP, SOX7, SOX1, ZIC1, NFM, MAFA, SYP, CHGA, INS, GCG, SST, GHRL, and/or PAX6 marker in at least about 2% of the cells differentiated from definitive endoderm in vitro. In other embodiments, the expression of the NGN3, NKX2.2 and/or PAX4 marker is greater than the expression of the AFP, SOX7, SOX1, ZIC1, NFM, MAFA, SYP, CHGA, INS, GCG, SST, GHRL, and/or PAX6 marker in at least about 5% of the cells differentiated from definitive endoderm in vitro to 98% of the cells differentiated from definitive endoderm in vitro.

Using the processes described herein, compositions comprising endocrine precursor cells substantially free of other cell types can be produced. In some embodiments of the present invention, the endocrine precursor cell populations or cell cultures produced by the methods described herein are substantially free of cells that significantly express the AFP, SOX7, SOX1, ZIC1 and/or NFM markers. In some embodiments, the endocrine precursor cell populations of cell cultures produced by the methods described herein are substantially free of cells that significantly express the AFP, SOX7, SOX1, ZIC1, NFM, MAFA, SYP, CHGA, INS, GCG, SST, GHRL, and/or PAX6 markers.

In one embodiment of the present invention, a description of a endocrine precursor cell based on the expression of markers is, NGN3 high, NKX2.2 high, PAX4 high, AFP low, SOX7 low, SOX1 low, ZIC1 low NFM low, MAFA low; SYP low; CHGA low; INS low, GCG low, SST low, GHRL low and/or PAX6 low.

Production of Immature Pancreatic Islet Hormone-Expressing Cells

Embodiments described herein relate to methods of producing immature pancreatic islet hormone-expressing cells starting from pluripotent cells. As described above, immature pancreatic islet hormone-expressing cells can be produced by first differentiating pluripotent cells to produce definitive endoderm cells, differentiating the definitive endoderm cells to produce foregut endoderm cells, differentiating foregut endoderm to produce PDX1-positive foregut endoderm cells and then further differentiating the PDX1-positive foregut endoderm cells to produce endocrine precursor cells. In some embodiments, the process is continued by allowing the endocrine precursor cells to further differentiate to immature pancreatic islet hormone-expressing cells.

In some embodiments of the present invention, differentiation from endocrine precursor cells to immature pancreatic islet hormone-expressing cells proceeds by continuing the incubation of a culture of endocrine precursor cells with a gamma secretase inhibitor for a sufficient time that the cells stop substantially expressing NGN3, and start expressing PAX6, and to permit the cells to become competent to express at least one pancreatic islet cell hormone. In some embodiments, the gamma secretase inhibitor is removed about 1 day, about 2 days, about 3 days, about 4 days, about 5 days, about 6 days, about 7 days, about 8 days, about 9 days, about 10 days or more than about 10 days after the induction of endocrine precursor cells. In a preferred embodiment, the gamma secretase inhibitor is N—[N-(3,5-Difluorophenacetyl-L-alanyl)]-S-phenylglycine t-Butyl Ester (DAPT).

Certain processes for the production of immature pancreatic islet hormone-expressing cells disclosed herein are mediated by providing a cell culture or cell population comprising human endocrine precursor cells with one or more factors selected from the group consisting of nicotinamide, exendin 4, hepatocyte growth factor (HGF), insulin-like growth factor-1 (IGF1). In some embodiments, all four of the above-described factors are provided together. In some embodiments, one or more of the above-described factors are provided to the cell culture prior to the differentiation of endocrine precursor cells and remain present in the cell culture during the differentiation of at least a portion of the cells in the cell culture to endocrine precursor cells. In other embodiments, one or more of the above-described factors are provided to the cell culture at or about the time of differentiation of a substantial portion of the cells to endocrine precursor cells and remain present in the cell culture until at least a substantial portion of the cells have differentiated into immature pancreatic islet hormone-expressing cells. In some embodiments of the present invention, one or more of the above-described factors are provided at the start of the differentiation process, for example, at the pluripotent cell stage, and remain in the cell culture throughout the differentiation to immature pancreatic islet hormone-expressing cells.

In some processes for the production of immature pancreatic islet hormone-expressing cells disclosed herein, nicotinamide, nicotinamide-adenine dinucleotide (NAD), or nicotinic acid is provided to the cells so that it is present in the cell culture or cell population at concentrations sufficient to promote differentiation of at least a portion of the endocrine precursor cells to immature pancreatic islet hormone-expressing cells. In some embodiments, nicotinamide is present in the cell culture or cell population at a concentration of at least about 0.1 mM, at least about 0.5 mM, to 1000 mM.

In other processes for the production of immature pancreatic islet hormone-expressing cells disclosed herein, exendin 4 is provided to the cells so that it is present in the cell culture or cell population at concentrations sufficient to promote differentiation of at least a portion of the endocrine precursor cells to immature pancreatic islet hormone-expressing cells. In some embodiments, exendin 4 is present in the cell culture or cell population at a concentration of at least about 1 ng/ml at least about 5 ng/ml to 1000 ng/ml.

In still other processes for the production of immature pancreatic islet hormone-expressing cells disclosed herein, HGF is provided to the cells so that it is present in the cell culture or cell population at concentrations sufficient to promote differentiation of at least a portion of the endocrine precursor cells to immature pancreatic islet hormone-expressing cells. In some embodiments, HGF is present in the cell culture or cell population at a concentration of at least about 1 ng/ml at least about 5 ng/ml to 1000 ng/ml.

In yet other processes for the production of immature pancreatic islet hormone-expressing cells disclosed herein, IGF1 is provided to the cells so that it is present in the cell culture or cell population at concentrations sufficient to promote differentiation of at least a portion of the endocrine precursor cells to immature pancreatic islet hormone-expressing cells. In some embodiments, IGF1 is present in the cell culture or cell population at a concentration of at least about 1 ng/ml to 1000 ng/ml.

In certain embodiments of the processes for producing immature pancreatic islet hormone-expressing cells as described herein, one or more of nicotinamide, exendin 4, HGF and IGF1 are provided after one or more previously provided differentiation factors have been removed from the cell cultures. In other embodiments, one or more of nicotinamide, exendin 4, HGF and IGF1 are provided to cell culture or cell population comprising one or more differentiation factors that were previously provided or provided at about the same time as one or more of nicotinamide, exendin 4, HGF and IGF1. In preferred embodiments, differentiation factors that were previously provided or provided at about the same time as one or more of nicotinamide, exendin 4, HGF and IGF1 include, but are not limited to, DAPT, FGF-10, KAAD-cyclopamine, activin A, activin B, BMP4 and/or RA.

Further embodiments of the present invention relate to compositions, such as cell cultures or cell populations, comprising human cells, including human immature pancreatic islet hormone-expressing cells, wherein the expression of the MAFB, SYP, CHGA, NKX2.2, ISL1, PAX6, NEUROD, PDX1, HB9, GHRL, IAPP, INS GCG, SST, PP, and/or C-peptide marker is greater than the expression of the NGN3, MAFA, MOX1, CER, POU5F1, AFP, SOX7, SOX1, ZIC1 and/or NFM marker in at least about 2% of the human cells. In other embodiments, the expression of the MAFB, SYP, CHGA, NKX2.2, ISL1, PAX6, NEUROD, PDX1, HB9, GHRL, IAPP INS GCG, SST, PP, and/or C-peptide marker is greater than the expression of the NGN3, MAFA, MOX1, CER, POU5F1, AFP, SOX7, SOX1, ZIC1 and/or NFM marker in at least about 5% of the human cells, in at least about 10% of the human cells to 95% of the human cells or in at least about 98% of the human cells.

In some embodiments, the percentage of human cells in the cell cultures or populations, wherein the expression of MAFB, SYP, CHGA, NKX2.2, ISL1, PAX6, NEUROD, PDX1, HB9, GHRL, IAPP, INS GCG, SST, PP, and/or C-peptide is greater than the expression of the NGN3, MAFA, MOX1, CER, POU5F1, AFP, SOX7, SOX1, ZIC1 and/or NFM marker, is calculated without regard to feeder cells.

In certain embodiments of the present invention, cell cultures and/or cell populations comprising immature pancreatic islet hormone-expressing cells also include a medium which comprises one or more secreted hormones selected from ghrelin, insulin, somatostatin and/or glucagon. In other embodiments, the medium comprises C-peptide. In a preferred embodiment, the concentration of one or more secreted hormones or C-peptide in the medium ranges from at least about 1 pmol of ghrelin, insulin, somatostatin, glucagon or C-peptide/µg of cellular DNA to at least about 1000 picomoles (pmol) of ghrelin, insulin, somatostatin, glucagon or C-peptide/µg of cellular DNA.

Method of Producing Insulin In Vivo

In some embodiments, in vitro-derived pancreatic progenitor cells or PDX-1-positive pancreatic endoderm type cells or equivalents thereof described-above are transplanted into a mammalian subject. These methods are described in detail in International Application PCT/US2007/015536, titled METHODS OF PRODUCING PANCREATIC HORMONES, which is herein incorporated by reference in its entirety. In a preferred embodiment, the mammalian subject is a human subject. Particularly preferred subjects are those that have been identified as having a condition which limits the ability of the subject to produce sufficient levels of insulin in response to physiologically high blood glucose concentrations. A range of blood glucose levels that constitutes a physiologically high blood glucose level for any particular mammalian species can be readily determined by those of ordinary skill in the art. Any persistent blood glucose level that results in a recognized disease or condition is considered to be a physiologically high blood glucose level.

Additional embodiments of the present invention relate to an in vivo insulin secreting cell that is derived from an in vitro pluripotent stem cell or progeny thereof, e.g., multipotent cells, such as PDX-1 positive foregut endoderm cell, a PDX-1 positive pancreatic endoderm or pancreatic progenitor cell, an endocrine precursor, such as an NGN3 positive endocrine precursor, or a functional differentiated hormone secreting cell, such as an insulin, glucagon, somatistatin, ghrelin, or pancreatic polypeptide secreting cell. Any of the above-described terminally differentiated or multipotent cells can be transplanted into the host, or mammal, and mature into physiologically functional hormone secreting cells, such as insulin secreting cells, in response to host blood glucose levels. In preferred embodiments the cell does not form a teratoma in vivo, and if so formed, remains localized to the area of transplant and can be easily excised or removed. In especially preferred embodiments, the cell does not contain any karyotypic abnormality during the in vitro differentiation process, or when transplanted into the mammal in vivo, or when maturing and developing into functional islets in vivo.

Further, although embodiments described herein relate to an engineered or genetically recombinant pluripotent cell, multipotent or differentiated cell derived from the pluripotent cell, such as a human iPS cell, based on the description provided herein, it is anticipated that because iPS cells demonstrate similar physiology and gene marker expression profiles to that of hES cells and hES-derived cells, they will have similar physiological characteristics in vivo.

Method of Encapsulating Pancreatic Progenitors

In some embodiments, the pluripotent, multipotent and differentiated cell composition described herein can be encapsulated in a biological and/or non-biological mechanical device, where the encapsulated device separates and/or isolates the cell compositions from the host.

Methods of encapsulation are described in detail in U.S. Provisional Patent Application 61/114,857, filed Nov. 14, 2008, titled ENCAPSULATION OF PANCREATIC PROGENITORS DERIVED FROM HES CELLS, and U.S. Provisional Patent Application No. 61/121,086 filed Dec. 12, 2008, titled ENCAPSULATION OF PANCREATIC ENDODERM CELLS, which are herein incorporated by reference in their entireties; and which describes encapsulation of pancreatic endoderm cells using a semi-permeable membrane, e.g., a Theracyte™ or Gore device.

In one embodiment, hES-derived cells are encapsulated using a bio-compatible polyethylene glycol (PEG). PEG-based encapsulation is described in more detail in U.S. Pat. No. 7,427,415, titled IMPLANTATION OF ENCAPSULATED BIOLOGICAL MATERIALS FOR TREATING DISEASES; U.S. Pat. No. 6,911,227, entitled GELS FOR ENCAPSULATION OF BIOLOGICAL MATERIALS; and U.S. Pat. Nos. 6,911,227, 5,529,914, 5,801,033, 6,258,870, entitled GELS FOR ENCAPSULATION OF BIOLOGICAL MATERIALS, which is herein incorporated by reference in their entireties; and which describes conformal coating of cell aggregates using polyethylene glycol.

In one embodiment, the encapsulation device contains the pluripotent derived cells, for example, PDX-1 positive foregut endoderm cell, a PDX-1 positive pancreatic endoderm or progenitor cell, an endocrine precursor, such as an NGN3 positive endocrine precursor, or a functional differentiated hormone secreting cell, such as an insulin, glucagon, somatistatin, ghrelin, or pancreatic polypeptide secreting cell, in a semipermeable membrane that prevents passage of the transplanted cell population, retaining them in the device, while at the same time permitting passage of certain secreted polypeptides, e.g., insulin, glucagon, somatistatin, ghrelin, pancreatic polypeptide and the like. Alternatively, the device has a plurality of membranes, including a vascularizing membrane.

Use of Agents to Enhance and Promote Growth, Survival, Proliferation and Cell-Cell Adhesion of Human Pluripotent Stem Cells, e.g., hES Cells and iPS Cells Cellular regulation can be affected through the transduction of extracellular signals across the membrane that, in turn, modulates biochemical pathways within the cell. Protein phosphorylation represents one course by which intracellular signals are propagated from molecule to molecule resulting finally in a cellular response. These signal transduction cascades are highly regulated and often overlapping as evidenced by the existence of many protein kinases as well as phosphatases. It has been reported that in humans, protein tyrosine kinases are known to have a significant role in the development of many disease states including diabetes, cancer and have also been linked to a wide variety of congenital syndromes. Serine threonine kinases, e.g., Rho kinases, are a class of enzymes, which if inhibited can have relevance to the treatment of human disease, including diabetes, cancer, and a variety of inflammatory cardiovascular disorders and AIDS. The majority of inhibitors identified to date act at the ATP-binding site. Such ATP-competitive inhibitors have demonstrated selectivity by virtue of their ability to target the more poorly conserved areas of the ATP-binding site.

The Rho kinase family of small GTP binding proteins contains at least 10 members including Rho A-E and G, Rac 1 and 2, Cdc42, and TC10. The inhibitors are often referred to as ROK or ROCK inhibitors or Rho-kinase inhibitors, and they are used interchangeably herein. The effector domains of RhoA, RhoB, and RhoC have the same amino acid sequence and appear to have similar intracellular targets. Rho kinase operates as a primary downstream mediator of Rho and exists as two isoforms: α (ROCK2) and β (ROCK1). Rho kinase family proteins have a catalytic (kinase) domain in their N-terminal domain, a coiled-coil domain in its middle portion, and a putative pleckstrin-homology (PH) domain in their C-terminal region. The Rho-binding domain of ROCK is localized in the C-terminal portion of the coiled-coil domain and the binding of the GTP-bound form of Rho results in enhancement of kinase activity. The Rho/Rho-kinase-mediated pathway plays an important role in the signal transduction initiated by many agonists, including angiotensin II, serotonin, thrombin, endothelin-1, norepinephrine, platelet-derived growth factor, ATP/ADP and extracellular nucleotides, and urotensin II. Through the modulation of its target effectors/substrates Rho kinase plays an important role in various cellular functions including smooth muscle contraction, actin cytoskeleton organization, cell adhesion and motility and gene expression. By virtue of the role that Rho kinase proteins play in mediating a number of cellular functions perceived to be associated with the pathogenesis of arteriosclerosis, inhibitors of these kinases may also be useful for the treatment or prevention of various arteriosclerotic cardiovascular diseases and involved in endothelial contraction.

In some embodiments, agents which promote and/or support cell growth, survival, proliferation and cell-cell adhesion are added to various cell culture media conditions, including but not limited to, Rho-kinase inhibitors Y-27632, Fasudil (also referred to as HA1077), H-1152P and ITS (insulin/transferrin/selenium; Gibco), Wf-536, Y-30141 (described in U.S. Pat. No. 5,478,838, which is incorporated herein by reference in its entirety) and derivatives thereof, and antisense nucleic acid for ROCK, RNA interference inducing nucleic acid (for example, siRNA), competitive peptides, antagonist peptides, inhibitory antibodies, antibody-ScFV fragments, dominant negative variants and expression vectors thereof. Further, since other low molecular compounds are known as ROCK inhibitors, such compounds or derivatives thereof can be also used in the present invention (for example, refer to U.S. Patent Application Publication Nos. 2005/0209261, 2005/0192304, 2004/0014755, 2004/0002508, 2004/0002507, 2003/0125344 and 2003/0087919, and International Patent Application Publication Nos. WO2003/062227, WO2003/059913, WO2003/062225, WO2002/076976 and WO2004/039796, the disclosures of which are incorporated herein by reference in their entireties).

In the compositions and methods described herein, a combination of one or two or more of the ROCK inhibitors can also be used. These agents function, in part, by promoting re-association of dissociated hES cell, iPS or differentiated cell cultures, e.g., definitive endoderm, foregut endoderm, pancreatic endoderm, pancreatic epithelium, pancreatic progenitor populations, endocrine progenitors and populations and the like. Likewise, the agents can function when cell dissociation is not performed. Increase in growth, survival, proliferation and cell-cell adhesion of the human pluripotent stem cells was achieved independent of whether the cells were produced from cell aggregates in suspension or from adherent plate cultures (with or with no extracellular matrix components, with or without serum, with or without fibroblast feeders, with or without FGF, with or without Activin). Increase in survival of these cell populations facilitates and improves purification systems using a cell-sorter and, therefore allows improved recovery of the cells. Use of Rho kinase inhibitors such as Y27632 may allow for expansion of differentiated cell types as well by promoting their survival during serial passaging dissociated single cells or from cryogenic preservation. Although, Rho kinase inhibitors such as Y27632 have been tested on human pluripotent stem cells (e.g., hES and iPS cells) and differentiated cells thereof, Rho kinase inhibitors can be applied to other cell types, for example, in general, epithelial cells including but not limited to intestinal, lung, thymus, kidney as well as neural cell types like pigmented retinal epithelium.

The concentration of the ROCK inhibitor in the cell culture medium is not limited to that described in the examples below so long as the concentration can achieve the desired effects such as enhancing, increasing, and/or promoting growth, survival, proliferation and cell-cell adhesion of cells is achieved. One skilled in the art will recognize that optimization of various ROCK inhibitors under various conditions may be necessary. For example, when employing Y-27632 a preferable concentration can range from about 0.01 to about 1000 µM, more preferably about 0.1 to about 100 µM, and even more preferably about 1.0 to about 50 µM, and most preferably about 5 to 20 µM. When Fasudil/HA1077 is used, it can be used at about two or three-fold the aforementioned Y-27632 concentration. When H-1152 is used, it can be used at about fraction, e.g., about $1/10^{th}$, $1/20^{th}$, $1/30^{th}$, $1/40^{th}$, $1/50^{th}$ or $1/60^{th}$ of the amount of the aforementioned Y-27632 concentration. The concentration of ROCK-inhibitor used will depend, in part, on the bioactivity and potency of the inhibitor and the conditions in which they are used.

The time and period for treating with the ROCK inhibitor may or may not be limited depending on the desired effects such as the enhancing, increasing, and/or promoting growth, survival, proliferation (cell mass) and cell-cell adhesion. However, addition of a ROCK inhibitor may also affect differentiation in surprising ways as better described in Example 7. The Examples below describe human pluripotent stem cell cultures and/or differentiated cell cultures treated for about 12 hours, 24 hours, 48 hours, or more.

The density of the human pluripotent stem cell cultures treated with the ROCK inhibitor is also not limited as far as it is a density at which the desired effects such as the enhancing, increasing, and/or promoting growth, survival, proliferation and cell-cell adhesion of cells is achieved. The cell density of the seeded cells may be adjusted depending on a variety of factors, including but not limited to the use of adherent or suspension cultures, the specific recipe of the cell culture media used, the growth conditions and the contemplated use of the cultured cells. Examples of cell culture densities include, but are not limited to, $0.01 \times 10^5$ cells/ml, $0.05 \times 10^5$ cells/ml, $0.1 \times 10^5$ cells/ml, $0.5 \times 10^5$ cells/ml, $1.0 \times 10^5$ cells/ml, $1.2 \times 10^5$ cells/ml, $1.4 \times 10^5$ cells/ml, $1.6 \times 10^5$ cells/ml, $1.8 \times 10^5$ cells/ml, $2.0 \times 10^5$ cells/ml, $3.0 \times 10^5$ cells/ml, $4.0 \times 10^5$ cells/ml, $5.0 \times 10^5$ cells/ml, $6.0 \times 10^5$ cells/ml, $7.0 \times 10^5$ cells/ml, $8.0 \times 10^5$ cells/ml, $9.0 \times 10^5$ cells/ml, or $10.0 \times 10^5$ cells/ml, or more, e.g., up to $5 \times 10^7$ cells/mL or more, or any value in between, have been cultured with good cell growth, survival, proliferation and cell-cell adhesion.

Use of Agents which Activate TGFβ Receptor Family Members

Still in another embodiment, agents that activate TGFβ receptor family member include members of the TGFβ super family of growth factors, are described herein. As used herein, "TGFβ superfamily member" or equivalents thereof refers to over 30 structurally related proteins including subfamilies including TGFβ1, TGFβ2, TF-β3, GDF-15, GDF-9, BMP-15, BMP-16, BMP-3, GDF-10, BMP-9, BMP-10, GDF-6, GDF-5, GDF-7, BMP-5, BMP-6, BMP-7, BMP-8, BMP-2, BMP-4, GDF-3, GDF-1, GDF 11, GDF8, Activins βC, βE, βA and βB, BMP-14, GDF-14, MIS, Inhibin alpha, Lefty1, Lefty2, GDNF, Neurteurin, Persephin and Artemin See Chang et al. (2002) Endocrine Rev. 23(6):787-823.

A TGFβ family member can be replaced by, or used in conjunction with, a TGFβ signaling pathway activator, which is a compound that stimulates one or more of the polypeptides or interactions that participate in transducing or otherwise effectuating changes in the properties of a cell in response to a TGFβ family member. A TGFβ signaling pathway includes TGFβ family members themselves. TGFβ super family members transmit signals to the nucleus by signaling through type II and I serine-threonine kinase receptors and intracellular effectors known as Smads. These receptors fall into two subfamilies known as type I and type II receptors that act cooperatively to bind ligand and transduce signal (Attisano et al., Mol Cell Biol 16 (3), 1066-1073 (1996)). Ligands bind to type I and II receptors on the cell surface, promoting activation of the type I receptor via phosphorylation. This activated complex in turn activates intracellular Smads, which assemble multi-subunit complexes that regulate transcription. Members of the TGFbeta super family are divided into two signaling subgroups: those functionally related to TGFβ/Activin and those related to the BMP/GDF subfamily. Most TGFβ ligands are thought to bind first to a type II receptor and this ligand/type II receptor complex then recruits or phosphorylates a type I receptor (Mathews, L S, Endocr Rev 15:310-325 (1994); Massague, Nature Rev: Mol Cell Biol. 1, 169-178 (2000)). The type II receptor kinase by phosphorylating and activating the type I receptor kinase, which then phosphorylates and activates the Smad proteins. The TGFβ/Activin ligands bind to TGFβ and Activin type II receptors and can activate Smad-2 and -3. Nodal and Lefty signal through this Activin-type pathway. The BMP/GDF ligands bind to BMP type II receptors and can activate Smads 1, 5, and 8. See Derynck, R et al. Cell 95, 737-740 (1998)). Upon ligand stimulation, Smads move into the nucleus and function as components of transcription complexes.

TGFβ signaling is regulated positively and negatively though various mechanisms. Positive regulation amplifies signals to a level sufficient for biological activity. TGFβ superfamily ligands bind to a type II receptor, which recruits and phosphorylates a type I receptor. The type I receptor then phosphorylates receptor-regulated SMADs (R-SMADs e.g., SMAD1, SMAD2, SMAD3, SMAD5, and SMAD8) which can now bind common mediator Smad or co-SMAD. R-SMAD/coSMAD complexes accumulate in the nucleus where they act as transcription factors and participate in the regulation of target gene expression. For example, Growth differentiation factors include 1, 2, 3, 5, 6, 7, 8, 9, 10, 11, and 15. And in one preferred embodiment, GDF8 and GDF11, are TGFβ family members that are also TGFβ signaling pathway activators (positive regulation), and act by binding to the extracellular ligand binding domain portion of the ActRII receptor and then forming a complex with ActRI, leading to the inhibition of the Smad7 negative regulator and phosphorylation of the Smad2/Smad3 complex. The Smad2/Smad3 complex associates with Smad4 to regulate expression of certain genes.

Negative regulation of TGFβ signaling occurs at the extracellular, membrane, cytoplasmic and nuclear levels. Signal transduction can be interrupted in order to repress signaling initiated by TGFβ. This can be accomplished by any means known in the art in which the interaction between the TGFβ receptor(s) and the SMAD protein is antagonized or prevented, including proteins that block or compete with TGFβ receptor and SMAD protein interactions. Alternatively, the transcription or translation of TGFβ receptor or SMAD protein can be altered by any means known in the art in order to prevent signal transmission along the signaling pathway. Positive and negative regulation of various TGFβ member proteins is further exemplified by a more detail description of some of the factors below.

As with the use of any agent, the concentration of any TGFβ super family member in the cell culture medium is not limited to that described in the examples below so long as the concentration can achieve the desired effects such as to activate a TGFβ receptor family member, for example. For example, when employing Activins, e.g., Activin A and/or B, or GDF8 and GDF-11, a preferable concentration can range from about 10 to about 300 nM, more preferably about 50 to about 200 nM, and even more preferably about 75 to about 150 nM, and most preferably about 100 to 125 nM. One of ordinary skill in the art can readily test any concentration and using standard techniques in the art can determine the efficacy of such concentration, e.g., evaluating differentiation by determining expression and non-expression of a panel of gene makers for any cell type.

These and other growth factors used to differentiate human pluripotent stem cells is described in more detail in U.S. application Ser. No. 12/132,437, entitled GROWTH FACTORS FOR PRODUCTION OF DEFINITIVE ENDODERM, filed Jun. 3, 2008, which is herein incorporated by reference in its entirety.

Having generally described this invention, a further understanding can be obtained by reference to certain specific examples which are provided herein for purposes of illustration only, and are not intended to be limiting.

EXAMPLES

It should also be understood that the foregoing relates to preferred embodiments of the present invention and that numerous changes may be made therein without departing from the scope of the invention. The invention is further illustrated by the following examples, which are not to be construed in any way as imposing limitations upon the scope thereof. On the contrary, it is to be clearly understood that resort may be had to various other embodiments, modifications, and equivalents thereof, which, after reading the description herein, may suggest themselves to those skilled in the art without departing from the spirit of the present invention and/or the scope of the appended claims.

Example 1

Differentiation of Human iPS Cells to Pancreatic Progenitors and Endocrine Cells Via Definitive Endoderm and Endoderm Intermediates Human induced pluripotent stem (iPS) cells were differentiated in suspension aggregates using a four (4) stage procedure over the course of about 2 weeks (or 14 days) to generate a population of pancreatic cell types including pancreatic progenitors, endocrine progenitors and hormone expressing endocrine cells. Human iPS cell lines employed herein were provided by S. Yamanaka, Kyoto University, Japan and Cellular Dynamics International, Inc. (CDI).

The iPS cells described herein were first provided by Shinja Yamanaka and later by CDI. Undifferentiated iPS cells were grown on mitotically inactivated mouse embryo fibroblasts or preferably feeder-free (no fibroblast feeder cell layer) in DMEM/F12 containing 20% Knockout serum replacement. Differentiation was initiated by dissociating the undifferentiated iPS cells to single cells using accutase, cell samples were taken for RNA isolation & analysis. The cells were resuspended at 1-2 million cells per milliliter in RPMI+ 0.2% vol/vol FBS containing 1:5000 dilution of insulin-transferrin-selenium (ITS), activin A (100 ng/mL), wnt3a (50 ng/mL), and rho-kinase or ROCK inhibitor, Y-27632, at 10 uM, placed into an ultra-low attachment 6-well plate, placed on a rotation platform and rotated at about 100 rpm. Cultures were rotated at 100 rpm for the remainder of the differentiation process with daily media exchange. Growth, passaging and proliferation of iPSC is substantially as described in U.S. Pat. Nos. 7,961,402 and 8,211,699, the disclosures of which are incorporated herein by reference in their entireties.

The methods described herein for producing aggregate suspension cultures of pluripotent cells, e.g., hES or iPS cells, and cells derived from pluripotent cells, are as substantially described in PCT/US2007/062755, filed Feb. 23, 2007, and titled Compositions and methods for culturing differential cells and PCT/US2008/080516, filed Oct. 20, 2008, and titled Methods and compositions for feeder-free pluripotent stem cell media containing human serum, which are herein incorporated by reference in their entireties.

The methods described herein can be facilitated by first coating the culturing vessels with an extracellular matrix, e.g., as described in U.S. Pat. No. 6,800,480 to Bodnar et al. and assigned to Geron Corporation. The methods as with other methods for culturing other pluripotent stem cells, e.g., hES and iPS cells, can be cultured using soluble human serum as substantially described in U.S. application, PCT/US2008/080516, filed Oct. 20, 2008, and titled Methods and compositions for feeder-free pluripotent stem cell media containing human serum, which is herein incorporated by reference in its entirety.

The methods described herein can be facilitated by exogenously added fibroblast growth factor (FGF) supplied from a source other than just a fibroblast feeder layer as described in U.S. Pat. No. 7,005,252 to Thomson, J. and assigned to the Wisconsin Alumni Research Foundation (WARF), which is herein inspirited by reference in its entirety.

During about the first 24 hours of rotation, the single cells adhered to each other formed cell aggregates, and sufficient cell samples were taken for RNA isolation & analysis. The cell aggregates ranged from about 60 microns to 120 microns in diameter. About 1 day (or 24 hours) after the iPS cell samples were put on the rotation platform, the cultures were fed with RPMI+0.2% vol/vol FBS containing 1:5000 dilution of ITS, activin A (100-200 ng/mL), and Wnt3a (50-100 ng/mL), or about one day (time 0 to day 1) and an additional day or in the same media but without the Wnt3a (day 1 to day 2). Daily cell samples were taken for RNA isolation and analysis. After 2 days of differentiation, the cultures were fed RPMI+0.2% vol/vol FBS containing 1:1000 dilution of ITS, KGF (or FGF7, 25 ng/mL), and TGFβ inhibitor no. 4 (2.5 uM) for one day (or 24 hours, day 2 to day 3). For the next two days (day 3 to day 5) the iPS cell aggregate suspensions were fed with the same growth factor cocktail media, with the exception that the TGFβ inhibitor was removed from the culture media. Again, cell samples were taken for RNA isolation at the end of this stage (stage 2, or day 5). For stage 3 (day 5 to day 8), the cell culture media was changed to DMEM+1% vol/vol B27 supplement containing TTNPB [4-[E-2-(5,6,7,8-Tetrahydro-5,5,8,8-tetramethyl-2-naphthalenyl)-1-propenyl]benzoic acid] (3 nM), KAAD-cyclopamine (0.25 µM) and noggin (50 ng/mL). Again, cell samples were taken for RNA isolation & analysis at the end this stage (stage 3, day 8). For stage 4 (days 8 to day 14), the media was changed to DMEM+1% vol/vol B27 supplement containing Noggin (50 ng/mL), KGF (50 ng/mL) and EGF (50 ng/mL). Again, cell samples were taken for RNA isolation & analysis at the end of stage 4 (or day 14).

Real-time PCR was performed to measure the gene expression for various marker genes during the course of differentiation. Gene expression of the specific markers or genes was first normalized to the average expression levels of housekeeping genes, cyclophilin G and TATA Binding Protein (TBP) expression. Normalized relative gene expression was then displayed in the bar graphs relative to the expression level in the undifferentiated iPS cells and thus represents the fold up-regulation for the various differentiation markers. For OCT4, gene expression was normalized to set the lowest sample in the data set (day 14) and thus represents the fold down-regulation during the course of differentiation.

FIGS. 2A-L are bar graphs showing the relative gene expression of the identified gene (e.g., Oct4, Brachyury, Cer1, GSC, FOXA2, FOXA1, HNF6, PDX1, PTF1A, NKX6.1, NGN3 and INS) relative to the expression level of the same gene in the undifferentiated iPS cells. The expression level of the genes were normalized to a set of housekeeping genes (control) and comparing the gene expression level at the two different time points indicated whether the there was up- or down-regulation for that gene or expression marker. For OCT4 (FIG. 2A), the gene expression was normalized and the lowest level expression sample was set at 1 (day 14). Hence, as indicated by FIG. 2A, the relative expression levels of OCT4 represent the fold down-regulation (Y axis) during the course of differentiation (X axis, stage 0 to 4, or day 0 to day 14).

As shown in FIG. 2A, OCT4 (POU5F1) is expressed at high levels in the undifferentiated iPS cells and exhibits subsequent down regulation during the course of differentiation (day 0 to day 14). By day 14, the OCT4 expression levels were more than 3000-fold decreased from the expression levels observed in undifferentiated cells. In contrast, there was a transient up-regulation of brachyury gene (BRACHYURY, FIG. 2B) expression during the first 2 days (day 1 and day 2). Transient up-regulation of brachyury was a result of the directed differentiation of pluripotent/iPS cell into mesendoderm by the application of activin A and wnt3a. The mesendoderm was further differentiated into definitive endoderm during days 2 and 3 by continued exposure to activin A was indicated by the up-regulation of CER1, GSC and FOXA2 by the end of stage 1 at day 3 (FIG. 2C-E). During stage 2, the definitive endoderm was further directed to differentiate to gut tube endoderm as indicated by the up-regulation of FOXA1, maintenance of FOXA2 expression and down regulation of CER1 and GSC by day 6 of differentiation (FIG. 2C-F). During stage 3, upon exposure to retinoid, cyclopamine and noggin, the gut tube endoderm was further directed to differentiate to posterior forgut/PDX1-expressing endoderm as indicated by the up-regulation of HNF6 and PDX1 by day 8 (FIG. 2G-H). During stage 4, upon exposure to KGF and EGF, the posterior forgut/PDX1-expressing endoderm was further directed to differentiate to pancreatic progenitors, endocrine progenitors and hormone expressing endocrine cells as indicated by the up-regulation of PTF1A, NKX6-1, NGN3 and INS by day 14 (FIGS. 2I-L).

Example 2

Rho-Kinase Inhibitors Promote Growth, Survival, Proliferation and Cell-Cell Adhesion of IPS Cells Methods for differentiating various hES and iPS cell lines are substantially as described herein and in Example 1. In addition to the culture conditions as described for Stages 1, 2, 3, 4 and 5, apoptotic inhibitor and/or Rho-kinase or ROCK inhibitor was added to the culture media to enhance and promote growth, survival, proliferation and cell-cell adhesion during differentiation. Typically about 10 µM of a Rho-kinase inhibitor, for example, Y-27632 was added to the cell cultures at each of the stages. Alternatively, a Rho-kinase inhibitor was added to at least Stages 1 and 2 and stages 4 and 5, or any combination thereof. The morphology and gene marker expression profiles of the differentiated iPS suspension (aggregates) cell cultures are substantially similar to that of suspension cell cultures derived from hES cells.

Figure 3:
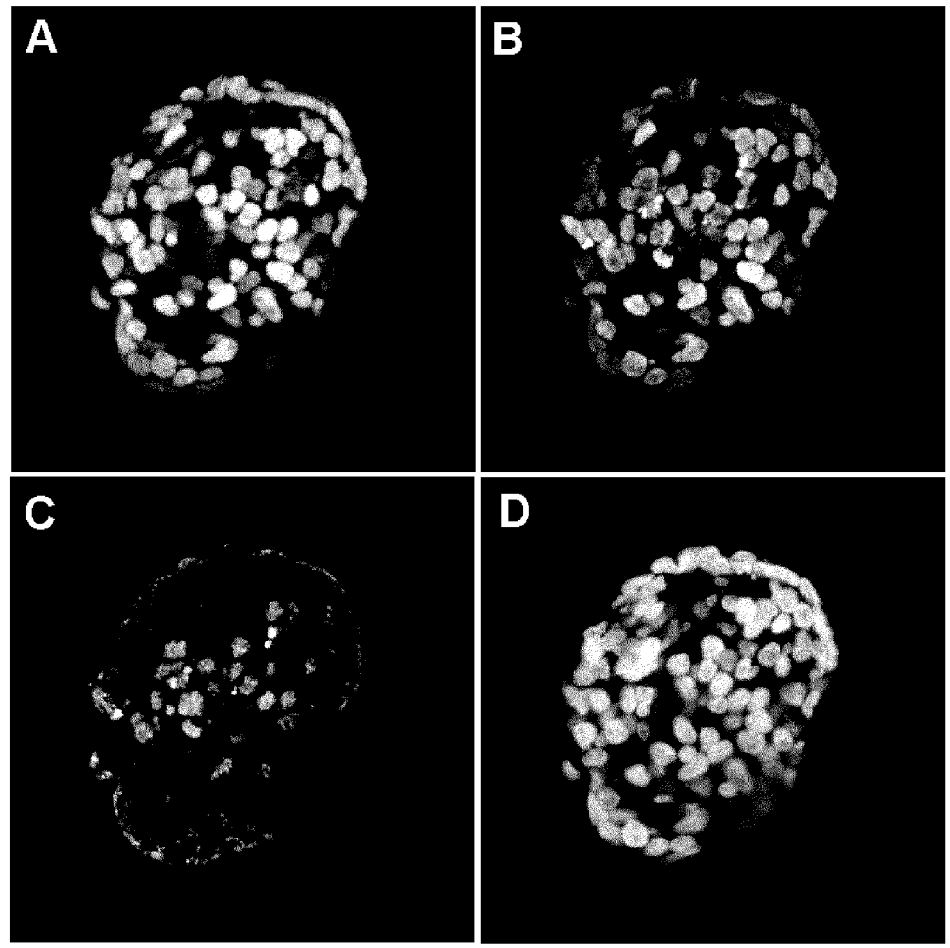
FIGS. 3A-3D are photmicrographs of immunocytochemistry (ICC) of human iPS cell cultures from Stage 4 differentiation using antibodies specific for (3A) PDX-1; (3B) NKX6.1; (3C) PTF1A; and (3D) Dapi.
Figure 4:
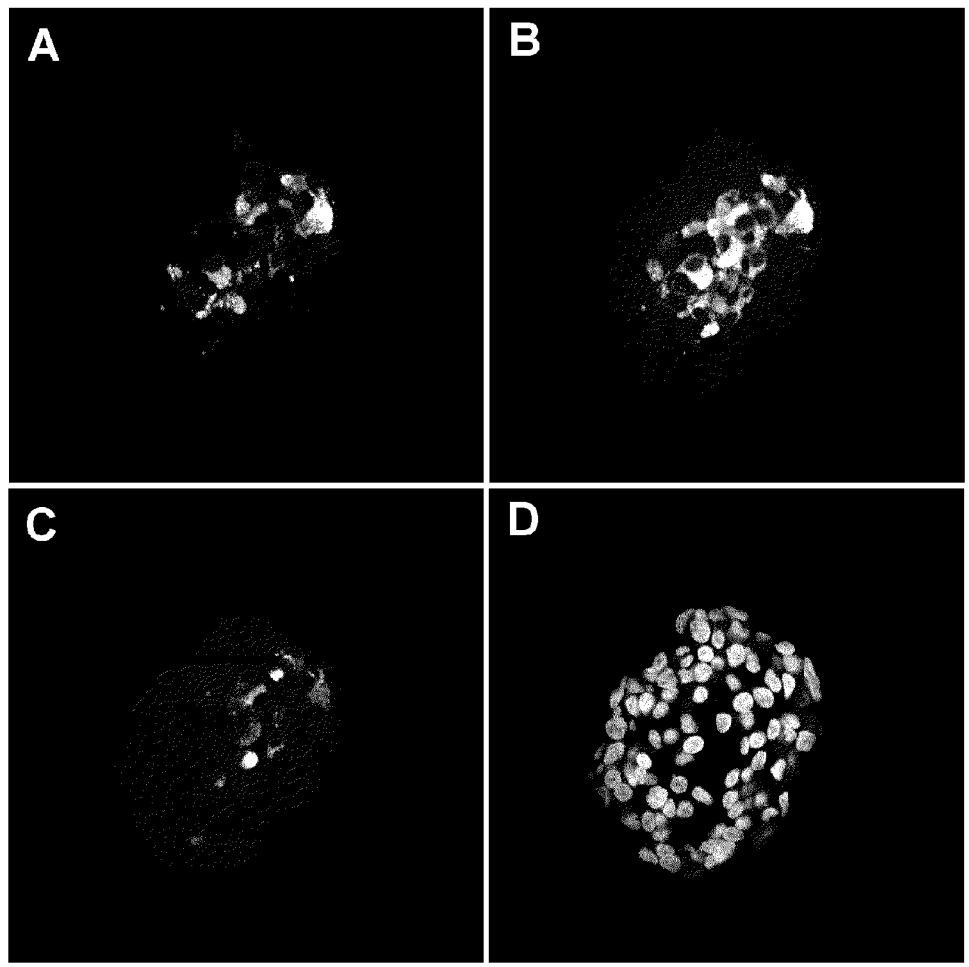
FIGS. 4A-4D are pictures of immunocytochemistry (ICC) of iPS cell cultures from Stage 4 differentiation using ligands specific for (4A) Glucagon; (4B) Insulin; (4C) Somatostatin; and (4D) Dapi.

FIGS. 3 and 4 show immunocytochemistry (ICC) of iPS cell cultures from Stages 4 & 5, respectively. FIG. 3 shows a cell aggregate from Stage 4 expressing typical gene markers characteristic of PDX1-positive pancreatic endoderm (also referred to as pancreatic epithelium or pancreatic progenitors) including PDX1/NKX6.1 co-positive cells. Although not shown in FIG. 3, Stage 4 cells do not express hormone secreting proteins or gene markers more typical of Stage 5 cells such as insulin (INS), glucagon (GCG), somatostatin (SST) and pancreatic polypeptide (PP). FIG. 4 shows cell aggregate of hormone expressing cells from Stage 5. These ICC results were further confirmed using QPCR. However, because QPCR is a total population study of the total level of RNA expressed in the sample or cell culture, it cannot definitively show that any one cell expresses multiple markers.

Example 3

Encapsulation of IPS-Derived Pancreatic Progenitors

To date, methods for production of IPS cells and sources for production of IPS cells have been reported. However, there is no sufficient description of differentiating any iPS cell to any functioning differentiated cell for potential use in a cell therapy to treat a particular disease, for example, diabetes.

To determine whether the Stage 4 PDX1-positive pancreatic endoderm or pancreatic progenitor cell cultures derived from human iPS cells were fully capable of developing and maturing in vivo to glucose sensitive insulin secreting cells, the pancreatic progenitor populations substantially as described in Examples 1 and 2 were loaded into macro-encapsulating devices substantially similar to that described in U.S. application Ser. No. 12/618,659, entitled ENCAPSULATION OF PANCREATIC LINEAGE CELLS DERIVED FROM HUMAN PLURIPOTENT STEM CELLS, filed Nov. 13, 2009; and U.S. Pat. Nos. 7,534,608 and 7,695,965 entitled METHODS OF PRODUCING PANCREATIC HORMONES, which are herein incorporated by reference in their entireties. In brief, about 5-10-20 µL gravity settled cell suspension aggregates were loaded into each device, having substantially about $3 \times 10^6$ cells.

The encapsulated cells in the device were then prepared for implantation into a mammal, for example an immuno-compromised SCID/Bg mice, but can be implanted in larger animals including rats, pigs, monkey or human patient. Methods of implanting the encapsulated cells and device are substantially as that described U.S. patent application Ser. No. 12/618,659, U.S. Pat. Nos. 7,534,608 and 7,695,965, including pancreatic progenitor cells implanted on a GELFOAM matrix and implanted under the epididymal fat pad (EFP).

No immuno-suppression was necessary in these studies, however, immuno-suppression may be required for certain mammals for an initial interim period until the progenitors inside the device fully mature and are responsive to glucose.

In some mammals immuno-suppression regimens may be for about 1, 2, 3, 4, 5, 6 or more weeks, and will depend on the mammal.

The transplanted cells were allowed to differentiate and further mature in vivo. To determine whether the transplanted cells had normal physiological function as a naturally occurring beta cell for example, levels of human insulin will be determined by testing levels of human C-peptide. Human C-peptide is cleaved or processed from human pro-insulin, hence, the detection of human C-peptide specifically, and not endogenous mouse C-peptide, indicates that insulin secretion is derived from the grafted (exogenous) cells. The animals with implants will be tested for levels of human C-peptide about every two, three or four weeks by injecting them with a bolus of arginine or glucose, preferably glucose. The then mature beta cells (derived from differentiated pluripotent iPS cells) should be physiologically functional and responsive to glucose not unlike naturally occurring or endogenous beta cells. Typically amounts of human C-peptide above 50 pM or the average basal (threshold) level, is an indicator of function of the now beta cells from the transplanted progenitors.

Similar to that described in Kroon et al. (2008) supra U.S. patent application Ser. No. 12/618,659, U.S. Pat. Nos. 7,534,608; 7,695,965 and 7,993,920, which are all incorporated herein by reference in their entireties, the encapsulated pancreatic progenitors derived from hIPS cells are expected to mature into functioning pancreatic islet clusters having endocrine, acinar and ductal cells not unlike that in naturally occurring islets. It is also anticipated that purified or enriched pancreatic progenitors derived from hIPS cells before transplantation will also mature and develop into functioning pancreatic islets and produce insulin in vivo. Certain embodiments for purifying and enriching various differentiated cell populations is described in more detail in U.S. patent application Ser. No. 12/107,020, entitled METHODS FOR PURIFYING ENDODERM AND PANCREATIC ENDODERM CELLS DERIVED FROM HES CELLS, filed Apr. 8, 2008, now U.S. Pat. No. 8,338,170, the disclosure of which is incorporated herein by reference in its entirety. It is further anticipated that pancreatic progenitors derived from hIPS cells which have been cryopreserved can be thawed and adapted in culture before transplantation and mature and produce insulin in vivo accordingly. And that hypoglycemia can be ameliorated in diabetic induced animals having the transplanted pancreatic progenitors derived from hIPS cells.

In summary, wholly encapsulated pancreatic progenitor cells derived from hIPS cells in a macro-encapsulating device mature into physiologically functional pancreatic islets and are expected to produce insulin in response to glucose in vivo.

Example 4

Pancreatic Progenitor and Hormone Secreting Cell Compositions

Differentiated hIPS cell populations were analyzed using flow cytometry for their content of PDX1-positive pancreatic endoderm or pancreatic progenitor cells (at stage 4); and endocrine or endocrine precursor cells (at stage 5) as shown in Tables 5a, 5b and 6, respectively. Table 5b is the same data set as that in Table 5a, but presented similar to that of Table 9 for comparison. Table 5a populations overlap each other, e.g. the total cell number is greater than 100% because the total PDX1+ and NKX6.1+ numbers overlap with that of the NKX6.1+/PDX1+/CHGA− cell population (5$^{th}$ column of Table 5a). Table 5b, includes the PDX1+ only and triple negative (residual) data, which is not shown in Table 5a. Certain of these iPEC grafts as well as others using substantially similar formulations did get implanted into animals to determine in vivo function, however, levels of human serum C-peptide was not sufficiently robust for any potential therapeutic purpose (data not shown). Values shown are the percentage of total cells which belong to a given population. The numbers of the pancreatic progenitors (NKX6.1(+)/PDX1(+)/ChromograninA(−)) and a very small population of NKX6.1+/PDX1−/CHGA− are in the suspension cell aggregates were consistent with that observed in pancreatic progenitor cell suspension aggregates derived from hES cells and aggregated at the ESC stage as described in U.S. application Ser. No. 12/264,760, entitled STEM CELL AGGREGATE SUSPENSION COMPOSITIONS AND METHODS OF DIFFERENTIATION THEREOF, filed Nov. 4, 2008 and incorporated herein by reference in its entirety. Levels of endocrine and/or endocrine precursor cells were also substantially consistent with that obtained in hES-derived cell cultures in U.S. application Ser. No. 12/107,020, entitled METHODS FOR PURIFYING ENDODERM AND PANCREATIC ENDODERM CELLS DERIVED FROM HES CELLS, filed Apr. 8, 2008, which is herein incorporated in its entirety by reference in its entirety. Similar to hES-derived cell suspension aggregates, varying the concentrations of different growth factors in the culture medium at certain stages of differentiation (e.g., stage 4) should increase and/or decrease certain populations of pancreatic endoderm, endocrine, PDX1-positive endoderm or non-pancreatic cell types.

TABLE 5a

Stage 4 Pancreatic Progenitor Cell Compositions (Percent of total cells)

| Exp. # | iPS Cell line | PDX1+ | NKX6.1+ | Pancreatic Endoderm (NKX6.1(+)/PDX1(+)/ChromograninA(−)) | Endocrine (ChromograninA+) |
|---|---|---|---|---|---|
| 1 | G4 | 56.4 | 39.2 | 33.3 | 12.7 |
| 2 | B7 | 88.3 | 40.9 | 30.4 | 42.3 |
| 3 | B7 | 84.1 | 53.1 | 38.8 | 51.8 |
| 4 | B7 | 94.0 | 43.7 | 32.7 | 49.5 |

TABLE 5b

Stage 4 Pancreatic Progenitor Cell Compositions (Percent of total cells)

| Exp. # | Conditions | PEC CHGA+ (Endocrine) | CHGA− NKX6.1+ PDX1+ or − (Pancreatic Progenitors, >96% PDX1+) | CHGA− NKX6.1− PDX1+ (PDX1+ only) | CHGA− NKX6.1− PDX1− (Triple negative; residual cells) |
|---|---|---|---|---|---|
| 1 | Baseline | 12.7 | 33.3 | 10.6 | 42.7 |
| 2 | Baseline | 42.3 | 30.4 | 18.5 | 7.9 |

TABLE 5b-continued

Stage 4 Pancreatic Progenitor Cell Compositions (Percent of total cells)

| | | PEC | | | |
|---|---|---|---|---|---|
| Exp. # | Conditions | CHGA+ (Endocrine) | CHGA– NKX6.1+ PDX1+ or – (Pancreatic Progenitors, >96% PDX1+) | CHGA– NKX6.1– PDX1+ (PDX1+ only) | CHGA– NKX6.1– PDX1– (Triple negative; residual cells) |
| 3 | Baseline | 51.8 | 38.8 | 8.4 | 0.5 |
| 4 | Baseline | 49.5 | 32.7 | 16.3 | 1.2 |

TABLE 6

Stage 5 Endocrine Cell Compositions (Percent of total cells)

| Exp. # | iPS Cell Line | Insulin+ | Glucagon+ | Somatostatin+ |
|---|---|---|---|---|
| 5 | B7 | 15.9 | 15.0 | 12.1 |
| 6 | B7 | 17.4 | 15.9 | 10.5 |

Example 5

PEC Receptor Tyrosine Kinases

The above described methods are substantially similar to those described in Table 7 below, adapted from Schulz et al., (2012), supra. These and other methods described herein can be found in Applicant's many patent and non-patent publications including U.S. Pat. Nos. 7,964,402; 8,211,699; 8,334,138; 8,008,07; and 8,153,429, the disclosures of which are all incorporated herein by reference in their entireties.

TABLE 7

Standard Manufacturing Method for Making Pancreatic Endoderm Cells (PEC) Derived from hESC

| Time point (day) | Stage (1-4) | Media Condition | Roller Bottle Speed (rpm) | 6-well tray Speed (rpm) |
|---|---|---|---|---|
| d(−1) | | hESC XF HA; SP Agg. | 5-10 | 95 |
| d0 | 1 | r0.2FBS-ITS1:5000 A100 W50 | 5-10 | 95 |
| d1 | | r0.2FBS-ITS1:5000 A100 | 5-10 | 95 |
| d2 | 2 | r0.2FBS-ITS1:1000 K25 IV | 5-10 | 95 |
| d3 | | r0.2FBS-ITS1:1000 K25 | 5-10 | 95 |
| d4 | | r0.2FBS-ITS1:1000 K25 | 5-10 | 105 |
| d5 | 3 | db-CTT3 N50 | 5-10 | 105 |
| d6 | | db-CTT3 N50 | 5-10 | 105 |
| d7 | | db-CTT3 N50 | 5-10 | 105 |
| d8 | 4 | db-N50 K50 E50 | 5-10 | 105 |
| d9 | | db-N50 K50 E50 | 5-10 | 95 |
| d10 | | db-N50 K50 E50 (or no feed) | 5-10 | 95 |
| d11 | | db-N50 K50 E50 | 5-10 | 95 |
| d12 | | db-N50 K50 E50 | 5-10 | 95 | hESC Agg.: hESC aggregates; XF HA: DMEM/F12 containing GlutaMAX, supplemented with 10% v/v of Xeno-free KnockOut Serum Replacement, 1% v/v non-essential amino acids, 0.1 mM 2-mercaptoethanol, 1% v/v penicillin/streptomycin (all from Life Technologies), 10 ng/mL heregulin-1β (Peprotech) and 10 ng/mL activin A (R&D Systems); SP: StemPro® hESC SFM (Life Technologies); r0.2FBS: RPMI 1640 (Mediatech); 0.2% FBS (HyClone), 1x GlutaMAX-1 (Life Technologies), 1% v/v penicillin/streptomycin; ITS: Insulin-Transferrin-Selenium (Life Technologies) diluted 1:5000 or 1:1000; A100: 100 ng/mL recombinant human Activin A (R&D Systems); W50: 50 ng/mL recombinant mouse Wnt3A (R&D Systems); K25: 25 ng/mL recombinant human KGF (R&D Systems); IV: 2.5 μM TGF-β RI Kinase inhibitor IV (EMD Bioscience); db: DMEM HI Glucose (HyClone) supplemented with 0.5x B-27 Supplement (Life Technologies), 1x GlutaMAX, and 1% v/v penicillin/streptomycin; CTT3: 0.25 μM KAAD-Cyclopamine (Toronto Research Chemicals) and 3 nM TTNPB (Sigma-Aldrich); N50: 50 ng/mL recombinant human Noggin (R&D Systems); K50: 50 ng/mL recombinant human KGF (R&D Systems); E50: 50 ng/mL recombinant human EGF (R&D Systems); no feed: indicates that cells were not re-fed on the indicated day; db, DMEM (high-Glucose)

When the above methods were applied to iPS cells and the pancreatic progenitors transplanted in animals, Applicant did not consistently obtain the same robust in vivo function as compared to when the same methods were applied to hESC and hES-derived pancreatic progenitors. This was surprising given iPS cells are human pluripotent stem cells that have the morphology and gene-expression pattern of hESCs and can form both embryoid bodies in vitro and teratomas in vivo, indicating that they can form cells from all three germ layers. See at least for example Yu et al. (2007); U.S. Patent Application Publication No. 2009/0047263, International Patent Application Publication No. WO2005/80598; U.S. Patent Application Publication No. 2008/0233610; and International Patent Application Publication No. WO2008/11882, supra. These references describe that iPS cells meet the defining criteria for ESC. Hence, there is an expectation that iPS cells can substitute for ESCs in an in vitro differentiation protocol that yields hES-derived pancreatic progenitor cells that further mature and develop into fully functioning glucose responsive cells in vivo. However, given the inconsistent in vivo functioning data using the above methods, Applicants sought to explore a differentiation media formulation unique to pancreatic progenitors and/or pancreatic endoderm cells (PEC) i.e., stage 4 derived cells from hiPSC (or "iPEC") that are capable of providing substantially similar robust levels of in vivo function which has been consistently observed for PEC derived from hESC.

Applicants previously reported that endocrine (CHGA+ cells) cells present in PEC are polyhormonal endocrine cells and are not the sub-population of cells in PEC that give rise to islets having glucose-responsive insulin-secreting cells in vivo. See Kelly et. al. (2011) supra. Rather it is the non-endocrine cell population (CHGA– cells), especially those that co-express NKX6.1 and PDX-1, that are believed to be the PEC that actually give rise to the functioning islets in vivo. Thus, Applicant's explored whether modulating, changing or shifting the relative ratios of endocrine and non-endocrine sub-populations might affect later in vivo function.

Previous efforts to decipher receptor-ligand signaling in hESC successfully identified growth factors that promoted self-renewal and enabled the development of defined media culture conditions. See Wang et al (2007) supra. Wang et al. identified heregulin-1β as the ligand that bound to ERBB3 and induced dimerization with ERBB2 to affect self-renewal of hESC in that context. ERBB is a receptor tyrosine kinase (RTK) and RTK are widely expressed transmembrane proteins that act as receptors for growth factors and other extracellular signaling molecules. Upon ligand binding, they undergo tyrosine phosphorylation at specific residues in the cytoplasmic tail and setting off a signaling cascade for the binding of other protein substrates involved in RTK-mediated signal transduction. RTK function in several developmental processes, including regulating cell survival, proliferation, and motility and their role in cancer formation is well documented. ERBB tyrosine kinase receptors were also known to be expressed throughout the developing fetal human pancreas although specific roles of certain ERBB receptors and their ligands are unknown. See Mari-Anne Huotari et al. (2002) ERRB Signaling Regulates Lineage Determination of Developing Pancreatic Islet Cells in Embryonic Organ Culture, *Endocrinology* 143(11): 4437-4446.

Because of the role of ERBB RTK signaling in pluripotent stem cell self-renewal and their expression in fetal human pancreas as demonstrated by Wang et al. (2007) supra and ERBB RTK expression in the human fetal pancreas, Applicants then turned to investigate the potential activation of RTK in in vitro pancreatic endoderm cells (PEC) derived from hESC in an effort to identify receptors and ligands that might improve PEC specification during differentiation, or expansion via promotion of self-renewal, or some other unknown mechanism which promotes maturation to physiologically functioning islet hormone secreting cells in vivo. PEC were generated in suspension in differentiating aggregates, substantially as described in Table 7, except with the following modifications.

Four PEC samples were generated for RTK blotting analysis. A "steady state" sample of PEC aggregates in db-N50 K50 E50 was collected at the end of stage 4 (or d13). A "starved" sample represented d12 PEC aggregates that were fed with db (DMEM high-glucose or DMEM high-glucose supplemented with 0.5×B-27 Supplement (Life Technologies)) media alone (no growth factors) and collected on d13. Two "pulsed" samples were fed and cultured in db media on d12, then on d13 fed with either db-K50 E50 media, or db media containing 2% FBS, for 15 minutes prior to harvesting. Such conditions were intended to detect RTKs that were active in stage 4 conditions, and what response could be elicited with a pulse of KGF, EGF and insulin (present in the B27 supplement), or serum. The serum pulse was intended as a broad-spectrum, growth factor stimuli, potentially identifying RTKs that are present on PEC and can be activated, but are not stimulated with the present stage 4 conditions.

Figure 5:
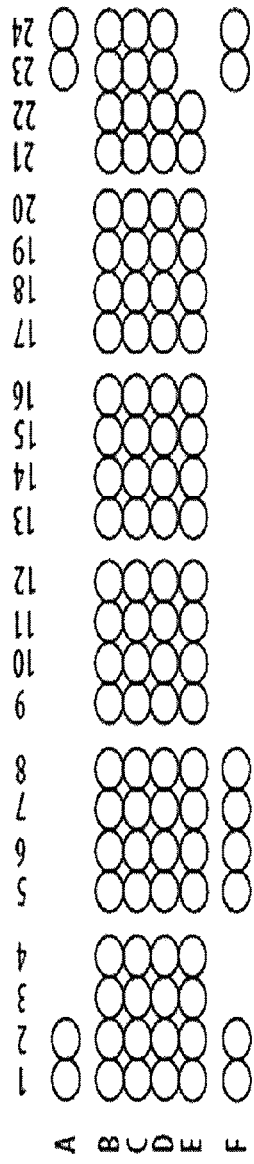
FIGS. 5A-B are an array location map and array key provided in the Proteome Profiler™ human phospho-RTK antibody arrays from R&D Systems. The location map in FIG. 5A shows the coordinates or location of the RTK antibodies. The identity or name of the RTK family and antibodies are described in the key, FIG. 5B. The positive signals observed on the developed film can therefore be identified by overlaying a transparency as in FIG. 5A and identifying the signals by referring to the coordinates on the overlay (FIG. 5A) with the name of the RTK in FIG. 5B.

RTK analysis was performed essentially as described previously in Wang et al, (2007) supra. Briefly, Proteome Profiler™ human phospho-RTK antibody arrays (R&D Systems) were used according to the manufacturer's instructions. Protein lysates were prepared in 1% NP-40, 20 mM Tris-HCl (pH 8.0), 137 mM NaCl, 10% glycerol, 2.0 mM EDTA, 1.0 mM sodium orthovanadate, 10 μg/mL Aprotinin, and 10 μg/ml Leupeptin. 500 μg fresh protein lysates were incubated overnight with nitrocellulose membranes dotted with duplicate spots for 42 anti-RTK antibodies and 5 negative control antibodies, as well as 8 anti-phosphotyrosine positive control spots (FIG. 5A). The arrayed antibodies capture the extracellular domains of both phosphorylated and unphosphorylated RTKs, and bound phospho-RTKs are detected with a pan anti-phospho-tyrosine antibody conjugated to horseradish peroxidase (HRP) using chemiluminescence. See FIG. 5 for the RTK array layout as well as Table 8 below for the listing of RTK in the array.

TABLE 8

Listing of Receptor Tyrosine Kinase (RTK) for RTK Analysis of PEC

| Receptor Family | RTK |
| --- | --- |
| EGF R | EGFR |
| EGF R | ERBB2 |
| EGF R | ERBB3 |
| EGF R | ERBB4 |
| FGF R | FGF R1 |
| FGF R | FGF R2A |
| FGF R | FGF R3 |
| FGF R | FGF R4 |
| Insulin R | Insulin R |
| Insulin R | IGF-1R |
| Axl | Axl |
| Axl | Dtk |
| Axl | Mer |
| HGF R | HGF R |
| HGF R | MSP R |
| PDGF R | PDGF Ra |
| PDGF R | PDGF Rb |
| PDGF R | SCF R |
| PDGF R | Flt-3 |
| PDGF R | M-CSF R |
| RET | c-Ret |
| ROR | ROR1 |
| ROR | ROR2 |
| Tie | Tie-1 |
| Tie | Tie-2 |
| NGF R | TrkA |
| NGF R | TrkB |
| NGF R | TrkC |
| VEGF R | VEGF R1 |
| VEGF R | VEGF R2 |
| VEGF R | VEGF R3 |
| MuSK | MuSK |
| Eph R | EphA1 |
| Eph R | EphA2 |
| Eph R | EphA3 |
| Eph R | EphA4 |
| Eph R | EphA6 |
| Eph R | EphA7 |
| Eph R | EphB1 |
| Eph R | EphB2 |
| Eph R | EphB3 |
| Eph R | EphB4 |
| Eph R | EphB6 |
| Insulin R | ALK |

Analysis of the RTK blots (FIG. 6A) indicated that the insulin- and IGF1-Receptors (IR, IGF1R, respectively) were phosphorylated and activated in all conditions, similar to that observed previously with hESC. See Wang et al (2007) supra. The EGF receptor (EGFR, also known as ERBB1) was phosphorylated in steady state conditions, which was expected given the presence of EGF in the stage 4 medium. Indeed, low-level phosphorylation of ERBB2 was detected in both the steady state and starved conditions. Phosphorylation of both EGFR and ERBB2 was elevated in each of the pulsed conditions, confirming the capability of the assay to detect activation in response to a pulse of ligand. Phosphorylated VEGFR3 was also detected in all conditions and was elevated in the pulsed samples. This suggested that PEC produces an endogenous VEGFR3 ligand, possible candidates being VEGF-C and D. The serum pulse appeared to activate additional receptors, including low levels of ERBB3 phosphorylation. The detection of phosphorylated ERBB2/3 is suggestive that a heregulin-like EGF-family member could activate signaling in PEC. TIE-2 is one of two angiopoietin receptors and appeared to be phosphorylated at a low level in response to serum. Angiopoietin 1 and Angiopoietin 4 are known to be activating ligands of Tie-2, whereas Angiopoietin 2 and Angiopoeitin 3 function as context dependent competitive antagonists. The HGF-receptor (HGFR) was also phosphorylated in response to the serum pulse, suggesting that hepatocyte growth factor could also elicit signaling in PEC. Finally, while low-level phosphorylation of the ephrin B2 RTK (EPHB2) was detected, ephrin/Eph signaling is a membrane bound cell-cell signaling system and not likely to be exploited easily in PEC differentiation. Interestingly, ERBB4 was not phosphorylated. RTK analysis therefore highlighted several receptors that are phosphorylated in PEC, or can become phosphorylated in response to different conditions, e.g. serum. These results suggest that several soluble ligands may elicit RTK signaling in PEC and potentially impact cell proliferation, differentiation and/or specification, and therefore, potentially affect later maturation into functioning pancreatic islets in vivo.

Example 6

Heregulin and FGF2 Growth Factors Affect PEC Derived from hESC Compositions

In view of the RTK analyses, which demonstrated that certain RTK were activated (or phosphorylated) under certain conditions as described above in Example 5, and because it appeared that at least ERBB2 and ERBB3 were activated in PEC (after 13 days of differentiation from stages 1-4), Applicant sought to determine the effect of heregulin when applied to stage 3 and 4 cells.

Preliminary studies were performed using Heregulin and FGF. In certain of these studies, Rho-kinase inhibitor, Y-27632, was included. These preliminary studies showed that treatment of pluripotent stem cells for one day at stage 1 with 10 ng/mL Heregulin-1β (the same concentration and heregulin isomer as disclosed in Wang et al. (2007)) increased the cell aggregate size of the hES-derived cell aggregates in suspension culture as compared to the aggregate size of the hES-derived cell aggregates in suspension culture without Heregulin-1β (Hrg1β). An increase in cell aggregate size is advantageous in that it results in higher cell mass for later implantation and testing for function in animals. In addition, aggregate disk size increased when Hrg1β was increased from 10 ng/mL to 50 ng/mL at stage 3. This result was also observed when 50 ng/mL of another growth factor, FGF2, was used at stage 3 as compared to cultures in the absence of FGF2. An increase in cell aggregate size was also observed when the stage 3 cultures were exposed to additional days of FGF2 exposure, e.g. 3 days of 50 ng/mL FGF2 as compared to 2 days.

Table 9 provides a summary of the flow cytometry analysis of PEC cells treated with Hrg1β and FGF2 at stage 3 and/or 4. The endocrine cells are denoted as CHGA positive (or CHGA+) cells and the non-endocrine cells are denoted as CHGA negative (or CHGA−) cells. The endocrine (CHGA+) and non-endocrine cells (CHGA−) may stain positive for other markers, e.g., positive for PDX1 and/or NKX6.1. Cells which do not stain with any of the tested markers are denoted as triple negative cells or residual cells (CHGA−/NKX6.1−/PDX1).

TABLE 9

Flow Cytometry Analysis of PEC Derived From hESC and Treated With Heregulin and/or FGF2

| | PEC | | |
|---|---|---|---|
| Treatment | CHGA+) (Endocrine | CHGA−, NKX6.1+, PDX1+ (Non-endocrine) | CHGA− NKX6.1− PDX1− (Triple Negative/ Residual Cells) |
| No Hrg & No FGF2 | 32.9 | 54.01 | 13.1 |
| Stg 3 Hrg10 | 30.3 | 61.2 | 8.55 |
| Stg 3Hrg50 | 28.9 | 64.2 | 6.9 |
| 2d Stg 3 FGF2-50 | 11.9 | 79 | 9.15 |
| 3d Stg 3 FGF2-50 | 0.33 | 76.9 | 22.7 |

Hg, Heregulin-β; FGF2, Fibroblast growth factor 2; Hrg10, 10 ng/mL Heregulin-1β; Hrg50, 50 ng/mL Heregulin-1β; 2d FGF-50, 50 ng/mL of FGF2 for 2 days at stage 3; 3d FGF2-50, 50 ng/mL of FGF2 for 3 days at stage 3

To determine whether the increase in cell aggregate size affected the PEC sub-populations, the composition of the PEC populations was analyzed by flow cytometry. As compared to the control cultures, whereby no Hrg1β and FGF2 were used to differentiate the cells, the PEC non-endocrine sub-population (CHGA−) increased from 54.01% to 61.2% with the addition of 10 ng/mL Hrg1β at stage 3, and increased from 54.01% to 64.2% with the addition of 50 ng/mL Hrg1β at stage 3. The endocrine sub-population (CHGA+) was not significantly affected with the treatment of 10 ng/mL Hrg1β but more so with 50 ng/mL. Meanwhile, the relative levels of residual cells did decrease and more so with 50 ng/mL Hrg1β. So, the increase in cell aggregate size with Hrg1β treatment was mostly attributed to the increase in non-endocrine sub-populations relative to the endocrine and residual sub-populations.

The effect of FGF2 in the stage 3 cultures was similar but even more pronounced than that for Hrg1β. For example, the PEC non-endocrine sub-population (CHGA−) increased as it did for Hrg1β. The major effect of FGF2 in these cultures was the substantial decrease in the endocrine sub-population. In some instances, these cells were almost non-detectable with 3 days of treatment (32.9% to 0.33%). Hence, the increase in cell aggregate size for cultures treated with FGF2 was mostly attributed to the increase in non-endocrine, and in some instances, residual cell sub-populations (13.1% to 22.7% for 3 days at stage 3).

Thus, heregulin and/or FGF2 appear to play a role in the specification of cells in PEC populations. This is surprising given that Wang et al (2007) supra reported that heregulin alone played a role in cell renewal when used in the context with pluripotent stem cells.

Example 7

Methods for Improving In Vivo Graft Function of PEC by Treatment of IPS-Derived Cell Cultures with Heregulin Because the methods according to Table 7 when applied to iPSC to produce iPEC did not provide robust in vivo function in animals, Applicants explored other methods for iPEC production. Changes to the standard method as set forth in Table 7 include, but are not limited to: optimization of the number of times any iPSC is passaged; modulating levels of BMP signaling; modulating iPSC suspension aggregation parameters during expansion and differentiation (e.g. shear force, rotation speed and the like); optimization of the concentrations, time of use and duration of use of growth factors, such as Wnt, Activin and rho-kinase inhibitors; and treatment with other growth factors at various stages 1 through 4 of the differentiation protocol as candidates for improving cell mass, proliferation, differentiation, survival and the like (e.g. ERBB ligands). These many iterative experiments were tested alone, or in combination, to determine how differentiation methods for iPSC during stages 1-4 could be optimized. Such optimized differentiation methods produce iPEC populations that when grafted, resulted in robust glucose-responsive insulin-secreting cells in vivo similar to those observed and reported for hESC. Table 10 below describes the baseline conditions, with and without heregulin, that were demonstrated to differentiate iPSC to iPEC, which later matured to glucose-responsive islet cells in vivo. The baseline conditions were similar to those described in Examples 1, 2 and 5 as well as Table 7 herein, except that heregulin was added at stages 3 and 4. Although 30 ng/mL of Hrg1β was used, concentrations ranging from 10 ng/mL to 50 ng/mL, or even greater than 50 ng/mL are suitable. Also, addition of a rho-kinase inhibitor, Y-27632, was maintained in the differentiation cultures as described in Example 2.

TABLE 10

Comparison of Baseline and Heregulin Differentiation Media Formulations for Making Pancreatic Endoderm Cells (PEC) Derived from iPSC

| Baseline (No Heregulin) | Stage (1-4) | Baseline With Heregulin |
|---|---|---|
| 20% KSR-F10 A10 Y10 | iPSC Agg. | 20% KSR-F10 A10 Y10 |
| r0.2FBS-ITS1:5000 A100 W100 Y10 | 1 | r0.2FBS-ITS1:5000 A100 W100 Y10 |
| r0.2FBS-ITS1:5000 A100 Y10 |  | r0.2FBS-ITS1:5000 A100 Y10 |
| r0.2FBS-ITS1:1000 IV K25 Y10 | 2 | r0.2FBS-ITS1:1000 IV K25 Y10 |
| r0.2FBS-ITS1:1000 K25 Y10 |  | r0.2FBS-ITS1:1000 K25 Y10 |
| r0.2FBS-ITS1:1000 K25 |  | r0.2FBS-ITS1:1000 K25 |
| db- CTT3 N50 | 3 | db- CTT3 N50 H30 |
| db- CTT3 N50 |  | db- CTT3 N50 H30 |
| db- CTT3 N50 |  | db- CTT3 N50 H30 |
| db- N50 K50 E50 Y10 | 4 | db- N50 K50 E50 H30 Y10 |
| db- N50 K50 E50 Y10 |  | db- N50 K50 E50 H30 Y10 |
| db-N50 K50 E50 (or no feed) |  | db-N50 K50 E50 (or no feed) |
| db- N50 K50 E50 Y10 |  | db- N50 K50 E50 H30 Y10 |
| db- N50 K50 E50 Y10 |  | db- N50 K50 E50 H30 Y10 | iPSC Aggs: iPSC aggregates; KSR: knock-out serum (Life Technologies); F10: 10 ng/mL bFGF (R&D Systems); A10: 10 ng/mL Activin A (R&D Systems); A100: 100 ng/mL Activin A; r0.2FBS: RPMI 1640 (Mediatech), 0.2% FBS (HyClone), 1x GlutaMAX-1 (Life Technologies), 1% v/v penicillin/streptomycin; ITS: Insulin-Transferrin-Selenium (Life Technologies) diluted 1:5000 or 1:1000; A100: 100 ng/mL recombinant human Activin A (R&D Systems); K25: 25 ng/mL recombinant human KGF (R&D Systems); CTT3: 0.25 µM KAAD-Cyclopamine (Toronto Research Chemicals) and 3 nM TTNPB (Sigma-Aldrich); N50: 50 ng/mL recombinant human Noggin (R&D Systems); K50: 50 ng/mL recombinant human KGF (R&D Systems); E50: 50 ng/mL recombinant human EGF (R&D Systems); Y10: 10 uM Y-27632; stock 20 mM, 2000X; H30: 30 ng/mL Heregulin (stock 100 ug/ml); db, DMEM (high-Glucose)

To determine the effect of the addition of heregulin or heregulin and a rho-kinase inhibitor on stage 3 and 4 cell subpopulations, iPEC populations were analyzed by flow cytometry. Table 11 provides a summary of the flow cytometry analysis of various iPEC populations using the formulations set forth in Table 10, as well as such formulations having been modified by increasing the Activin concentration to 200 ng/mL. In addition, Table 11 shows the general conditions used for each set of experiments (baseline with or without heregulin) and the relative percentages of the types of cells in the iPEC population (endocrine, non-endocrine, PDX1 only and triple negative or residual cell sub-populations). Table 11 also discloses data regarding in vivo function of the cells produced in each experiment.

TABLE 11 iPEC Compositions from Heregulin Treated iPS-derived Cell Cultures

| Exp. No. | Conditions | PEC | | | | In Vivo Function |
|---|---|---|---|---|---|---|
| | | CHGA+ (Endocrine) | CHGA-NKX6.1+PDX1+ (Non-endocrine) | CHGA-NKX6.1-PDX1+ (PDX1 only) | CHGA-NKX6.1-PDX1- (Triple negative/ residual cells) | |
| E2314 | BL-hIPSC | 19.83 | 65.59 | 11.32 | 3.20 | FIG. 7A |
| | Hg30 St 3 + 4 | 9.00 | 64.21 | 16.83 | 9.88 | |

TABLE 11-continued iPEC Compositions from Heregulin Treated iPS-derived Cell Cultures

| | | PEC | | | | |
|---|---|---|---|---|---|---|
| Exp. No. | Conditions | CHGA+ (Endocrine) | CHGA-NKX6.1+PDX1+ (Non-endocrine) | CHGA-NKX6.1-PDX1+ (PDX1 only) | CHGA-NKX6.1-PDX1- (Triple negative/residual cells) | In Vivo Function |
| E2344 | BL-hIPSC | 56.51 | 36.15 | 5.45 | 1.80 | Not transplanted |
|  | Hg30 St 3 + 4 | 36.13 | 49.00 | 11.23 | 2.75 |  |
| E2347 | BL-hIPSC | 49.78 | 37.16 | 10.97 | 2.11 | FIG. 7B & 8A-B |
|  | Hg30 St 3 + 4 | 17.27 | 68.91 | 12.30 | 1.68 |  |
| E2380 | BL-hIPSC | 41.16 | 38.18 | 12.08 | 9.10 | FIG. 7A |
|  | Hg30 St 3 + 4 | 45.91 | 29.72 | 17.24 | 7.03 |  |
| E2354 | BL-hESC | 33.39 | 62.01 | 2.89 | 1.75 | FIG. 7C |
|  | Hg30 St3 + 4-hESC | 16.18 | 73.00 | 8.10 | 1.86 |  |

BL, baseline conditions;
hIPSC, human induced pluripotent stem cells;
Hg30, 30 ng/mL heregulin-11
St 3 + 4, Stages 3 and 4;
hESC, human embryonic stem cells,
CHGA, chromogranin A Under certain conditions, the ratio of subpopulations of cells in the PEC (hESC, E2354) and iPEC (E2314, E2344, E2347) populations were altered. For example, sometimes, the percentage of endocrine (CHGA+) cells decreased and the percentage of non-endocrine cells (CHGA−/NKX6.1+/PDX1+) increased as compared to the baseline (no heregulin) conditions. Although it appeared that heregulin was responsible for changing the proportions of endocrine cells relative to non-endocrine cells in these PEC and iPEC populations, in experiment #2380 (E2380), the level of endocrine (CHGA+) cells increased rather than decreased with the addition of heregulin.

To determine whether the change in the composition of PEC and iPEC populations affected in vivo function, PEC and iPEC grafts from most of the experiments described in Table 11 were transplanted into mice substantially as previously described herein and in Applicant's other patent and non-patent publications, including Schulz et al. (2012) and Kroon et al (2008), supra and U.S. Pat. Nos. 7,534,608; 7,695,965; 7,993,920 and 8,278,106, supra. Briefly, PEC and iPEC populations were wholly encapsulated with a biodegradable semi-permeable cell encapsulation device, some of which included micro perforations. The devices were manufactured by Applicant and are described in detail in U.S. Pat. No. 8,278,106, entitled ENCAPSULATION OF PANCREATIC CELLS FROM HUMAN PLURIPOTENT STEM CELLS, filed Nov. 13, 2009, the disclosure of which is incorporated herein by reference in its entirety. Glucose stimulated insulin secretion (GSIS) assays were performed starting from about 56 days post-implant. Blood was collected prior to (fasting) and at combinations of 30 and/or 60 minutes after glucose administration. Graft function was assessed by measuring human C-peptide concentrations in the serum in response to glucose administration.

The amount of human C-peptide released into the serum is indicative of the amount of insulin released. C-peptide is a short 31 amino acid peptide connecting or linking A and B-chains of proinsulin and preproinsulin, which is secreted by functioning beta or insulin secreting cells. As discussed previously by Kroon et al. (2008) supra and others, human C-peptide measurements are appropriate for assessing the release of de novo-generated insulin by the implanted cells. Hence, levels of human C-peptide in the serum of these animals is a measure of the in vivo function of the mature PEC and iPEC grafts. Human C-peptide was detected in the serum by at least 8 weeks post-implant. With additional weeks of implant and fasting, glucose-stimulated C-peptide levels increased with the peak levels of C-peptide shifting from 60 minutes to 30 minutes post-glucose administration, which is indicative of a more rapid response to glucose challenge as the insulin cells mature. There were a few mice that failed to exhibit function, or were sacrificed due to poor health; however, these mice were in cohorts that otherwise exhibited high-functioning animals, thus suggesting a failure of engraftment rather than an inability of the implanted cells to differentiate and function.

Figure 7A:
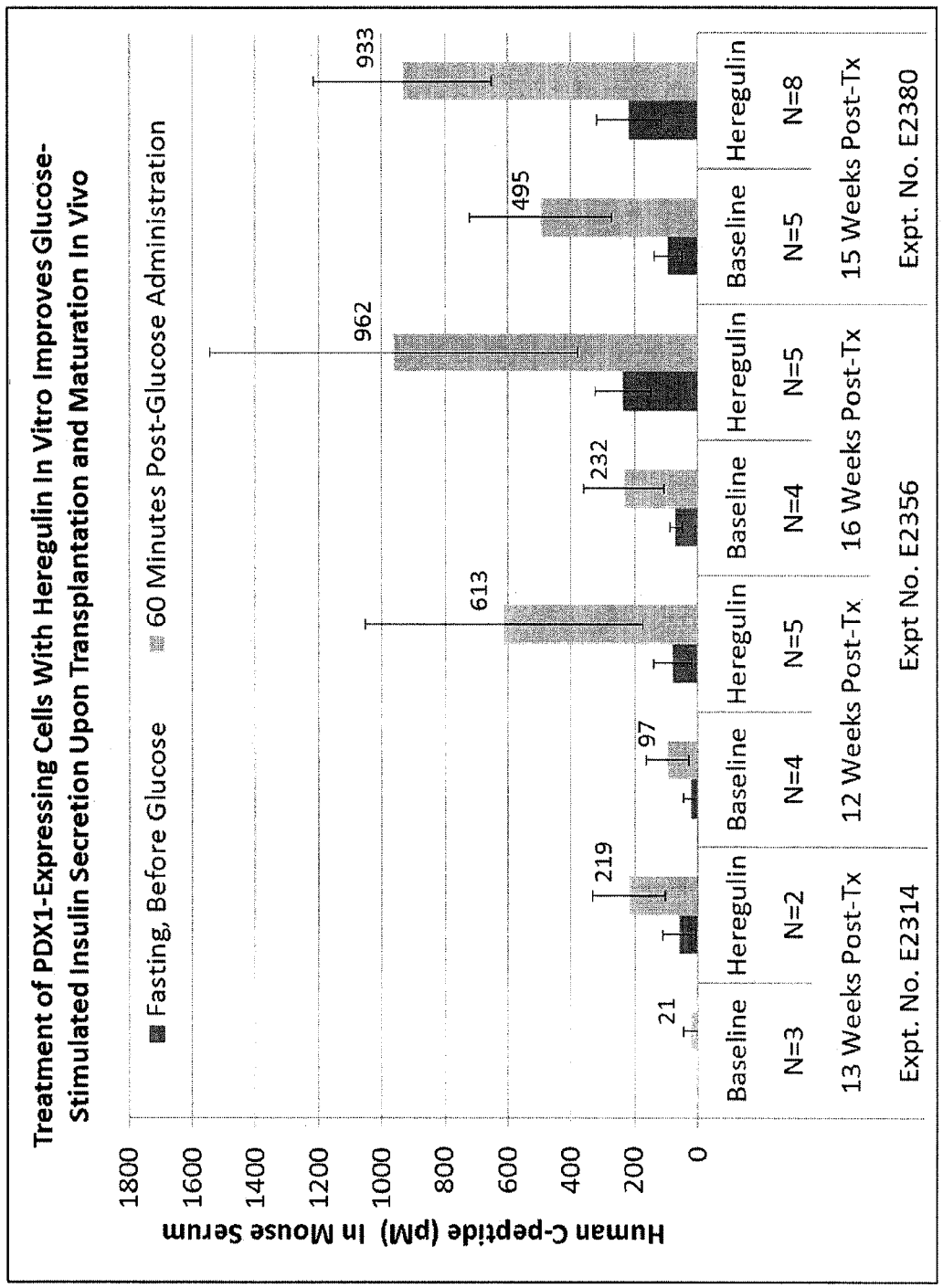
FIGS. 7A-C are graphs showing the concentrations of human C-peptide and insulin in sera of implanted mice for experiments E2314, E2356 and E2380 (FIG. 7A), E2347 (FIG. 7B), and E2354 (FIG. 7C) as indicated in Table 9. Mice implanted with PEC were analyzed at the indicated post-engraftment times for serum levels of human C-peptide at fasting, and 30 min and 60 min after intraperitoneal glucose administration.
Figure 7B:
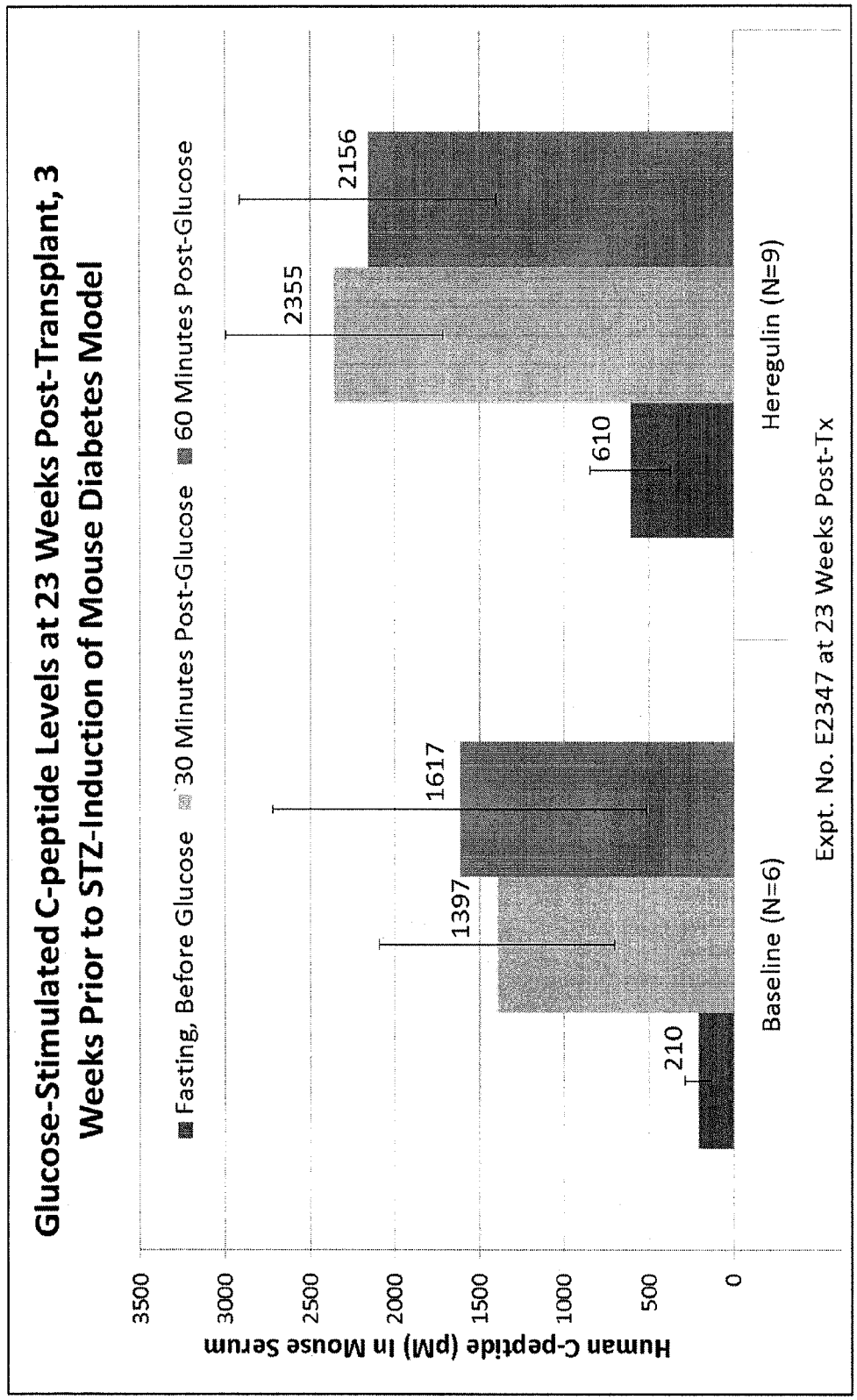
Figure 7C:
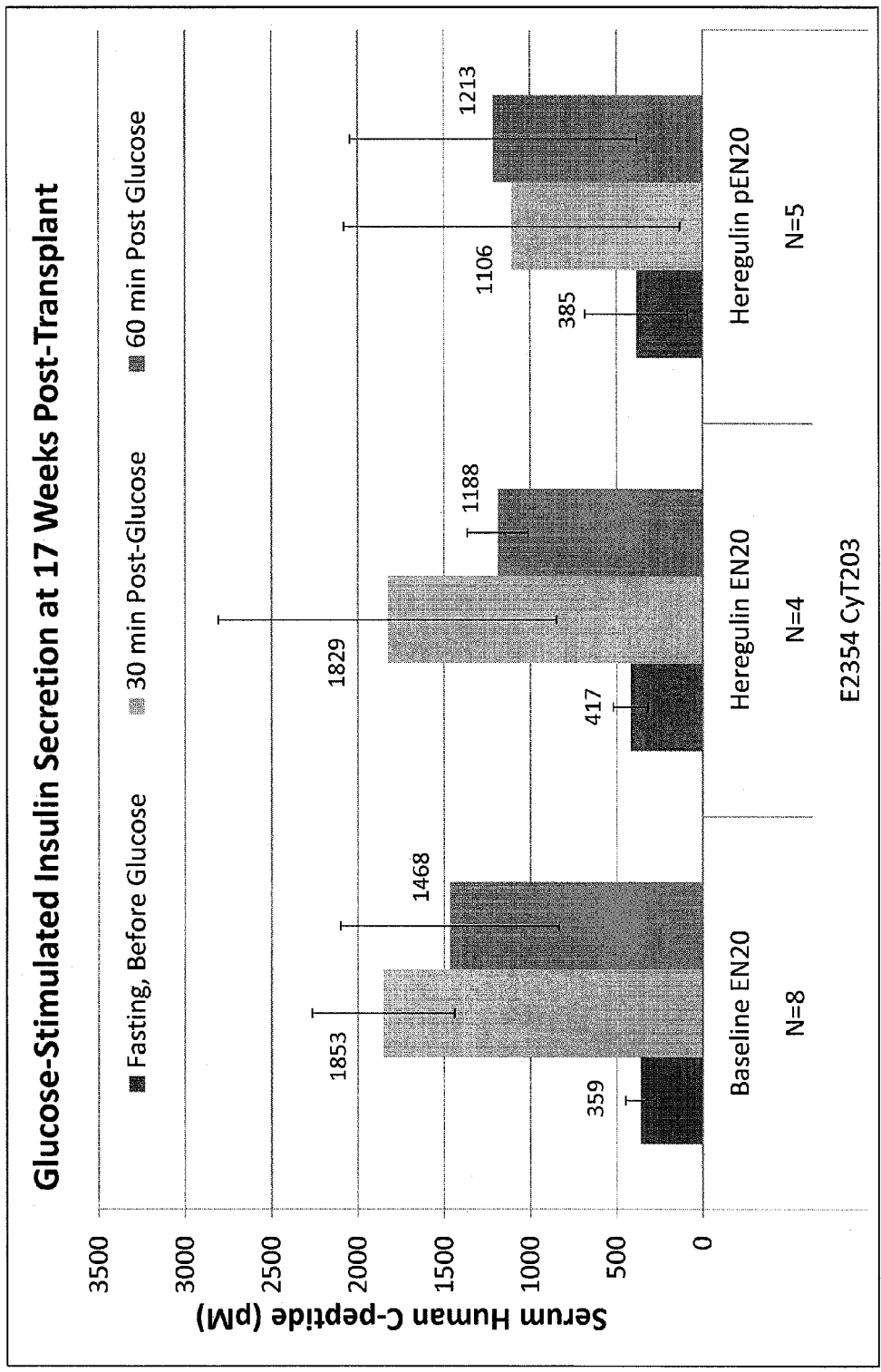
Figure 8A:
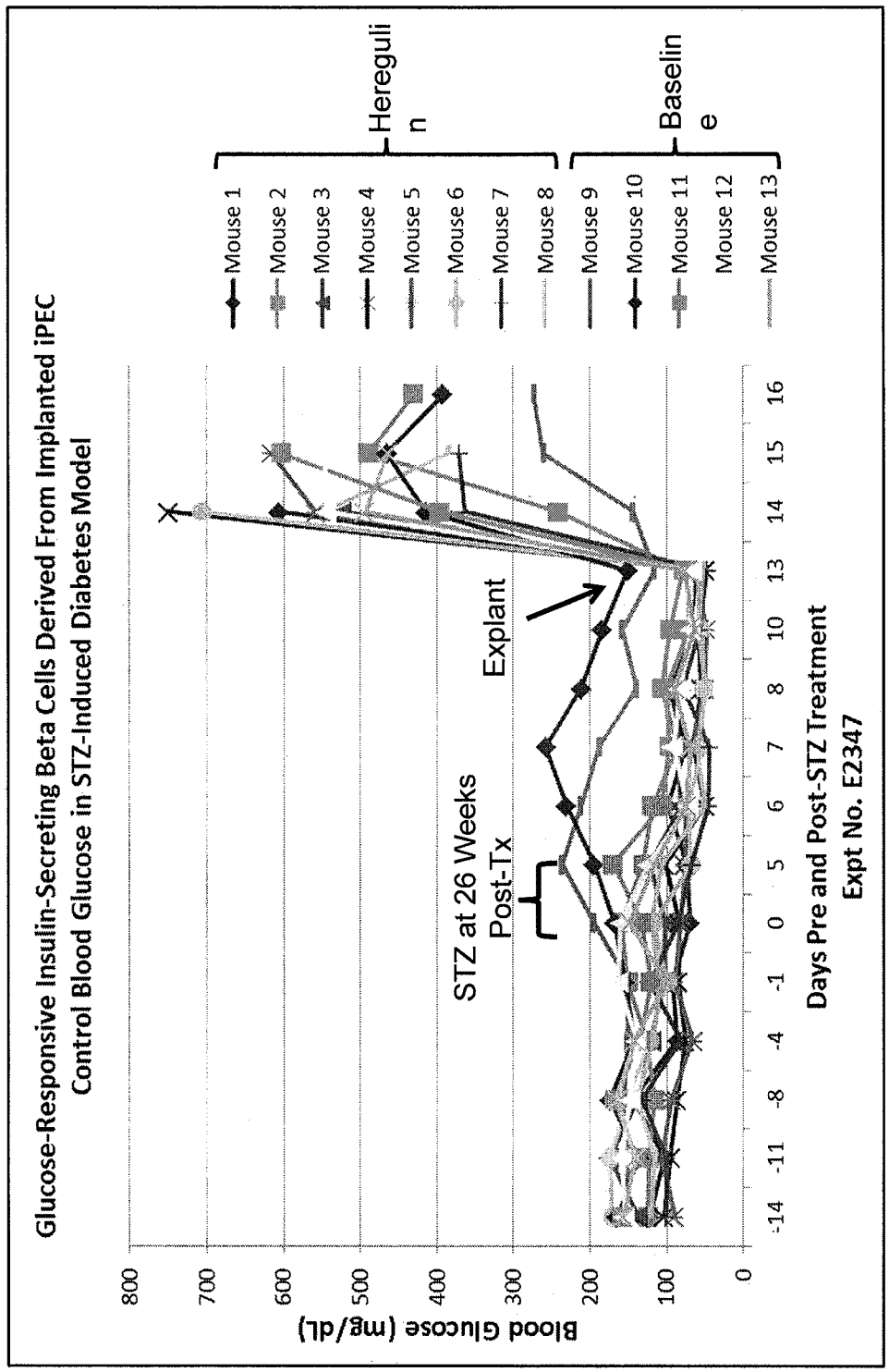
FIGS. 8A and 8B are graphs showing the results of blood glucose analyses of STZ-treated mice for Experiment #2347.
Figure 8B:
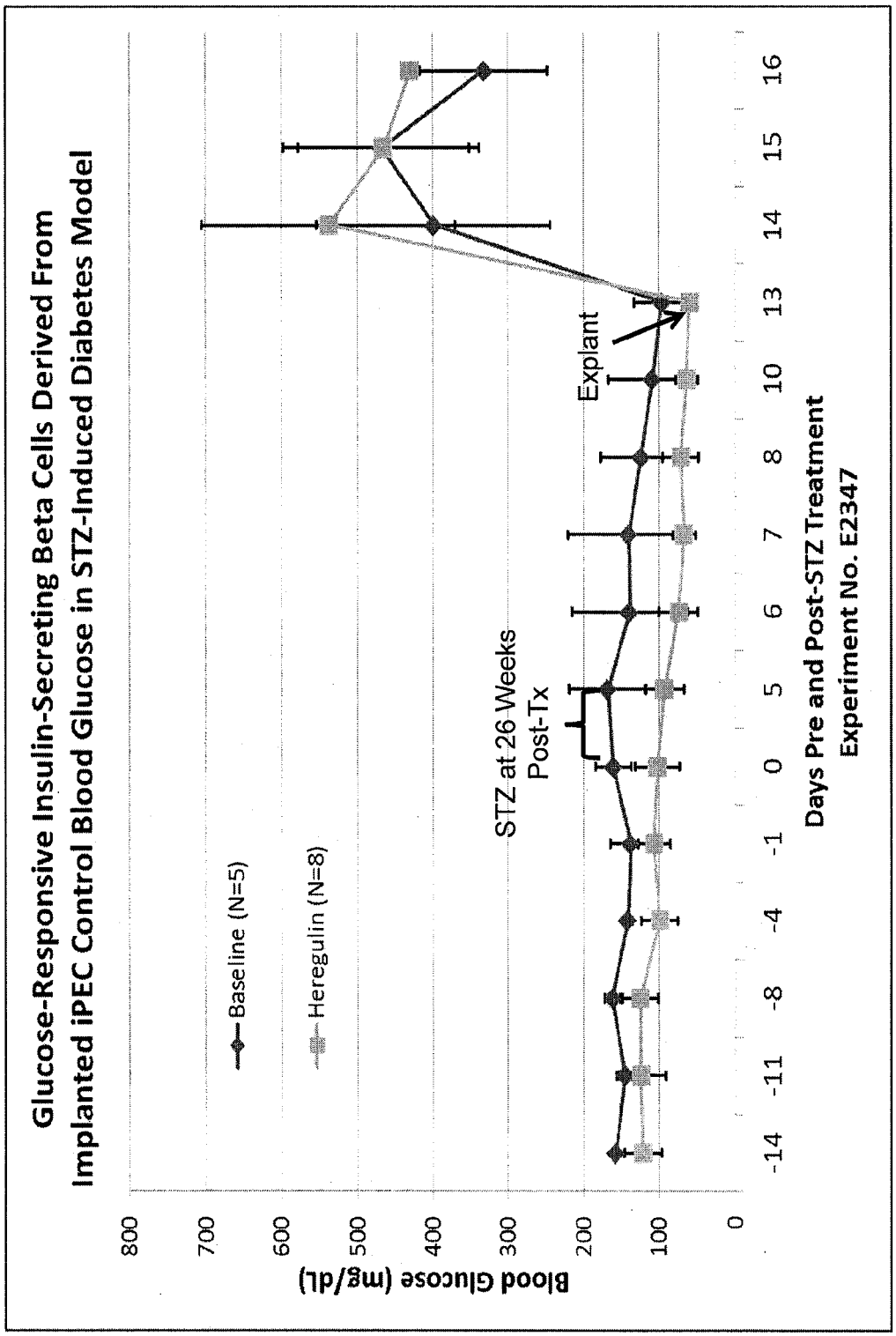

FIGS. 7A-C show human C-peptide levels in the serum post glucose administration for all of the experiments indicated in Table 11 except E2344. FIGS. 7A-C show that as compared to baseline controls, those grafts resulting from heregulin treatment, in general, had higher levels of serum human C-peptide. For example, in FIG. 7A, in experiment 2380, there is about a 5-fold increase (933 pM:200 pM at 60 minutes post glucose administration) in the grafts resulting from the heregulin treatment as compared to those prepared without heregulin (baseline). Heregulin seems to have lesser effect on PEC produced from hESC, since experiment 2354 (FIG. 7C) does not show higher levels of serum C-peptide in those grafts resulting from heregulin treatment as compared to the baseline controls. Further, when comparing PEC derived from hESC (CyT203) and iPEC derived from iPSC, the iPEC grafts have comparable function in vivo to the PEC grafts (e.g. compare FIG. 7A and FIG. 7B (iPSC grafts) with FIG. 7C (CyT203 hESC). As such, the iPEC grafts are as robust as the PEC grafts. Also, the relative ratios of endocrine to non-endocrine cells, which appeared to affect some of the iPEC populations (e.g. E2314, E2347 and E2354), did not appear to affect in vivo function because iPEC from E2380, which did not have the same shift in endocrine and non-endocrine subpopulations, also showed good function (see FIG. 7A-C).

In addition to being tested for glucose-stimulated insulin secretion, the mature iPEC grafts were tested to determine whether they alone were able to maintain euglycemia, similar to euglycemia maintained by PEC derived from hESC, if the host animal's beta cells were destroyed. This involved destroying the beta cells of the implanted mouse using the beta cell toxin, streptozotocin (STZ), which exhibits greater cytotoxicity against murine beta cells as compared to human beta cells. Measurements of random non-fasting blood glucose were taken for each mouse before and after STZ-treatment. Upon explant of the iPEC graft on day 13 post-STZ treatment, hyperglycemia resumed (note the spike in blood glucose), which demonstrates the control of glycemia by the iPEC graft rather than the endogenous mouse pancreas (see FIG. 8A and FIG. 8B.

In addition there appeared to be a synergistic effect when heregulin and a rho-kinase inhibitor were provided during stages 1-4 of differentiation (see Table 10). For example, iPSC treated with heregulin at stages 3 and 4 without a rho-kinase inhibitor resulted in visibly poor cell mass such that it made implantation impossible. Further support for synergy of heregulin and a rho-kinase inhibitor was evident in some of the experiments, e.g. E2356, E2380, whereby baseline conditions with a rho-kinase inhibitor alone did not function as robustly as a graft with rho-kinase inhibitor and heregulin (see FIGS. 7A and B). It appears that treatment with heregulin and a rho-kinase inhibitor were not additive because addition of heregulin alone provided insufficient cell mass for transplant and addition of a rho-kinase inhibitor alone (baseline conditions) had poor in vivo function. As such, the provision of heregulin alone or a rho-kinase inhibitor alone is not substantially similar to the sum effect of the two combined. That is, alone neither results in robust glucose responsiveness in vivo but combined they produce glucose responsiveness similar to that of hES-derived cells. Accordingly, it appeared that the provision of both heregulin and a rho-kinase inhibitor is synergistic since their combined effect is greater than the sum of the effect of each separately. That is, the rho-kinase inhibitor and heregulin treated iPEC matured in vivo exhibiting glucose-stimulated insulin secretion, and were able to maintain euglycemia in a diabetes mouse model (see FIG. 7A-B and FIG. 8A-B).

ERBB functionality requires ligand binding, receptor dimerization, and receptor trafficking. Variability in each process may produce differential regulation of the receptors and the downstream signals they control. For example, distinct ERBB ligands bind ERBB receptors with different affinities, thereby altering the patterns and dynamics of ERBB dimer formation. Table 12 shows the many possible different combinations of ligands and receptor binding complexes. Reviews relating to the complexity of this system are provided by Oda, et al. (2005) A comprehensive pathway map of epidermal growth factor receptor signaling, *Mol. Syst. Biol.,* 1 (2005) and Lazzara et al. (2009) Quantitative modeling perspectives on the ERRB system of cell regulatory processes, *Experimental Cell Research* 315(4):717-725, the disclosures of which are incorporated herein by reference in their entireties.

TABLE 12

ERRB Receptor Tyrosine Kinases and Their Ligands

| | | ERRB Receptor Tyrosine Kinases | | | |
|---|---|---|---|---|---|
| | | ErbB-1 | ErbB-2 | ErbB-3 | ErbB-4 |
| Ligands | EGF | x | | | |
| | TGFa | x | | | |
| | HB-EGF | x | | | X |
| | EPR | x | | | X |
| | EPG | x | | | |
| | b-Cell | x | | | X |

TABLE 12-continued

ERRB Receptor Tyrosine Kinases and Their Ligands

| | ERRB Receptor Tyrosine Kinases | | | |
|---|---|---|---|---|
| | ErbB-1 | ErbB-2 | ErbB-3 | ErbB-4 |
| AR | x | | | |
| Hrg1 | | | x | X |
| Hrg2 | | | x | X |
| Hrg3 | | | | X |
| Hrg4 | | | | X |

ERRB Receptor Tyrosine Kinases: ErbB1 (also named Her1, or epidermal growth factor receptor, EGFR); ErbB2 (also named human epidermal growth factor receptor, or Her2; or Neu); ErbB3 (also named, Her3), ErbB4 (also named Her4), ERBB Ligands: EGF, epidermal growth factor; TGFβ, transforming growth factor β; HB-EGF, heparin-binding EGF-like growth factor; EPR, epiregulin; EPG, Epigen; AR, amphiregulin, Hrg1, heregulin-1 or neuregulin-1; Hrg2, heregulin-2 or neuregulin-2; Hrg3, heregulin-3 or neuregulin-3; Hrg4, heregulin-4 or neuregulin-4; heregulin is used interchangeably with neuregulin.

Figure 6:
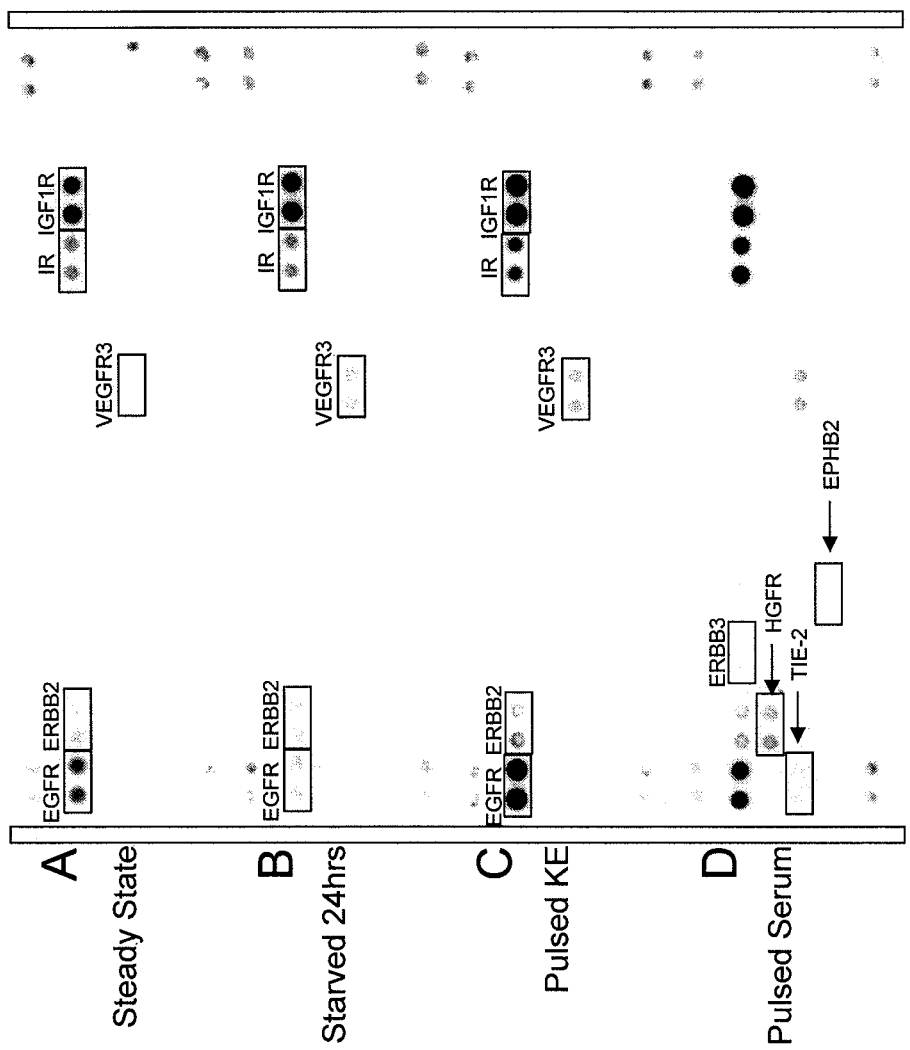
FIGS. 6A-D are an RTK array analyses of iPS cell-derived pancreatic endoderm cells (PEC) under four different conditions (A, B, C and D as described in Example 5. Tyrosine phosphorylation of certain RTKs are observed by the identification of high to low-intensity signals. IGF1R/IR and ERBB (EGFR) family members are identified or boxed.

Huotari et al. suggested that neuregulin-4 may modulate the relative levels of the endocrine cell subpopulations by increasing the number of somatostatin (delta) cells at the expense of glucagon (alpha) cells, and that neuregulin-4 did not affect the ratio of exocrine (e.g., amylase) to endocrine (e.g., β-insulin, α-glucagon, δ-somatostatin, PP-pancreatic polypeptide) cells. These studies, however, were performed by incubating neuregulin-4 on whole mount organ tissue cultures obtained from day E12.5 mice. These mouse explant cell populations were differentiated further than the stage 3 (e.g. PDX1 negative foregut endoderm) and/or stage 4 (PDX1 positive foregut endoderm) cell populations described herein. Neuregulin-4 only binds to ERBB4 RTK such that only the endocrine sub-population of the whole mount mouse culture can be modulated by neuregulin-4 in this context. Thus, treatment of the stage 3 (PDX1 negative foregut endoderm) and/or stage 4 (PDX1 positive foregut endoderm) cells as described herein with a different ERBB ligand, e.g. Hrg1, would not be expected to modulate the relative endocrine subpopulation as in Huotari because Hrg1 has already been shown to bind to ERBB3 and induce dimerization of ERBB2/3. However, due to the low-level expression of ERBB2 and 3 in PEC as shown in FIG. 6, it was unclear whether stages 3 and 4 type cells would express low or high levels of ERBB2 and 3 to bind to Hrg1.

Further, in a different context, Applicant had described that Hrg1 bound to ERRB 2/3 and promoted self-renewal of pluripotent stem cells (see Wang et al (2007). Although it is possible that Hrg1 may act in the same capacity in the context of stage 3 and 4, Applicant has previously described that most of the cell expansion for production of PEC occurs at the pluripotent stem cell stage (stage 0). During stage 0 the hESC are grown, passaged and expanded for about two (2) weeks. Thus, most of the cell expansion or self-renewal to produce the cell expansion does not occur during stages 1-4. See Schulz et al. (2012) supra. Also, assuming that ERRB2/3 is present during stages 3 and 4, one might expect heregulin to have the same effect as with pluripotent stem cells (self renewal) as opposed to impacting directed differentiation. The difference in function appears then to depend on the context, that is, pluripotent stem cells versus an endoderm or pancreatic-lineage cell type.

In summary, providing heregulin or heregulin and a rho-kinase inhibitor in vitro to foregut endoderm (stage 3) and PDX1 expressing pancreatic endoderm cells (end of stage 3 and stage 4) produced PEC and iPEC populations, that when transplanted, mature and develop into glucose responsive insulin-secreting cells in vivo (see FIGS. 7 and 8). Such use of heregulin or heregulin and a rho-kinase inhibitor has been reported here for the first time. Such use and effect are not discernible from that previously described in the patent or non-patent literature.

It will be appreciated that the Q-PCR results described herein can be further confirmed by immunocytochemistry (ICC), and be readily performed by those of ordinary skill in the art.

The methods, compositions, and devices described herein are presently representative of preferred embodiments and are exemplary and are not intended as limitations on the scope of the invention. Changes therein and other uses will occur to those skilled in the art which are encompassed within the spirit of the invention and are defined by the scope of the disclosure. Accordingly, it will be apparent to one skilled in the art that varying substitutions and modifications may be made to the invention disclosed herein without departing from the scope and spirit of the invention.

As used in the claims below and throughout this disclosure, by the phrase "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they affect the activity or action of the listed elements. Also, it will be appreciated that in embodiments where numerical values, such as amounts, concentrations, percentages, proportions or ranges, are recited the value that is referred to can be "at least about" the numerical value, "about" the numerical value or "at least" the numerical value.

What is claimed is:

1. An in vitro human pancreatic endoderm cell population in a media comprising an ERBB receptor tyrosine kinase activating agent.

2. The pancreatic endoderm cell population of claim 1, wherein the ERRB receptor tyrosine kinase activating agent comprises an epidermal growth factor (EGF) family ligand.

3. The pancreatic endoderm cell population of claim 2, wherein the EGF family ligand is selected from the group consisting of Heregulin-1 (Neuregulin-1), Heregulin-2 (Neuregulin-2), Heregulin-3 (Neuregulin-3) and Heregulin-4 (Neuregulin-4).

4. The pancreatic endoderm cell population of claim 3, wherein the EGF family ligand comprises heregulin-1 and heregulin-4.

5. The pancreatic endoderm cell population of claim 3, wherein the EGF family ligand comprises Heregulin-4 (Neuregulin-4).

6. The pancreatic endoderm population of claim 3 wherein the EGF family ligand is Heregulin-1 (Neuregulin-1).

7. The pancreatic endoderm population of claim 6 wherein Heregulin-1 (Neuregulin-1) is heregulin-1β.

8. The pancreatic endoderm population of claim 7 wherein the heregulin-1β is a fragment of the natural protein.

* * * * *

```
                              SEQUENCE LISTING

<160> NUMBER OF SEQ ID NOS: 46

<210> SEQ ID NO 1
<211> LENGTH: 21
<212> TYPE: DNA
<213> ORGANISM: Artificial Sequence
<220> FEATURE:
<223> OTHER INFORMATION: Oligonucleotide Primers

<400> SEQUENCE: 1
aagaggccat caagcagatc a                                                  21

<210> SEQ ID NO 2
<211> LENGTH: 17
<212> TYPE: DNA
<213> ORGANISM: Artificial Sequence
<220> FEATURE:
<223> OTHER INFORMATION: Oligonucleotide Primers

<400> SEQUENCE: 2
caggaggcgc atccaca                                                       17

<210> SEQ ID NO 3
<211> LENGTH: 20
<212> TYPE: DNA
<213> ORGANISM: Artificial Sequence
<220> FEATURE:
<223> OTHER INFORMATION: Oligonucleotide Primers

<400> SEQUENCE: 3
ctggcctgta cccctcatca                                                    20

<210> SEQ ID NO 4
<211> LENGTH: 21
<212> TYPE: DNA
<213> ORGANISM: Artificial Sequence
<220> FEATURE:
<223> OTHER INFORMATION: Oligonucleotide Primers

<400> SEQUENCE: 4
cttcccgtct ttgtccaaca a                                                  21

<210> SEQ ID NO 5
<211> LENGTH: 21
<212> TYPE: DNA
<213> ORGANISM: Artificial Sequence
<220> FEATURE:
<223> OTHER INFORMATION: Oligonucleotide Primers
```

```
<400> SEQUENCE: 5
aagtctacca aagctcacgc g                                              21

<210> SEQ ID NO 6
<211> LENGTH: 15
<212> TYPE: DNA
<213> ORGANISM: Artificial Sequence
<220> FEATURE:
<223> OTHER INFORMATION: Oligonucleotide Primers

<400> SEQUENCE: 6
gtaggcgccg cctgc                                                     15

<210> SEQ ID NO 7
<211> LENGTH: 24
<212> TYPE: DNA
<213> ORGANISM: Artificial Sequence
<220> FEATURE:
<223> OTHER INFORMATION: Oligonucleotide Primers

<400> SEQUENCE: 7
gctcatcgct ctctattctt ttgc                                           24

<210> SEQ ID NO 8
<211> LENGTH: 21
<212> TYPE: DNA
<213> ORGANISM: Artificial Sequence
<220> FEATURE:
<223> OTHER INFORMATION: Oligonucleotide Primers

<400> SEQUENCE: 8
ggttgaggcg tcatcctttc t                                              21

<210> SEQ ID NO 9
<211> LENGTH: 18
<212> TYPE: DNA
<213> ORGANISM: Artificial Sequence
<220> FEATURE:
<223> OTHER INFORMATION: Oligonucleotide Primers

<400> SEQUENCE: 9
gggagcggtg aagatgga                                                  18

<210> SEQ ID NO 10
<211> LENGTH: 22
<212> TYPE: DNA
<213> ORGANISM: Artificial Sequence
<220> FEATURE:
<223> OTHER INFORMATION: Oligonucleotide Primers

<400> SEQUENCE: 10
tcatgttgct cacggaggag ta                                             22

<210> SEQ ID NO 11
<211> LENGTH: 24
<212> TYPE: DNA
<213> ORGANISM: Artificial Sequence
<220> FEATURE:
<223> OTHER INFORMATION: Oligonucleotide Primers

<400> SEQUENCE: 11
aagcatttac tttgtggctg gatt                                           24
```

```
<210> SEQ ID NO 12
<211> LENGTH: 25
<212> TYPE: DNA
<213> ORGANISM: Artificial Sequence
<220> FEATURE:
<223> OTHER INFORMATION: Oligonucleotide Primers

<400> SEQUENCE: 12
tgatctggat ttctcctctg tgtct                                              25

<210> SEQ ID NO 13
<211> LENGTH: 18
<212> TYPE: DNA
<213> ORGANISM: Artificial Sequence
<220> FEATURE:
<223> OTHER INFORMATION: Oligonucleotide Primers

<400> SEQUENCE: 13
cgctccgctt agcagcat                                                      18

<210> SEQ ID NO 14
<211> LENGTH: 22
<212> TYPE: DNA
<213> ORGANISM: Artificial Sequence
<220> FEATURE:
<223> OTHER INFORMATION: Oligonucleotide Primers

<400> SEQUENCE: 14
gtgttgcctc tatccttccc at                                                 22

<210> SEQ ID NO 15
<211> LENGTH: 20
<212> TYPE: DNA
<213> ORGANISM: Artificial Sequence
<220> FEATURE:
<223> OTHER INFORMATION: Oligonucleotide Primers

<400> SEQUENCE: 15
gaagaaggaa gccgtccaga                                                    20

<210> SEQ ID NO 16
<211> LENGTH: 20
<212> TYPE: DNA
<213> ORGANISM: Artificial Sequence
<220> FEATURE:
<223> OTHER INFORMATION: Oligonucleotide Primers

<400> SEQUENCE: 16
gaccttcgag tgctgatccg                                                    20

<210> SEQ ID NO 17
<211> LENGTH: 18
<212> TYPE: DNA
<213> ORGANISM: Artificial Sequence
<220> FEATURE:
<223> OTHER INFORMATION: Oligonucleotide Primers

<400> SEQUENCE: 17
ggcgcagcag aatccaga                                                      18

<210> SEQ ID NO 18
<211> LENGTH: 20
<212> TYPE: DNA
<213> ORGANISM: Artificial Sequence
<220> FEATURE:
<223> OTHER INFORMATION: Oligonucleotide Primers
```

```
<220> FEATURE:
<221> NAME/KEY: misc_feature
<222> LOCATION: (1)...(20)
<223> OTHER INFORMATION: n = a, c, t or g

<400> SEQUENCE: 18
nnnnnnnnnn nnnnnnnnnn                                            20

<210> SEQ ID NO 19
<211> LENGTH: 16
<212> TYPE: DNA
<213> ORGANISM: Artificial Sequence
<220> FEATURE:
<223> OTHER INFORMATION: Oligonucleotide Primers

<400> SEQUENCE: 19
caccgcgggc atgatc                                                16

<210> SEQ ID NO 20
<211> LENGTH: 19
<212> TYPE: DNA
<213> ORGANISM: Artificial Sequence
<220> FEATURE:
<223> OTHER INFORMATION: Oligonucleotide Primers

<400> SEQUENCE: 20
acttccccag gaggttcga                                             19

<210> SEQ ID NO 21
<211> LENGTH: 20
<212> TYPE: DNA
<213> ORGANISM: Artificial Sequence
<220> FEATURE:
<223> OTHER INFORMATION: Oligonucleotide Primers

<400> SEQUENCE: 21
ggccttcagt actccctgca                                            20

<210> SEQ ID NO 22
<211> LENGTH: 21
<212> TYPE: DNA
<213> ORGANISM: Artificial Sequence
<220> FEATURE:
<223> OTHER INFORMATION: Oligonucleotide Primers

<400> SEQUENCE: 22
gggacttgga gcttgagtcc t                                          21

<210> SEQ ID NO 23
<211> LENGTH: 21
<212> TYPE: DNA
<213> ORGANISM: Artificial Sequence
<220> FEATURE:
<223> OTHER INFORMATION: Oligonucleotide Primers

<400> SEQUENCE: 23
gaaggtcatc atctgccatc g                                          21

<210> SEQ ID NO 24
<211> LENGTH: 19
<212> TYPE: DNA
<213> ORGANISM: Artificial Sequence
<220> FEATURE:
<223> OTHER INFORMATION: Oligonucleotide Primers
```

```
<400> SEQUENCE: 24
ggccataatc agggtcgct                                                  19

<210> SEQ ID NO 25
<211> LENGTH: 20
<212> TYPE: DNA
<213> ORGANISM: Artificial Sequence
<220> FEATURE:
<223> OTHER INFORMATION: Oligonucleotide Primers

<400> SEQUENCE: 25
ccccagactc cgtcagtttc                                                 20

<210> SEQ ID NO 26
<211> LENGTH: 19
<212> TYPE: DNA
<213> ORGANISM: Artificial Sequence
<220> FEATURE:
<223> OTHER INFORMATION: Oligonucleotide Primers

<400> SEQUENCE: 26
tccgtctggt tgggttcag                                                  19

<210> SEQ ID NO 27
<211> LENGTH: 23
<212> TYPE: DNA
<213> ORGANISM: Artificial Sequence
<220> FEATURE:
<223> OTHER INFORMATION: Oligonucleotide Primers

<400> SEQUENCE: 27
ccagaaagga tgcctcataa agg                                             23

<210> SEQ ID NO 28
<211> LENGTH: 18
<212> TYPE: DNA
<213> ORGANISM: Artificial Sequence
<220> FEATURE:
<223> OTHER INFORMATION: Oligonucleotide Primers

<400> SEQUENCE: 28
tctgcgcgcc cctagtta                                                   18

<210> SEQ ID NO 29
<211> LENGTH: 19
<212> TYPE: DNA
<213> ORGANISM: Artificial Sequence
<220> FEATURE:
<223> OTHER INFORMATION: Oligonucleotide Primers

<400> SEQUENCE: 29
tgggctcgag aaggatgtg                                                  19

<210> SEQ ID NO 30
<211> LENGTH: 20
<212> TYPE: DNA
<213> ORGANISM: Artificial Sequence
<220> FEATURE:
<223> OTHER INFORMATION: Oligonucleotide Primers

<400> SEQUENCE: 30
gcatagtcgc tgcttgatcg                                                 20
```

```
<210> SEQ ID NO 31
<211> LENGTH: 20
<212> TYPE: DNA
<213> ORGANISM: Artificial Sequence
<220> FEATURE:
<223> OTHER INFORMATION: Oligonucleotide Primers

<400> SEQUENCE: 31
ccgagtccag gatccaggta                                               20

<210> SEQ ID NO 32
<211> LENGTH: 19
<212> TYPE: DNA
<213> ORGANISM: Artificial Sequence
<220> FEATURE:
<223> OTHER INFORMATION: Oligonucleotide Primers

<400> SEQUENCE: 32
ctctgacgcc gagacttgg                                                19

<210> SEQ ID NO 33
<211> LENGTH: 19
<212> TYPE: DNA
<213> ORGANISM: Artificial Sequence
<220> FEATURE:
<223> OTHER INFORMATION: Oligonucleotide Primers

<400> SEQUENCE: 33
cctcttgcaa tgcggaaag                                                19

<210> SEQ ID NO 34
<211> LENGTH: 19
<212> TYPE: DNA
<213> ORGANISM: Artificial Sequence
<220> FEATURE:
<223> OTHER INFORMATION: Oligonucleotide Primers

<400> SEQUENCE: 34
cgggaggaag gctctcact                                                19

<210> SEQ ID NO 35
<211> LENGTH: 23
<212> TYPE: DNA
<213> ORGANISM: Artificial Sequence
<220> FEATURE:
<223> OTHER INFORMATION: Oligonucleotide Primers

<400> SEQUENCE: 35
gaggagaaag tggaggtctg gtt                                           23

<210> SEQ ID NO 36
<211> LENGTH: 21
<212> TYPE: DNA
<213> ORGANISM: Artificial Sequence
<220> FEATURE:
<223> OTHER INFORMATION: Oligonucleotide Primers

<400> SEQUENCE: 36
ctctgatgag gaccgcttct g                                             21

<210> SEQ ID NO 37
<211> LENGTH: 21
<212> TYPE: DNA
<213> ORGANISM: Artificial Sequence
<220> FEATURE:
<223> OTHER INFORMATION: Oligonucleotide Primers
```

-continued

<400> SEQUENCE: 37
acagtgccct tcagccagac t                                      21

<210> SEQ ID NO 38
<211> LENGTH: 25
<212> TYPE: DNA
<213> ORGANISM: Artificial Sequence
<220> FEATURE:
<223> OTHER INFORMATION: Oligonucleotide Primers

<400> SEQUENCE: 38
acaactactt tttcacagcc ttcgt                                  25

<210> SEQ ID NO 39
<211> LENGTH: 23
<212> TYPE: DNA
<213> ORGANISM: Artificial Sequence
<220> FEATURE:
<223> OTHER INFORMATION: Oligonucleotide Primers

<400> SEQUENCE: 39
gagaaaccca ctggagatga aca                                    23

<210> SEQ ID NO 40
<211> LENGTH: 23
<212> TYPE: DNA
<213> ORGANISM: Artificial Sequence
<220> FEATURE:
<223> OTHER INFORMATION: Oligonucleotide Primers

<400> SEQUENCE: 40
ctcatggcaa agttcttcca gaa                                    23

<210> SEQ ID NO 41
<211> LENGTH: 19
<212> TYPE: DNA
<213> ORGANISM: Artificial Sequence
<220> FEATURE:
<223> OTHER INFORMATION: Oligonucleotide Primers

<400> SEQUENCE: 41
atgcaccgct acgacatgg                                         19

<210> SEQ ID NO 42
<211> LENGTH: 21
<212> TYPE: DNA
<213> ORGANISM: Artificial Sequence
<220> FEATURE:
<223> OTHER INFORMATION: Oligonucleotide Primers

<400> SEQUENCE: 42
ctcatgtagc cctgcgagtt g                                      21

<210> SEQ ID NO 43
<211> LENGTH: 20
<212> TYPE: DNA
<213> ORGANISM: Artificial Sequence
<220> FEATURE:
<223> OTHER INFORMATION: Oligonucleotide Primers

<400> SEQUENCE: 43
ctggctgtgg caaggtcttc                                        20

```
<210> SEQ ID NO 44
<211> LENGTH: 20
<212> TYPE: DNA
<213> ORGANISM: Artificial Sequence
<220> FEATURE:
<223> OTHER INFORMATION: Oligonucleotide Primers

<400> SEQUENCE: 44
cagccctcaa actcgcactt                                               20

<210> SEQ ID NO 45
<211> LENGTH: 18
<212> TYPE: DNA
<213> ORGANISM: Artificial Sequence
<220> FEATURE:
<223> OTHER INFORMATION: Oligonucleotide Primers

<400> SEQUENCE: 45
atcgaggagc gccacaac                                                 18

<210> SEQ ID NO 46
<211> LENGTH: 19
<212> TYPE: DNA
<213> ORGANISM: Artificial Sequence
<220> FEATURE:
<223> OTHER INFORMATION: Oligonucleotide Primers

<400> SEQUENCE: 46
tgctggatgg tgtcctggt                                                19
```